United States Patent [19]
Sorge et al.

[11] Patent Number: 6,017,701
[45] Date of Patent: *Jan. 25, 2000

[54] METHODS AND ADAPTORS FOR GENERATING SPECIFIC NUCLEIC ACID POPULATIONS

[75] Inventors: Joseph A. Sorge, Rancho Santa Fe; Rebecca Lynn Mullinax, San Diego, both of Calif.

[73] Assignee: Stratgene, La Jolla, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/779,355

[22] Filed: Jan. 6, 1997

Related U.S. Application Data

[63] Continuation-in-part of application No. 08/775,993, Jan. 3, 1997, abandoned
[60] Provisional application No. 60/033,175, Dec. 13, 1996.

[51] Int. Cl.[7] .............................. C12Q 1/68; C12P 19/34; C07H 21/04
[52] U.S. Cl. ........................... 435/6; 435/91.1; 435/91.2; 536/24.2; 536/24.33
[58] Field of Search ............................. 435/6, 91.2, 91.1, 435/810; 536/24.2, 24.33

[56] References Cited

U.S. PATENT DOCUMENTS

| | | | |
|---|---|---|---|
| 4,321,365 | 3/1982 | Wu et al. ................................... | 536/27 |
| 4,683,202 | 7/1987 | Mullis ...................................... | 435/91 |
| 5,436,142 | 7/1995 | Wigler et al. ........................... | 435/91.2 |
| 5,501,964 | 3/1996 | Wigler et al. ........................... | 435/91.2 |
| 5,525,471 | 6/1996 | Zeng .......................................... | 435/6 |
| 5,565,340 | 10/1996 | Chenchik et al. ...................... | 435/91.2 |
| 5,726,022 | 3/1998 | Burmer ..................................... | 435/6 |
| 5,804,382 | 9/1998 | Sytkowski et al. ........................ | 435/6 |

OTHER PUBLICATIONS

Zeng, Jin et al., "Differential cDNA cloning by enzymatic degrading subtraction (EDS)", *Nucleic Acids Research*, 22:4381–4385 (1994).

Hubank, M. et al., "Identifying differences in mRNA expression by representational difference analysis of cDNA", Nucleic Acids Research, 1994, vol. 22, No. 25, pp. 5640–5648.

Suzuki, Yutaka et al., "Efficient isolation fo differentially expressed genes by means of a newly established method, 'EDS'", Nucleic Acids Research, 1996, vol. 24, No. 4, pp. 797–799.

Lisitsyn, Nikolai et al., "Cloning the Difference Between Two Complex Genomes", Science, vol. 259, Feb. 12, 1993, pp. 946–951.

Mathieu–Daude, Francoise, et al., "DNA rehybridization during PCR: the'$C_o t$ effect' and its consequences", Nucleic Acids Research, 1996, vol. 24, No. 11, pp. 2080–2086.

Hou, Ping, et al., "A simplified genomic subtractive procedure for isolating deleted sequences", Nucleic Acids Research, 1996, vol. 24, No. 11, pp. 2196–2197.

(List continued on next page.)

*Primary Examiner*—Kenneth R. Horlick

[57] ABSTRACT

The present invention relates to methods and kits for generating or analyzing nucleic acid populations or desired nucleic acid sequences based upon replication or amplification reactions. The invention comprises methods employing adaptors ligated to nucleic acids that preferentially permit replication or amplification of desired nucleic acid sequences or preferentially eliminate undesired nucleic acids from replication or amplification. The invention also comprises adaptors useful in the methods and in kits for replicating or amplifying nucleic acids. In one embodiment, the adaptors function to protect desired nucleic acids from cleavage by a restriction enzyme while other nucleic acids are cleaved. The protected, desired nucleic acids can then be preferentially replicated or amplified. Accordingly, the invention can be used for the amplification of desired nucleic acids and the effective removal of undesired nucleic acids from a population.

43 Claims, 14 Drawing Sheets

OTHER PUBLICATIONS

Padgett, Kerstien A., "Creating seamless junctions independent of restriction sites in PCR cloning", Gene, 168, pp. 31–35.

McClelland, Michael et al., "Effect of site–specific modification on restriction endonucleases adn DNA modification methyltransferases", Nucleic Acids Research, 1994, Vo. 22, No. 17, pp. 3640–3659.

Hampson, Ian N. et al., "Chemical cross linking substraction (CCLS): a new method for the generation of subtractive hybridisation probes", Nucleic Acids Research, vol. 20, No. 11, p. 2899.

Milner, Joel J., "A kinetic model for subtractive hybridization", Nucleic Acids Research, 1995, vol. 23, No. 1, pp. 176–187.

Kunkel, Louis M. et al., "Specific cloning of DNA fragments absent from the DNA of a male patient with an X chromosome deletion", Proc. Natl. Acad. Sci. USA, vol. 82, pp. 4778–4782, Jul. 1985.

Supplement 34 (1996) "PCR–Based Substractive cDNA Cloning", Sections 5.9.1–5.11.1, Ausubel, F.M., et al. (1989) Current Protocols in Molecular Biology, Greene Publishing Associates and Wiley–Interscience, New York.

Abstract of "PCR with 5–methyl–dCTP replacing dCTP", K.K. Wong et al., Nucleic Acids Res. 19: 1081–5 (1991).

Bjourson et al., Appl. Environ. Microbiol. 58(7), 2296–2301, 1992.

FIG. 1B

```
                        SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 17..18
        (D) OTHER INFORMATION: /note= " as noted in specification
            N throughout sequences is modified nucleotide,
            such as m5c: N is optionally modified nucleotide;

(xi) SEQUENCE DESCRIPTION: SEQ ID NO:1:

ACTACTTATC TATGTTNT                                                18

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

ACTACTTATC TATGTTNTNT                                              20

(2) INFORMATION FOR SEQ ID NO:3:

(i) SEQUENCE CHARACTERISTICS:
        (A) LENGTH: 20 base pairs
```

```
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

ACTTATCTAT GTTNTNTTNG                                                   20

(2) INFORMATION FOR SEQ ID NO:4:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

TAACTACTTA TCTATGTTNT NTTNGAAGAG GCAC                                   34

(2) INFORMATION FOR SEQ ID NO:5:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GTGCCTCTTC GA                                                           12

(2) INFORMATION FOR SEQ ID NO:6:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GTAGTGTAGG TCTACTAGNT                                                   20

(2) INFORMATION FOR SEQ ID NO:7:

(i) SEQUENCE CHARACTERISTICS:
          (A) LENGTH: 20 base pairs
          (B) TYPE: nucleic acid
          (C) STRANDEDNESS: single
          (D) TOPOLOGY: linear
```

(ii) MOLECULE TYPE: DNA (genomic)

(xi) SEQUENCE DESCRIPTION: SEQ ID NO:7:

AGTGTAGGTC TACTAGNTNT                                                20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

GTAGGTCTAC TAGNTNTTNG                                                20

(2) INFORMATION FOR SEQ ID NO:9:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GTAGTGTAGG TCTACTAGNT NTTNGAAGAG GACT                                34

(2) INFORMATION FOR SEQ ID NO:10:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

AGTCCTCTTC GA                                                        12

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

AGGTCTACTA GNTNTTNNNN                                                20

(2) INFORMATION FOR SEQ ID NO:12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

AGGTCTACTA GCTCTTCNNN GAAGAG                                         26

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CTCTTCNNNG AA                                                  12

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

NNNNNNNNNN NNNNNNNNCT CTTCN                                25

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:15:

NNNNNNNNNN NNNNNNNNCT CTTCNNNN                           28

(2) INFORMATION FOR SEQ ID NO:16:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

NNNNGAAGAG NN                                                  12

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TAACTACTTA TCTATGTTCT CTTCG                                25

(2) INFORMATION FOR SEQ ID NO:18:

(i) SEQUENCE CHARACTERISTICS:

```
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TAACTACTTA TCTATGTTCT CTTCGCAC                                    28

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GTGCGAAGAG AA                                                     12

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

NNNNNNNNNN NNNNNNNNNN NNNNN                                       25

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

NNNNNNNNNN NNNNNNNNNN NNNNNNNN                                    28

(2) INFORMATION FOR SEQ ID NO:22:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

NNNNNNNNNN NN                                                     12

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:23:

CTTAGCTAAC GTCATTAGCC TAGCT                                          25

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTTAGCTAAC GTCATTAGCC TAGCTCTGA                                      29

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TCAGAGCTAG GCT                                                       13

(2) INFORMATION FOR SEQ ID NO:26:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GTGCGAAGAG AACATAGATA AGTAGTTA                                       28

(2) INFORMATION FOR SEQ ID NO:27:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CAGAGCTACC CTAATGACGT TAGCTAAG                                       28

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TAACTACTTA TCTATGTTNT                                                20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ACTACTTATC TATGTTCTNT                                      20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

ACTTATCTAT GTTCTCTTNG                                      20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

ACTTATCTAT GTTNTNTTNG                                      20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GTAGTGTAGG TCTACTAGNT                                      20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

AGTGTAGGTC TACTAGCTNT                                      20

(2) INFORMATION FOR SEQ ID NO:34:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

GTAGGTCTAC TAGCTCTTNG                                                    20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GTAGGTCTAC TAGNTNTTNG                                                    20
```

METHODS AND ADAPTORS FOR GENERATING SPECIFIC NUCLEIC ACID POPULATIONS

RELATED APPLICATIONS

This application is a continuation-in-part of U.S. Ser. No. 08/775,993, filed Jan. 3, 1997, abandoned, which claims the benefit of U.S. Provisional Application No. 60/033,175, filed Dec. 13, 1996.

FIELD OF THE INVENTION

The present invention relates to methods and kits for generating or analyzing nucleic acid populations or desired nucleic acid sequences based upon replication or amplification reactions.

DESCRIPTION OF RELATED ART

In the related methods discussed herein, the nucleic acid sample containing or believed to contain one or more desired nucleic acids or the target nucleic acids is often referred to as the "tester" or "tracer." The nucleic acid sample which is believed to specifically lack the desired nucleic acid is referred to as the "driver." The reaction products of an amplification reaction are sometimes referred to as an "amplicon" or "representation." Hybrids formed after combining the tester and driver nucleic acid samples are denoted, for example, "driver:driver," "tester:driver," and "tester:tester." In this disclosure, nucleic acids refer to DNA, cDNA, RNA, and mRNA molecules, combinations thereof, or the like from any source, with or without modified nucleotides.

Scientists have employed procedures to separate and identify nucleic acid molecules from different sources for a variety of purposes. Nucleic acid libraries, for example, possess all or part of the genome or expressed sequences from a particular biological source. Certain libraries have proven valuable tools in deciphering the importance of, characterizing, and isolating nucleic acid sequences. However, isolating a desired clone from a library containing a million or more clones is both time consuming and labor intensive. The ability to extract a desired clone from a library involves selection of an appropriate library. For cDNA libraries, the source of the nucleic acids used to construct the library should contain the most copies of the desired clone compared to other available libraries. The number of copies of a desired clone in a library can be predicted by the characteristic expression of the desired nucleic acid in a biological source. Certain libraries, therefore, are enriched for the presence of certain nucleic acid sequences because of the source of the nucleic acids used to construct the library. Another way to enrich for rare nucleic acid species is to construct a subtracted library.

Subtraction libraries are produced through methods generally referred to as subtractive methods or subtractive hybridization methods. These methods generally rely on the hybridization of complementary nucleic acid strands from differing sources. A first source of nucleic acids (tester nucleic acids) is believed to comprise desired or target nucleic acids. A second source of nucleic acids (driver nucleic acids), generally the closest phenotype to the first source presumed to lack the desired or target nucleic acids, is used to "subtract" common and undesired nucleic acids through hybridization, followed by a separation of the hybridized nucleic acids from the non-hybridized nucleic acids. Thus, the subtraction library allows one to identify desired nucleic acids by their differential abundance in two cells or cell types.

There are numerous examples of the power of subtraction libraries. One skilled in the art can isolate sex-specific genes or DNA fragments (1); detect differences in gene expression; and detect differential gene expression in cells at different developmental stages, for example, distinguishing differentiated cells from stem cells, activated cells from their resting counterparts, and mutant cells from normal cells. For example, Lamar and Palmer (1) described a subtractive hybridization method to enrich for Y-chromosome specific genomic DNA. In this method, female genomic DNA (containing X chromosome DNA) was used to "drive" hybridization between existing strands of non-Y DNA in a sample of male genomic DNA, by physically separating the hybridized non-Y DNA from the single stranded Y DNA with hydroxyapatite chromatography. The non-Y DNA was subtracted via from the sample and Y-chromosome specific DNA was generated. Subtractive hybridization of cDNA with mRNA, or of cDNA libraries, has also been used to identify mRNAs responsible for certain developmental events (10). Subtractive hybridizations were also reported by Kunkel et al. (2) and Nussbaum et al. (3).

However, the methods described above employ physical separation techniques, which are designed to isolate sequences with a particular affinity to a substrate. For example, hydroxyapatite gel chromatography is used to separate double stranded nucleic acids from single stranded nucleic acids. As used in Lamar and Palmer (1), the double stranded nucleic acids are "subtracted" from the single stranded nucleic acids to produce a sample enriched in the unique single stranded nucleic acids. Thus, the physical separation techniques can enrich the population of particular nucleic acids believed to be present in a sample. The ability to increase the relative abundance of particular nucleic acids with respect to all other nucleic acids present in the library is, however, limited by the effectiveness of the physical separation technique.

In addition, subtraction hybridization is a technically difficult, time-consuming, and often either an impractical or unreliable procedure. The subtraction generally involves a physical separation method as noted above, such as hydroxyapatite chromatography (1) or streptavidin binding to biotin-labeled sequences. The efficiency of the physical separation process, both the binding and release, necessarily controls the degree of enrichment for a particular, desired sequence. Thus, while the subtraction hybridization methods yield the desired products (target nucleic acid) in certain applications, the limited degree of enrichment for unique and/or rare species precludes a universal or even general application. Furthermore, the technical demands of the physical separation step common to the substraction techniques created a need for improved methods to identify rare nucleic acids.

The introduction and use of the polymerase chain reaction (PCR) in library construction techniques attempted to address the problem of isolating a rare nucleic acid from a particular source. The amplification of nucleic acids in PCR theoretically results in an exponential increase of all the sequences present that are appropriately primed. Thus, even rare sequences would be present in a much higher absolute number following PCR. However, if all sequences in a sample are amplified, the relative abundance of a particular, rare sequence compared to the number of other sequences present does not change as a result of the PCR amplification. In order to specifically amplify a particular sequence, a primer specific for that sequence is required.

One effort to enrich for particular sequences or desired subsets of sequences is PCR-based subtractive cDNA cloning (15). However, this technique, which subjects the products of two separate and differing PCR amplifications (amplicons) to subtraction hybridization, employs the same physical separation step mentioned above. More specifically, a first amplified sample contains the desired or target nucleic acid (tester) and a second sample amplified does not (driver). During amplification of the driver, biotin-labeled nucleotides are incorporated into the reaction products (amplicons). After combining the products of the two amplifications and annealing complementary nucleic acids, the undesired hybrids which are formed are subtracted from the sample by a process involving the binding of streptavidin to the biotin-labeled nucleotides, followed by chemical extraction. Streptavidin will only bind to the hybrids containing driver nucleic acids, which contain biotin-labeled nucleotides, so hybrids of two tester nucleic acids (tester:tester) will not be subtracted. The degree of subtraction or enrichment will depend therefore on the efficiency of the extraction of the hybrids of driver nucleic acids.

Lisitsyn et al. introduced an adaptation of the PCR-based method when they described representational difference analysis (RDA) for genomic DNA (4). RDA utilizes PCR to enrich for unique species in one of the samples after hybridization and polymerization steps. RDA does not rely on physical separation methods. Instead, RDA uses two separate ligations of two different adaptors to enrich for unique species. After an initial PCR amplification of both tester and driver samples with a first adaptor, a second adaptor is attached to the ends of tester DNA but not the driver DNA. Then, after mixing the second adaptor-treated tester DNA with driver DNA, denaturing, hybridizing, and filling in overhanging ends, only double stranded tester DNA should amplify exponentially with PCR primers specific for the second adaptor sequences. In theory, the tester:driver hybrids should amplify linearly and the driver:driver hybrids should not amplify at all.

In order to be effective, RDA requires a reduced complexity in the starting material used (4, 5). To reduce the complexity, RDA generally employs a digestion of total genomic DNA with a six base pair-cutting enzyme and amplifying the digested DNA by PCR. A high proportion of the digested fragments do not fall within what Lisitsyn et al. defined as the amplifiable range of 150–1000 base pairs. Larger fragments are not amplified, reducing the complexity of the amplicon so that the final representation contains only about 2–10% of the total genome (12, 13). Of course, the representations of the PCR will not encompass the entire sequence information available in the genome. Consequently, desired sequences may not be represented in the subtracted library while undesired species may be represented in the subtracted library.

RDA has been applied to cDNA subtraction by Hubank and Schatz (5). The method is very similar to RDA described by Lisitsyn et al., with cDNA being used as the starting material instead of genomic DNA. As with RDA, there are two adaptor ligation steps. The method is designed so that only tester:tester hybrids contain the PCR primer binding sites on both ends of the strands of DNA, and thus are the only species that are exponentially amplified. In contrast to the complexity of genomic RDA, a population of cDNA derives from some 15,000 different genes in a typical cell and represents only about 1–2% of the total genome (14). Therefore, RDA can apparently be applied to cDNA without the need to first reduce the complexity.

Hou et al. describe a recent attempt to address the problems of complexity in genomic PCR-based methods and, in addition, include the entire genome in the method (6). This method involves identifying deleted sequences in a particular genome. It is an abbreviated version of RDA, in which certain steps of RDA are omitted, such as the initial preparation of driver representations or amplicon and the single-stranded nuclease step (6). Instead, Hou et al. sonicate genomic DNA to produce driver DNA. This method, in its current form, is likely to be useful for techniques using genomic DNA and not cDNA. Producing large or sufficient amounts of DNA driver will require an initial amplification step, in most instances. Moreover, since the introns contained in genomic driver can cause problems during the priming step of RDA, it is unclear how successful the method will be when applied in general, as opposed to the identification of deleted sequences by Hou et al.

In addition to the above drawbacks, RDA only selects for the most abundant target sequences in the tester or tracer population. This phenomena results from the "kinetic enrichment" phenomenon associated with the procedure (4). Kinetic enrichment involves a hybridization step that is too short to allow a relatively rare tester:tester hybrid to form. The unhybridized rare nucleic acids will then amplify only linearly or will be digested by a single stranded nuclease step in the RDA procedure. Linear amplification occurs when there is only one strand to act as a template for amplification. Exponential amplification involves the amplification of two complementary strands. Abundant nucleic acids within the population will form tester:tester hybrids in a shorter period of time and at a higher frequency than rare nucleic acids. Consequently, the more abundant nucleic acids will have a higher probability of subsequent exponential amplification than the rare nucleic acids. The linearly amplified rare nucleic acids, often the desired target, will effectively become lost from the amplified population.

Another drawback of RDA is the importance of an appropriate concentration ratio of driver to tester nucleic acid. For example, even if a desired target is not lost from the population due to kinetic enrichment, it is amplified exponentially along with all of the other tester:tester hybrids in the population. The other tester nucleic acids must somehow be removed in order to identify the desired target. Undesired nucleic acids in the tester population (i.e., non-target nucleic acids) are removed with driver only in linear proportion to the concentration of driver nucleic acid used in the subtractive hybridization. That is, if driver is present in 100 fold excess, then $\frac{1}{100}$ of the non-target nucleic acids in the tester population escape hybridization with driver. These non-target nucleic acids then amplify exponentially along with the target nucleic acids in the tester population. Thus, enrichment for the desired target is limited by the use of an appropriate driver:tester nucleic acid ratio. Multiple rounds of hybridization and subtraction are generally needed to effect desired enrichments. As noted in prior discussions (15), 5–20 repeated subtractions are sometimes required and RDA procedures also require repeated subtractions. The repeated subtractions are obviously quite cumbersome and time-consuming.

Yet another drawback of RDA comes from the linear amplification of undesired nucleic acids, such as tester:driver hybrids, and the concomitant reduction in amplification of desired target nucleic acids. If a particular, undesired nucleic acid in both the tester and driver samples is in relative abundance, it is amplified linearly during RDA. During this linear amplification, it is competing for primers, enzyme, and nucleotides with the other nucleic acids present. This is especially problematic very early on in the amplification process, when such undesired nucleic acids are in great abundance relative to the target. This can limit the amplification efficiency of the desired nucleic acids. Moreover, linear amplification of the undesired tester:driver hybrids results in a concentration of such hybrids which are higher than desired following the PCR process.

Thus, RDA, while very powerful, still has certain drawbacks. There are limitations in the applicability of its use, such as in the complexity of the samples permitted. Also, RDA requires two separate ligation procedures with two different adaptors. And, RDA is most effective when the desired nucleic acid is relatively abundant in the sample. Clearly, alternative methods for generating enriched nucleic acid samples are needed.

Suzuki et al. have attempted to address some of the drawbacks of RDA with a method referred to as ESD, (equalization of cDNAs, subtractive hybridization, and differential display (7)). The method attempts to equalize or normalize the content of the tester and driver samples by performing an initial subtraction with the target-containing tester cDNA. A physical subtraction hybridization step is relied on, with tester cDNA acting as "driver," to effectively equalize the contents of each of the cDNA populations. PCR is performed subsequent to the equalization. This, in theory, helps to ensure the exponential amplification of nucleic acids that were rare in the starting cDNA population and reduce the relative abundance of common, undesired nucleic acids by avoiding the kinetic enrichment problem.

While apparently advantageous, ESD is primarily a physical subtraction method. Both the above-mentioned hydroxyapatite gel chromatography and biotin-streptavidin procedures were used. The mere reliance upon the physical subtraction steps makes ESD technically challenging and introduces the drawbacks indicated above. In addition, PCR is used only to regenerate the non-subtracted population. The exponential enrichment possibilities of PCR or any amplification reaction does not itself play a role in increasing the relative abundance of desired nucleic acid during the ESD procedure.

While other PCR-based techniques have been employed for enriching desired nucleic acids as in the methods for generating subtractive libraries, each of these methods also has its drawbacks. One method, the "chemical cross-linking subtraction" method (32), specifically requires a mRNA-cDNA hybrid in order to subtract nucleic acids. This requirement necessarily limits the method's application to situations where both a mRNA and a cDNA sample are available for use. Another method, discussed in Riley et al. (33), employs a "vectorette" adaptor in PCR. However, the method requires partial sequence information, which is not always known. Thus, the method of Riley et al. is limited to situations where partial sequence information is known. One final method, discussed in Chenchnik et al. (34), involves a "pan-like" hybridization structure that is used to prevent certain nucleic acids from being amplified. In effect, the method relies on the efficiency of one type of hybridization over another in order to selectively suppress amplification of certain nucleic acids. It's application is limited in that it amplifies only the DNA common to two samples and not those unique to one sample.

Thus, there remains a need in the art for new and improved methods to generate specific populations of nucleic acids as used, for example, in producing subtracted libraries. By providing methods for preferentially replicating or amplifying nucleic acids, the disclosed invention fulfills those needs. The invention represents a significant advancement over previous methods because, inter alia, physical separation techniques are not required, only user friendly laboratory procedures are used, and the preferential replication and amplification of desired nucleic acids is simplified and more efficient.

SUMMARY OF THE INVENTION

The invention comprises methods employing adaptors ligated to nucleic acids that preferentially permit replication or amplification of desired nucleic acid sequences or preferentially eliminate undesired nucleic acids from replication or amplification. In one embodiment, the adaptors function to protect desired nucleic acids from cleavage by a restriction enzyme while other nucleic acids are cleaved. The protected desired nucleic acids can then be preferentially replicated or amplified. In another embodiment, the adaptors function to prevent or interfere with the replication or amplification of undesired nucleic acids when modified nucleotides are incorporated into undesired nucleic acids. For example, the modified nucleotides may comprise ligands or cross-linking agents which function to substantially interfere with replication or amplification reactions. Accordingly, the methods of the invention result in the replication or amplification of desired nucleic acids and the effective removal of undesired nucleic acids from a population.

The methods of the invention are particularly useful for generating nucleic acid libraries, identifying the presence or absence of certain nucleic acid sequences in a sample, replicating or amplifying desired nucleic acids, or enriching the presence of desired nucleic acids in a sample.

In accordance with the invention, methods are provided for preferentially replicating or amplifying one or more desired nucleic acids. Generally, one or more selected adaptors are ligated to the ends of nucleic acids in a tester nucleic acid sample and a driver nucleic acid sample. This results in adaptor:tester nucleic acid complexes and adaptor:driver nucleic acid complexes, where an "adaptor:nucleic acid complex" is a nucleic acid to which a selected adaptor has been operably ligated. After producing the complexes, the adaptor:tester nucleic acid complexes and adaptor:driver nucleic acid complexes are appropriately combined, under first denaturing and then annealing conditions, so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes. Thereafter, a reagent capable of substantially preventing replication of all but double-stranded adaptor:tester nucleic acid complexes is added. The double-stranded adaptor:tester nucleic acid complexes can then be preferentially replicated or amplified by a reaction known in the art.

Preferably, the methods employ a selected adaptor comprising a cleavage site, such as a restriction enzyme recognition site. Thus, in certain preferred embodiments, the reagent that substantially prevents replication of all but double-stranded adaptor:tester nucleic acids is a restriction enzyme. The methods may also employ an extension step, whereby a selected primer is utilized with adaptor:tester nucleic acid complexes and/or adaptor:driver nucleic acid complexes to generate complementary strands of the complexes. Modified nucleotides may optionally be added to the extension step so that they are incorporated into the complementary strand of the adaptor:tester or adaptor:driver nucleic acid complexes so as to permit the preferential replication or amplification of double-stranded adaptor:tester nucleic acid complexes. The adaptors and primers employed in the methods may also comprise modified nucleotides.

The methods of the invention also include embodiments where a plurality of adaptors is selected for use. In addition to comprising a restriction enzyme recognition site, some of these selected adaptors may comprise one or more regions of non-homologous nucleotides so that when adaptor:tester and adaptor:driver nucleic acid complexes are combined to anneal and form double-stranded nucleic acids, at least a portion of one of the selected adaptors will not hybridize to another selected adaptor. A reagent, such as a restriction enzyme corresponding to the recognition site of an adaptor or an enzyme that preferentially cleaves at double-stranded or single-stranded sites, can be selected and used so that certain adaptor:nucleic acid complexes are preferentially cleaved, thus substantially preventing replication or amplification of undesired nucleic acids.

For example, preferred methods for preferentially replicating one or more desired nucleic acids comprise ligating a first set of selected adaptors to the ends of tester nucleic acids, thereby producing adaptor:tester nucleic acid complexes, and ligating a second set of selected adaptors to the ends of driver nucleic acids, thereby producing adaptor:driver nucleic acid complexes. The second set of selected adaptors comprises a site recognized by a reagent capable of substantially preventing replication of double-stranded adaptor:driver nucleic acid complexes and includes a region which is non-homologous to the first set of selected adaptors. After combining the adaptor:tester nucleic acid complexes with the adaptor:driver nucleic acid complexes to produce double-stranded hybrid nucleic acids as described above, a selected reagent is added that is capable of substantially preventing replication of double-stranded adaptor:driver nucleic acid complexes. Preferably, this is accomplished by a restriction enzyme which recognizes or cleaves a site in the second set of adaptors. A single stranded nuclease capable of substantially cleaving single stranded nucleic acid complexes is thereafter added to remove unhybridized adaptor sequences of double-stranded adaptor:tester/adaptor:driver nucleic acid complexes. The resulting double-stranded adaptor:tester nucleic acid complexes can then be preferentially replicated or amplified.

In certain aspects, the methods of this invention are directed at providing simplified methods to create normalized and subtractive nucleic acid populations. By providing methods to generate powerful new libraries, the invention facilitates the discovery of new genes and helps to uncover pathways involved in various disease states. Researchers can screen such libraries directly or use them in subtractive protocols to produce further libraries for use in the art.

In certain preferred embodiments of the invention, methods are provided for normalizing the nucleic acid contents of a sample. These embodiments may include methods for subtractive hybridization with PCR-based techniques and can be used in a variety of amplification reaction-based techniques suited for constructing highly enriched nucleic acid libraries. Additionally, the invention is useful to create new or enrich existing nucleic acid libraries to more efficiently identify desired nucleic acids.

The methods of the invention are further directed at generating desired nucleic acids believed to be present in a particular cell, organism, or other source of nucleic acid. Populations of nucleic acids enriched for the presence of desired nucleic acids can also be generated. The nucleic acids and the subsets of nucleic acids produced can themselves be used as probes in a purified form. Additionally, the sequence information contained in such nucleic acids and subsets can itself, either as a collection of clones, purified molecules, or as a nucleotide sequence, be useful for research applications. Furthermore, desired nucleic acids or populations can be incorporated into appropriate vectors to produce libraries. One skilled in the art is familiar with many examples of appropriate vectors and the use of these vectors for producing libraries (37).

The invention further provides methods and kits for research or in diagnostic applications to identify the presence or absence of certain nucleic acids in a sample. One skilled in the art is familiar with amplification reaction-based assays and kits, as exemplified in the listed references (17, 21) and others known in the art, as well as nucleic acid replication-based assays, such as primer extension reactions (25).

Adaptors for nucleic acid replication and amplification techniques, as well as primers that generally anneal to the adaptors, are well known in the art. However, the design and use of the adaptors disclosed herein, in combination with a replication or amplification reaction, provides a novel, simplified, and generally applicable reagent for preferentially directing the various replication and amplification reactions known in the art to desired nucleic acids. Thus, the invention specifically includes the disclosed adaptors, with or without the appropriate modifications and annealing primers, functioning or capable of functioning in the disclosed methods. While preferred adaptor sequences are shown in the Detailed Description below, one skilled in the art having the benefit of this disclosure will appreciate that the present invention is not limited to the sequences specifically set forth herein.

DESCRIPTION OF THE FIGURES

Throughout these figures and by convention, double-stranded nucleic acid is represented as two horizontal lines, either solid or broken. The strand represented by the top line has its 5' end to the left and 3' end to the right. The strand represented by the bottom line has its 3' end to the left and 5' end to the right. Also, the designation (') indicates a complementary strand of the DNA, which may not be the full length of its complement. The designation (m) represents a strand, or primer, or synthesized sequence containing one or more methylated nucleotide bases, such as methyl-dCTP. The numbers followed by an (X) in the figures represent the relative abundance of the specified nucleic acids.

FIGS. 1A–1C: Switched adaptor subtraction employing cDNA in the original samples. FIG. 1A: Two samples, tester containing target cDNA (T1, T2, T3) and driver cDNA (D1, D2, D3), are prepared by cleaving with a restriction enzyme R and ligating adaptors A and B to the ends, followed by extending the 3' ends. The shorter strands of the originally ligated adaptors (A' and B') are displaced as they do not contain 5' phosphate groups. Adaptors A and B can be the same or different adaptors. The adaptors A and B depicted comprise a restriction enzyme cleavage site, such as the site for Eam 1104I cleavage, and can be the adaptors A and B described in the Detailed Embodiments below. FIG. 1B: Each sample is separately amplified, but only the tester sample is amplified with 5-methyl-dCTP nucleotides and methylated primers. The two samples are combined by mixing followed by treatment under appropriate denaturing and annealing conditions. Some of the possible hybrids and single-stranded nucleic acids that form are depicted at the bottom of the figure.

FIG. 1C: The hybrids and single-stranded nucleic acids are put in contact with Eam 1104I and a single-stranded nuclease. The first box depicts hybrids where Eam cleaved in the adaptor sequence, resulting in the elimination of the primer binding site. These hybrids cannot be amplified. The second box depicts single-stranded nucleic acids that are cleaved by the single-stranded nuclease. These single-stranded nucleic acids are amplified. The third box depicts target:target hybrids containing the A and B adaptor sequences. These hybrids are amplified in an amplification reaction employing primers for the A and B adaptor sequences. If required, the subtraction cycle is repeated. The resulting amplified nucleic acids are incorporated into an appropriate vector, such as pCR Script™ to generate a library of preferentially amplified nucleic acids for commercial purposes and further research and development.

FIG. 2A: A sample for normalization is prepared by cleaving with a restriction enzyme R and ligating adaptors A and B to the ends. The 3' ends are extended, displacing the A' and B' strands, as in FIG. 1.

FIG. 2B: The sample is then amplified using primers for the A and B adaptor sequences. Hybrids, depicted as T1:T1' to T6:T6' with the attached adaptor sequences, result, which are then subjected to denaturing and annealing conditions. The most abundant sequences present will form double-stranded hybrids while the least abundant sequences will not.

FIG. 2C: A restriction enzyme, such as Eam 1104I, will cleave hybrids containing the adaptor sequence, the most abundant sequences. The first box depicts the highly abundant cDNA sequences with adaptor sequences removed as a result of the cleavage. These sequences will not be amplified. The second box depicts the lower abundant cDNA sequences with intact adaptor sequences. These sequences can be amplified with primers for the A and B adaptor sequences. A small percentage of the high abundant sequences will also remain single-stranded (not shown) and will be amplified as well. The result is a population of nucleic acids wherein the abundance of each different nucleic acid sequence is normalized. The method can be repeated to further normalize the sample.

Adaptor pairs are ligated to the two populations of nucleic acids. The adaptor pairs typically have a nucleotide strand (A) and a nucleotide strand (A') that is complementary to the most 3' bases on strand A. Only one primer, with the same polarity as strand A, is used for initial PCR amplification of tester and driver. However, the primer is methylated in the tester sample reaction and methylated dCTP is added to the initial tester amplification reaction. The primer in the driver sample is not methylated and methylated nucleotides are not added to the driver amplification reaction. Following mixing of the tester and driver amplicons, cleavage with Eam, and optionally a single-stranded nuclease treatment, another amplification is performed with the primer A, which is not methylated. Only certain hybridization species that would be present following mixing are shown and some complementary pairs have been left out to avoid redundancy. The target sequence, T3, amplifies exponentially. All other nucleic acids amplify either linearly or not at all.

Figure 4A:
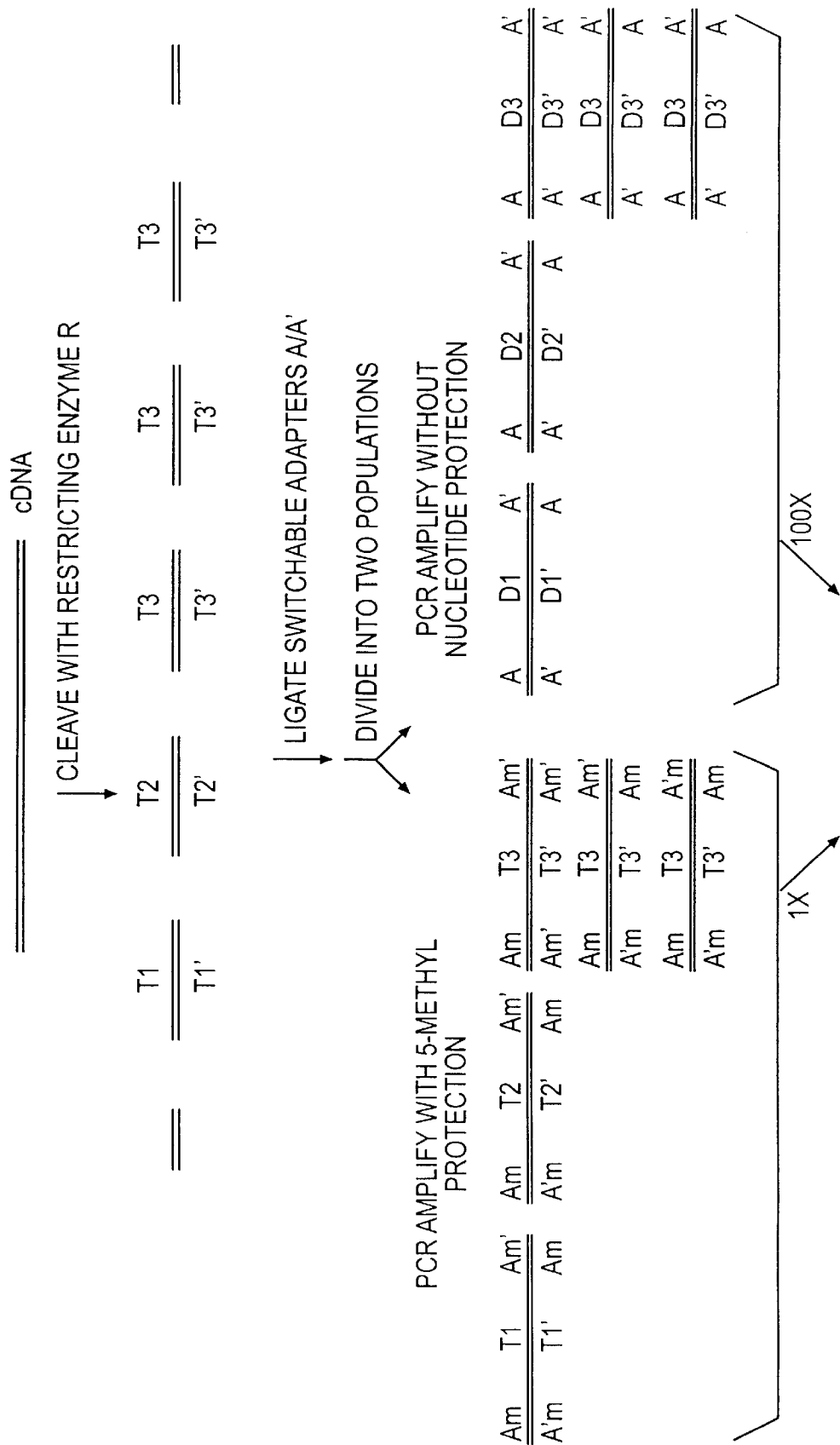
Figure 4B:
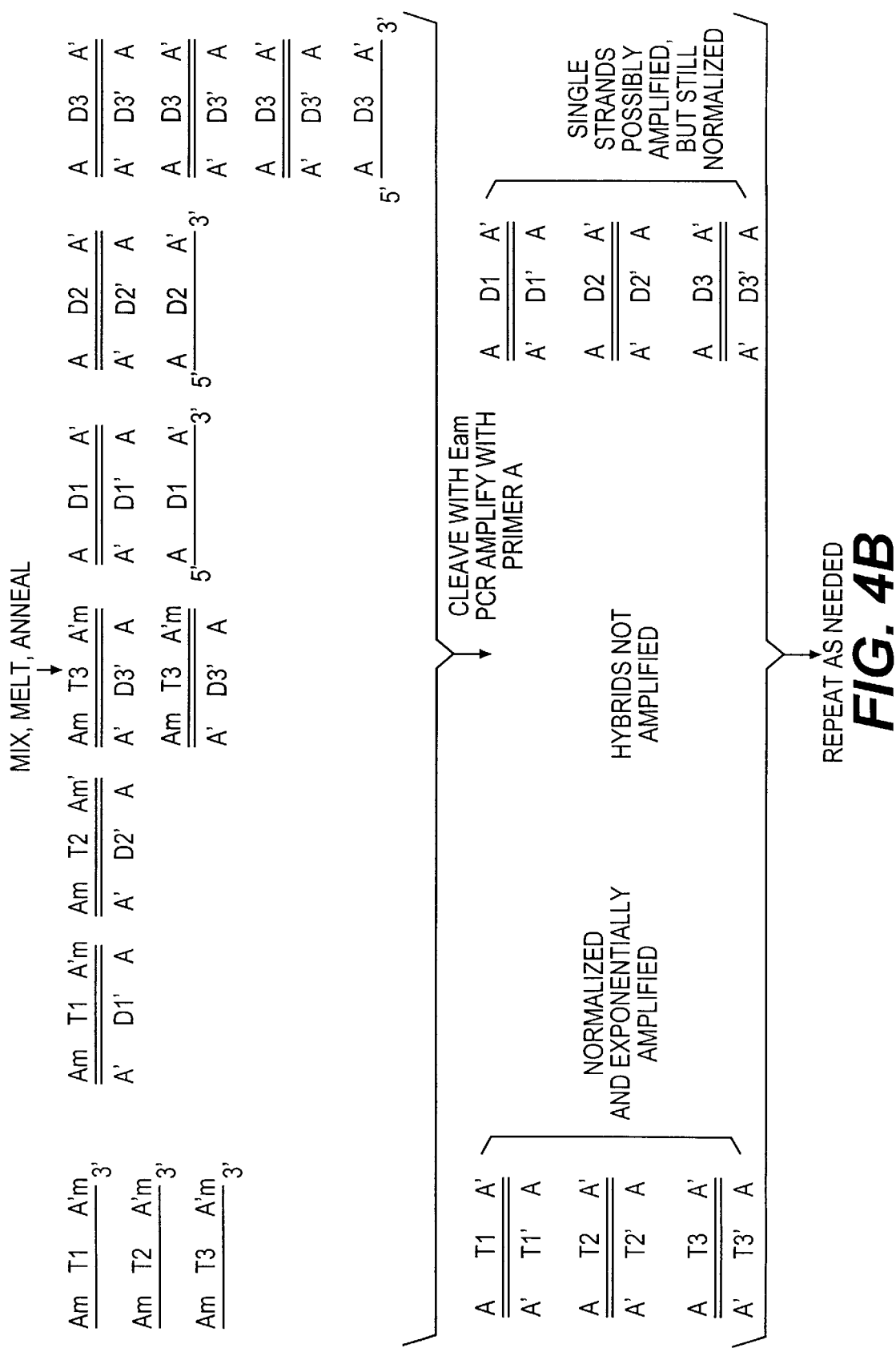

FIG. 4: An general outline of cDNA normalization. Here, three nucleic acids are shown, two have sequences present in low abundance (T1 and T2) and one in high abundance (T3). A first amplification is performed on a divided, cleaved sample of the starting cDNA population, as indicated. After mixing 1 part tester (T) amplicon with 100 parts of driver (D) amplicon, melting, and annealing, complementary pairs are formed between the T and D nucleic acids, shown at right. Again, not all possible complementary pairs have been depicted. The non-annealed tester sequences are shown toward the left. While some strands of nucleic acid T3 may remain single stranded, most will end up paired with driver strands D'3 (and strand T'3 will pair with strands D3—not shown). Unpaired driver strands are shown toward the right.

Figure 5A:
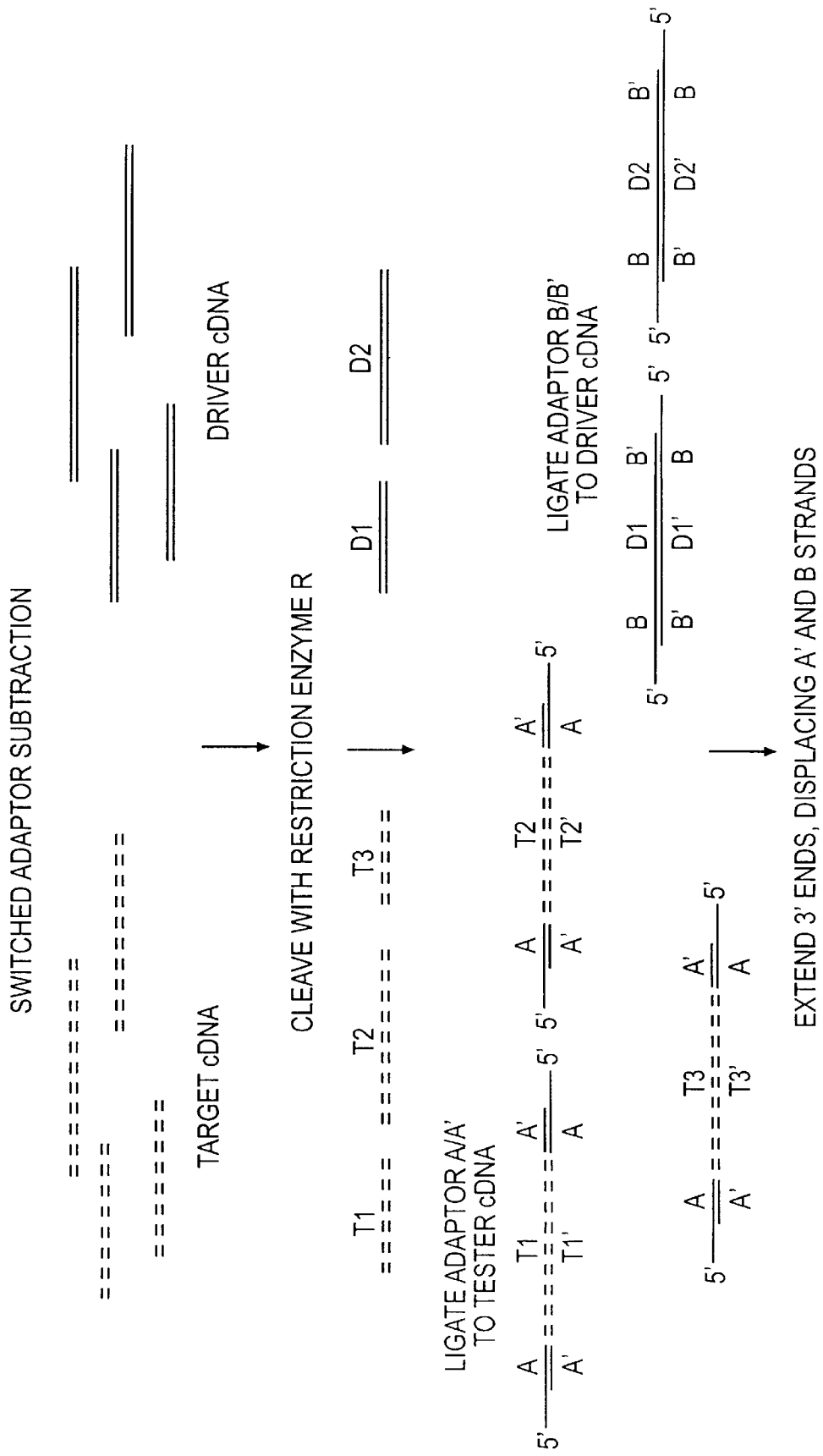
Figure 5B:
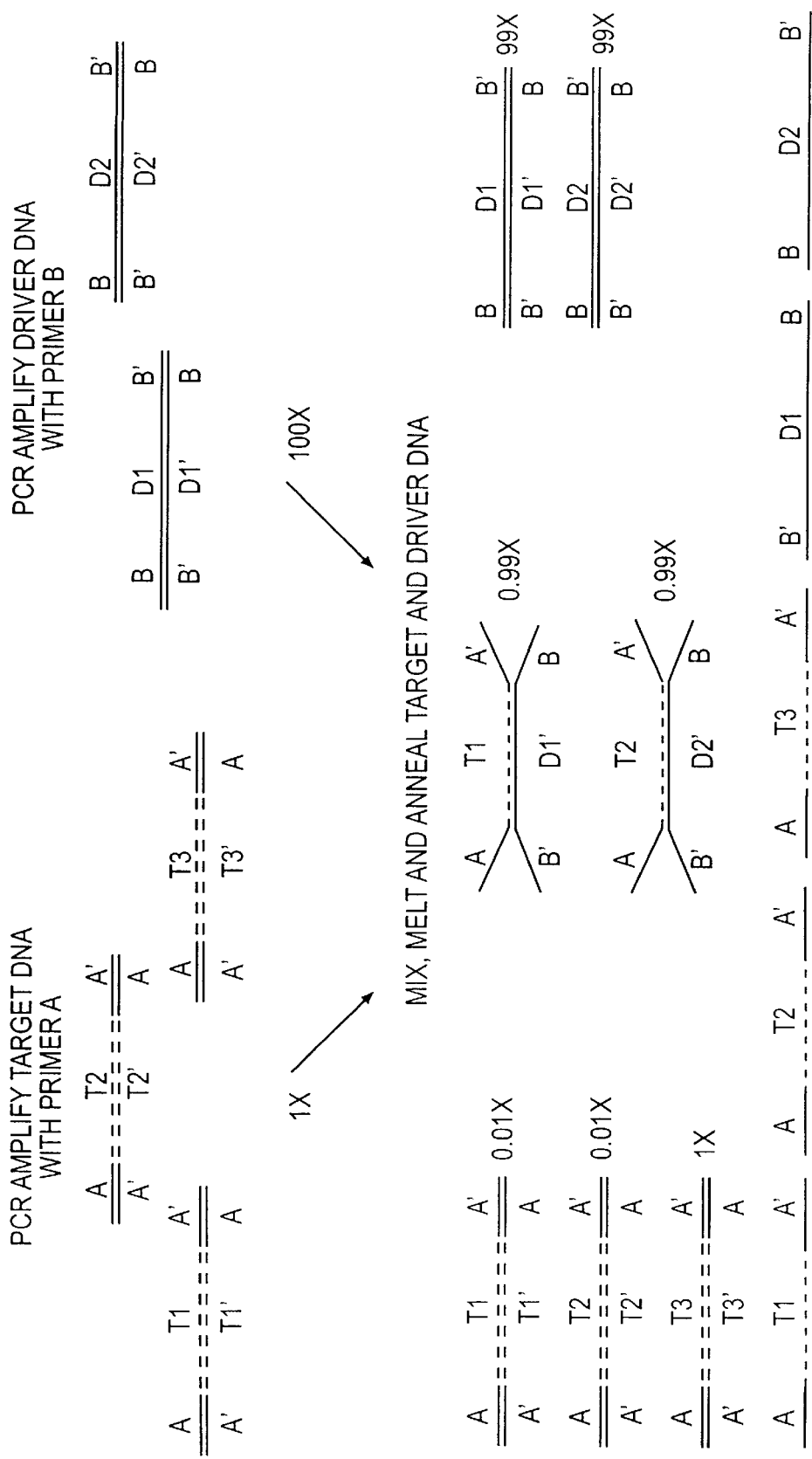
Figure 5C:
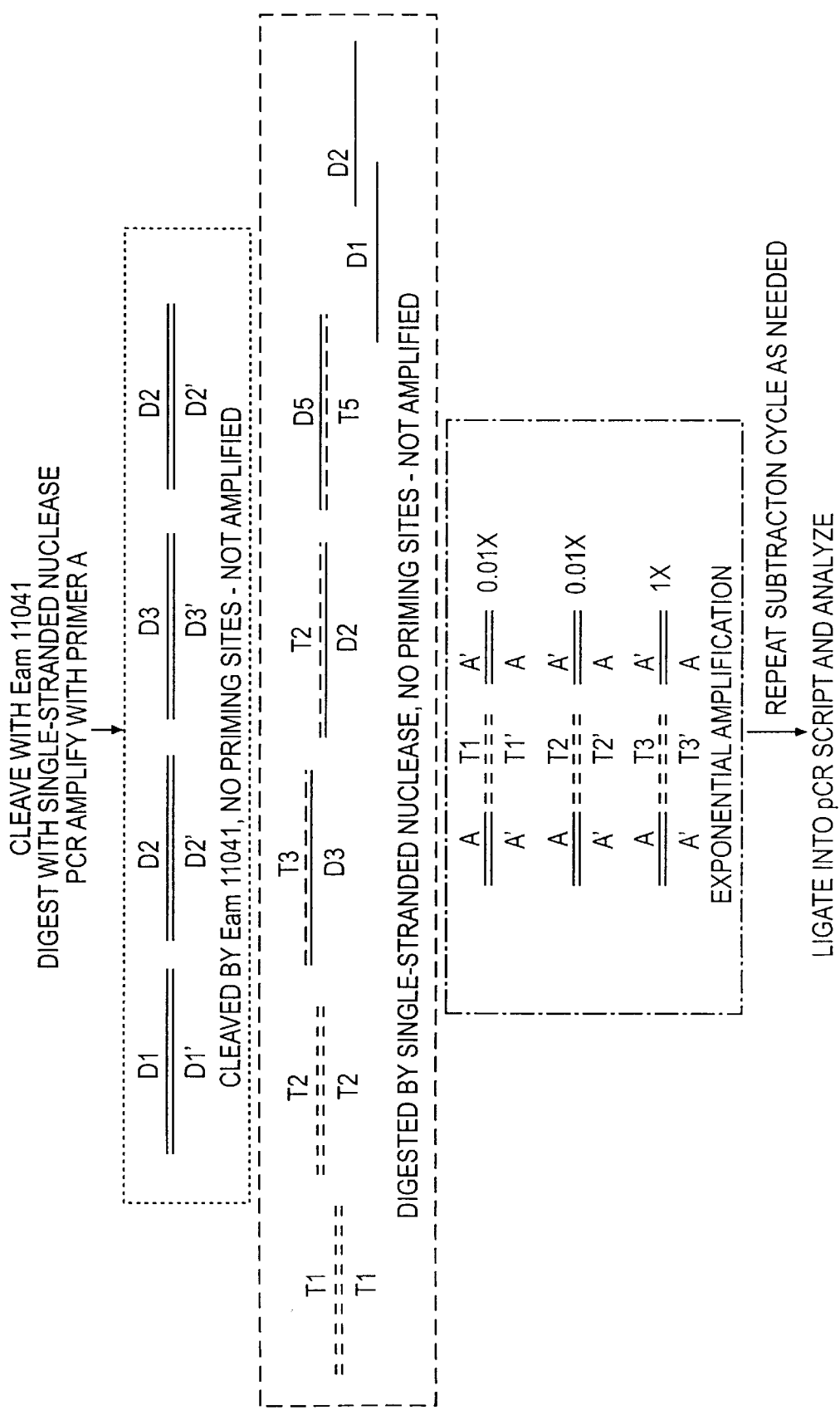

FIGS. 5A–5C Switched adaptor subtraction with non-homologous adaptors selected.

Figure 1A:
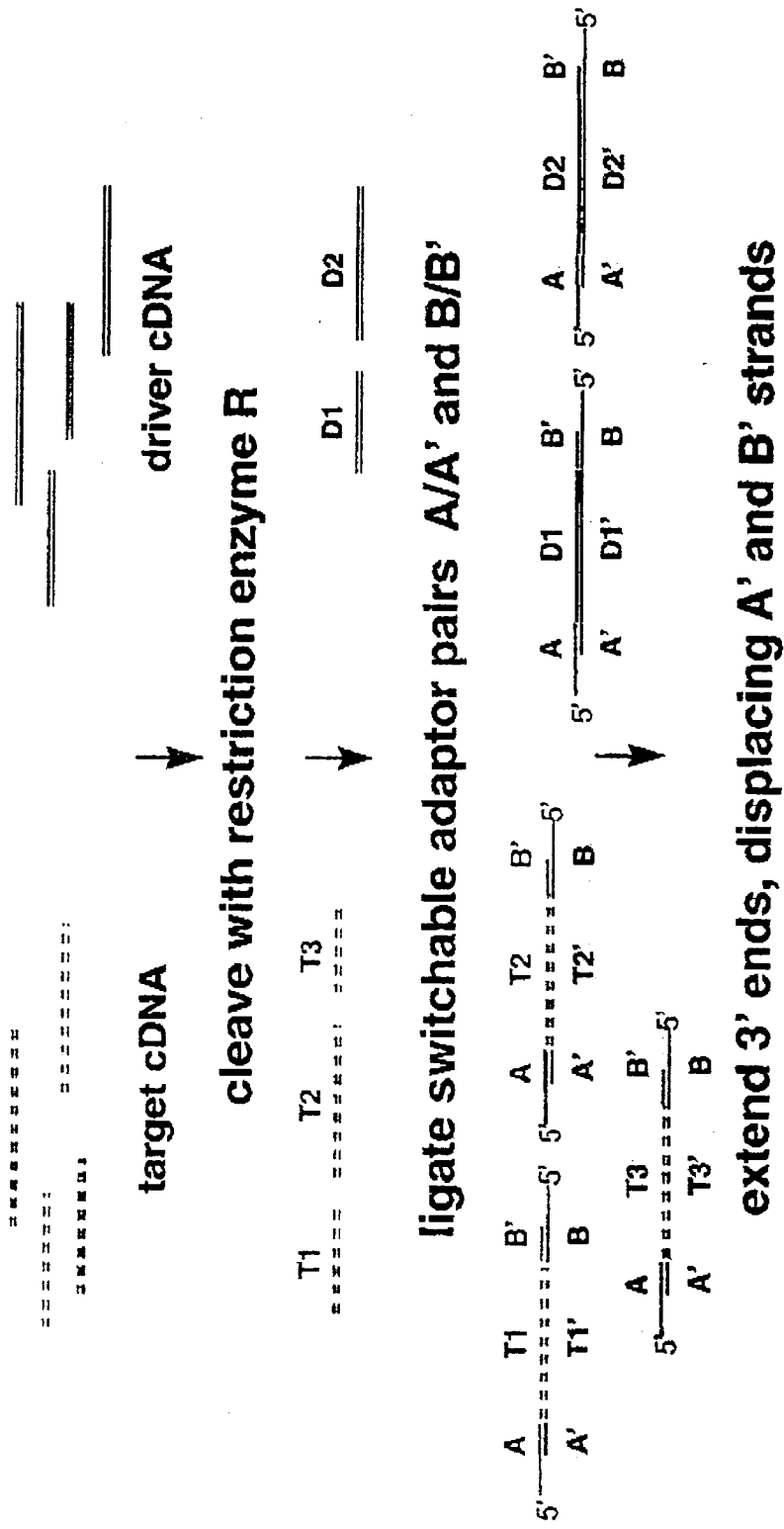

FIG. 5A: As indicated in the description of FIG. 1A except that only adaptors A and A' are ligated to tester and only adaptors B and B' are ligated to driver.

FIG. 5B: Each sample is separately amplified. The two samples are combined by mixing followed by treatment under appropriate denaturing and annealing conditions. Some of the possible hybrids and single-stranded nucleic acids that form are depicted at the bottom of the figure. The two double-stranded hybrids in the middle contain adaptors A and B or the complementary sequence which are non-homologous to each other and, thus, are shown to be not hybridized by the unpaired ends.

FIG. 5C: The hybrids and single-stranded nucleic acids are put in contact with Eam 1104I and a single-stranded nuclease. The first box depicts hybrids where Eam cleaved in the adaptor sequence, resulting in the elimination of the primer binding site. These hybrids cannot be amplified. The second box depicts single-stranded nucleic acids that are cleaved by the single-stranded nuclease. These single-stranded nucleic acids are cleaved and not amplified. The third box depicts target:target hybrids containing the A adaptor sequences. These hybrids are amplified in an amplification reaction employing primers for the A adaptor sequences. The resulting amplified nucleic acids can be incorporated into an appropriate vector, such as pCR Script™ to generate a library of a preferentially amplified nucleic acids for commercial purposes and further research and development.

Figure 6:
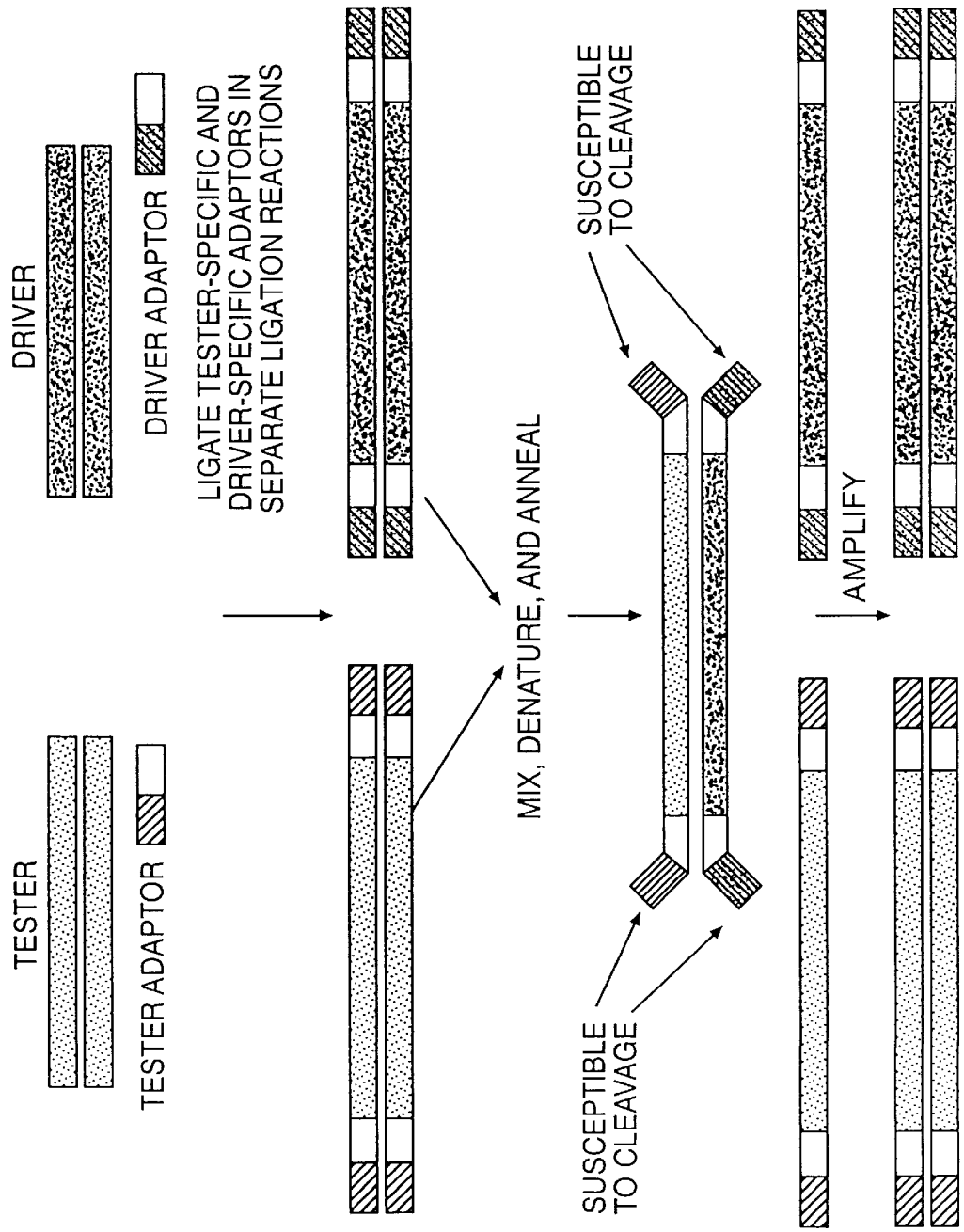

FIG. 6: A particular embodiment for preferential replication of single-stranded nucleic acids. The driver and tester adaptors, which differ in sequence, comprise (1) a non-homologous region (darker) which permits the selective replication or amplification of either tester or driver nucleic acids using selected primers therefor, and (2) a homologous region (lighter) having a recognition site for a reagent capable of substantially preventing replication or amplification of double-stranded nucleic acids. The adaptors are ligated to tester and driver samples. The resulting adaptor:tester and adaptor:driver nucleic acid complexes are shown in the middle of the figure. After combining by mixing, denaturing and annealing, double-stranded hybrid adaptor:nucleic acid complexes are formed. As indicated, the double-stranded adaptor region contains a site recognized by the reagent capable of substantially preventing replication or amplification of double-stranded nucleic acid complexes (circled region "susceptible to cleavage"). That site may be a restriction enzyme recognition site capable of being cleaved by a restriction enzyme when the site is double-stranded, but substantially incapable of being cleaved when the site is single-stranded. The single-stranded adaptor:nucleic acid complexes at the bottom are then replicated or amplified. Optionally, a primer or primers specific for the tester adaptor or driver adaptor can be used to preferentially replicate or amplify single-stranded adaptor:tester or single-stranded adaptor:driver nucleic acid complexes.

DETAILED DESCRIPTION AND SPECIFIC EMBODIMENTS OF THE INVENTION

Part I of this section contains a summary of certain preferred embodiments of the invention. Part II sets forth certain important concepts of the invention and certain selected adaptors suitable for use in the invention, and continues with certain, non-limiting definitions and general considerations applicable to the invention. Part II also includes descriptions of certain alternative embodiments of the invention. Part III sets forth further specific, detailed embodiments and examples. The Summary of the Invention section, above, also describes alternative embodiments of the invention. This section, therefore, should not be read to limit the scope of the embodiments considered to be a part of the invention.

I. Summary of Certain Preferred Embodiments of the Invention

In accordance with the invention, methods are provided for preferentially replicating or amplifying one or more desired nucleic acids. Generally, a selected adaptor or adaptors is ligated to the ends of nucleic acids in a tester nucleic acid sample and a driver nucleic acid sample. This results in adaptor:tester nucleic acid complexes and adaptor:driver nucleic acid complexes, where an "adaptor:nucleic acid complex" is a nucleic acid to which a selected adaptor has been operably ligated. After producing the complexes, the adaptor:tester nucleic acid complexes and adaptor:driver nucleic acid complexes are appropriately combined, under first denaturing and then annealing conditions, so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes. Thereafter, a reagent capable of substantially preventing replication of all but double-stranded adaptor:tester nucleic acid complexes is added. The double-stranded adaptor:tester nucleic acid complexes can then be preferentially replicated or amplified by a reaction known in the art.

Preferably, the methods employ a selected adaptor comprising a cleavage site, such as a restriction enzyme recognition site. In certain preferred embodiments, the reagent that substantially prevents replication of all but double-stranded adaptor:tester nucleic acid complexes is a restriction enzyme.

The methods may also employ an extension step, whereby a selected primer is utilized with adaptor:tester nucleic acid complexes and/or adaptor:driver nucleic acid complexes to generate complementary strands of the complexes. The selected primer of the extension step may comprise modified nucleotides and modified nucleotides may optionally be added to the extension step so that they are incorporated into the complementary strand of the adaptor:tester or adaptor:driver nucleic acid complexes.

In the methods employing an extension step with a selected primer comprising a modified nucleotide and/or the incorporation of modified nucleotides into complementary strands of adaptor:nucleic acid complexes, the modified nucleotides may function to substantially protect double-stranded adaptor:tester nucleic acid complexes from restriction enzyme cleavage. Alternatively, the modified nucleotides may function to substantially permit restriction enzyme cleavage of all but double-stranded adaptor:tester nucleic acid complexes. Accordingly, one skilled in the art having the benefit of this disclosure will appreciate that modified nucleotides may be selected so as to substantially prevent or permit restriction enzyme cleavage depending upon the adaptors and particular restriction enzyme selected for use.

In combination with the methods of the invention employing an extension step, a variety of adaptors may be selected, which comprise restriction enzyme recognition sites, for use with a selected restriction enzyme. Generally, restriction enzyme recognition sites comprise two complementary strands. Adaptors may be selected wherein they comprise one of the following types of recognition sites: (1) a site where one strand lacks a specific nucleotide base present in the complementary strand and the presence of a selected modified nucleotide protects against cleavage by the restriction enzyme: (2) a site recognized by a restriction enzyme capable of cleavage when a selected modified nucleotide is present in either strand but substantially incapable of cleavage when a selected modified nucleotide is present in both of the strands; (3) a site recognized by a restriction enzyme substantially incapable of cleavage when a selected modified nucleotide is present in either of the strands: or (4) a site recognized by a restriction enzyme capable of cleavage when a selected modified nucleotide is present in either one or both of the strands but substantially incapable of cleavage when a selected modified nucleotide is not present in either of the strands.

Accordingly, various alternative embodiments, methods are provided for preferentially replicating one or more desired nucleic acids, such methods comprise preparing tester nucleic acids and driver nucleic acids. One or more selected adaptor or adaptors of the invention are thereafter ligated to the ends of tester nucleic acids and driver nucleic acids, thereby producing adaptor:tester nucleic acid complexes and adaptor:driver nucleic acid complexes. The adaptor:tester nucleic acid complexes or adaptor:driver nucleic acid complexes are extended with a selected primer and a selected modified nucleotide. The adaptor:nucleic acid complexes are combined to produce double-stranded hybrid nucleic acids as described above. A reagent capable of substantially preventing replication of all but double-stranded adaptor:tester nucleic acid complexes is thereafter added. Double-stranded adaptor:tester nucleic acid complexes can then be preferentially replicated.

The present invention further provides embodiments where amplification is utilized and either adaptor:tester nucleic acid complexes or adaptor:driver nucleic acid complexes are amplified with a selected primer and a selected modified nucleotide. In one preferential amplification method of the invention, adaptor:tester nucleic acid complexes and adaptor:driver nucleic acid complexes are produced as described above. The adaptor:tester nucleic acid complexes are amplified with a first set of nucleotides and a first selected primer, while adaptor:driver nucleic acid complexes are amplified with a second set of nucleotides and a second selected primer. Either the first primer or the second primer comprises at least one modified nucleotide. After combining the adaptor:tester nucleic acid complexes and the adaptor:driver nucleic acid complexes to produce double-stranded hybrid nucleic acids, a reagent capable of substantially preventing amplification of all but double-stranded adaptor:tester nucleic acid complexes is added. The double-stranded adaptor:tester nucleic acid complexes can then be preferentially amplified.

In a particularly preferred method for preferentially replicating one or more desired nucleic acids, a first set of selected adaptors is ligated to the ends of prepared tester nucleic acids and a second set of selected adaptors is ligated to the ends of prepared driver nucleic acids. Adaptor:tester nucleic acid complexes and adaptor:driver nucleic acid complexes are formed. The second set of selected adaptors comprises a site recognized by a selected reagent capable of substantially preventing replication of double-stranded adaptor:driver nucleic acid complexes, and the first set of selected adaptors has a region that is non-homologous to the sequence of nucleotides in the second set. After combining the adaptor:tester nucleic acid complexes with the adaptor:driver nucleic acid complexes to produce double-stranded hybrid nucleic acids, the selected reagent that is capable of substantially cleaving double-stranded adaptor:driver nucleic acid complexes is added. A single stranded nuclease capable of substantially cleaving single stranded nucleic acid complexes is thereafter added. The resulting double-stranded adaptor:tester nucleic acid complexes can then be preferentially replicated or amplified. A particularly preferred aspect of this method utilizes a restriction enzyme as the selected reagent capable of substantially preventing replication of adaptor:tester nucleic acid complexes and the second set of selected adaptors comprises a restriction enzyme recognition site.

The methods of the invention can be used for detecting the presence or absence of a desired nucleic acid. The desired nucleic acids, double-stranded adaptor:tester nucleic acid complexes, are replicated or amplified as indicated. By contacting a probe capable of hybridizing to the desired nucleic acid and identifying the presence of hybridized probe to replicated or amplified double-stranded nucleic acids, one skilled in the art can design numerous detecting methods, assays, and assay kits.

In certain embodiments, kits are provided for preferentially replicating or amplifying one or more desired nucleic acids. The kit comprises one or more selected adaptors, one or more selected primers, a reagent capable of substantially preventing replication or amplification of all but double-stranded desired nucleic acid complexes, and reagents for replicating or amplifying said double-stranded desired nucleic acid complexes, as described herein.

In another aspect of the invention, a method for normalizing a sample of nucleic acids is provided. The method utilizes preferential amplification of nucleic acids present in the lowest abundance in said sample, and comprises ligating a selected adaptor or adaptors to the nucleic acids. Following ligation, the nucleic acids are denatured and then annealed under conditions where nucleic acids present in the highest abundance are substantially double-stranded and nucleic acids present in the lowest abundance are substantially single-stranded. Then, a reagent capable of substantially preventing amplification of all but single-stranded nucleic acids is added. The single-stranded nucleic acids can then be preferentially amplified to normalize the sample.

Also provided are methods for designing an adaptor useful for the preferential replication or amplification of desired nucleic acids. These methods comprise selecting a restriction enzyme recognition site that is substantially cleaved or substantially incapable of cleavage by a restriction enzyme depending on the presence or absence of a selected modified nucleotide in the recognition site. A first nucleic acid is produced comprising the recognition site. Then, optionally, a second nucleic acid, complementary to at least a portion of the first nucleic acid, is produced. The adaptors may be either single-stranded or double-stranded.

The invention also encompasses numerous adaptors useful for the preferential replication or amplification of desired nucleic acids in a nucleic acid replication or amplification process. The adaptors comprise a first region capable of being ligated to a nucleic acid and a second region capable of permitting replication or amplification of ligated nucleic acids or substantially preventing replication or amplification of ligated nucleic acids. As noted above, the selection of an adaptor to be employed in a particular embodiment is generally accomplished in conjunction with the selection of a reagent capable of substantially preventing replication or amplification of all but double-stranded adaptor:tester nucleic acid complexes.

Other preferred adaptors particularly useful for the preferential replication or amplification of desired nucleic acids comprise a restriction enzyme recognition site. The sequence of nucleotides of single-stranded or double-stranded copies of the adaptor has a region capable of permitting replication or amplification or capable of substantially preventing replication or amplification depending on the presence or absence of a selected modified nucleotide or the incorporation of a selected modified nucleotide into copies of the adaptor.

II. Description of Important Concepts and Certain Selected Adaptors of the Invention A. Switchable Adaptors: Their Design and Use In one aspect of the invention, the basic concept is to utilize adaptors that function to preferentially replicate or amplify desired nucleic acids and direct other nucleic acids to be susceptible to an elimination reaction. The elimination reaction involves enzymatic cleavage, where adaptors function to "switch" the susceptibility of desired nucleic acids to a selected enzyme.

1. Adaptors Having Restriction Enzyme Recognition Site Sequences

In preferred embodiments, a switchable adaptor comprises a restriction enzyme recognition site. For example, the "switch" can operate by the presence or absence of one or more modified nucleotides in one or both strands of a restriction enzyme's recognition sequence within the adaptor sequence. The same adaptor is initially ligated to both the tester and driver populations in separate reactions to produce the adaptor:nucleic acid complexes. While the sequence of nucleotides in the adaptors used for both populations may correspond to the same restriction enzyme recognition site, one population, either tester or driver, employs modified nucleotides in the primers and/or reagents used in an extension, replication, or amplification reaction to generate copies of the population. The primer, as in other procedures known in the art, has the same sequence of nucleotides as a portion of the adaptor or its complement. The other population does not employ modified nucleotides and primers if any extension, replication, or amplification reaction is performed prior to combining the two populations.

The presence or absence of modified nucleotides, the "switch" in this example, results in a difference in susceptibility to a selected reagent substantially incapable of cleavage at a modified site, or alternatively, substantially permitting cleavage at a modified site. Preferably, this is accomplished by the selection of a restriction enzyme which, in the presence of a selected modified nucleotide, is either rendered substantially capable or substantially incapable of cleavage at a modified site. Thus, a particular restriction enzyme suitable for use in the invention is incapable of cleaving at methylated sites, or, alternatively, can only leave at methylated sites. Hemimethylation and restriction enzymes that are capable or substantially incapable of cleaving at hemimethylated sites can also be selected and used. Accordingly, various combinations of restriction enzymes, recognition sites, and modified nucleotides are envisioned for use in the invention. A particular method is designed so there is substantially no cleavage in double-stranded tester:tester nucleic acid complexes, but both adaptor:tester/adaptor:driver and double-stranded adaptor:driver nucleic acid complexes are substantially cleaved or susceptible to cleavage. In preferred embodiments, the modified nucleotides can be one of many modified nucleotides, for example the particularly preferred methylated nucleotide bases such as 5-methyl-dCTP, as well as other analogs such as 2'-deoxyriboinosine, 5-iodo-2'-deoxyribocytosine, or 5-mercuri-2'-deoxyriboguanosine.

As noted above, numerous restriction enzymes and recognition sites can be selected for use in the switched adaptor methods of the invention employing modified nucleotides. Generally, restriction enzyme recognition sites comprise two complementary strands. Some of the sites include those where one strand lacks a specific nucleotide base present in the complementary strand and the presence of a selected modified nucleotide protects against cleavage by the restriction enzyme. Also, the site may be recognized by a restriction enzyme capable of cleavage when a selected modified nucleotide is present in either strand but substantially incapable of cleavage when a selected modified nucleotide is present in both of the strands. Or, a site may be recognized by a restriction enzyme substantially incapable of cleavage when a selected modified nucleotide is present in either of the strands. A site can also be recognized by a restriction enzyme capable of cleavage when a selected modified nucleotide is present in either one or both of the strands but substantially incapable of cleavage when a selected modified nucleotide is not present in either of the strands. The selection of one or more adaptors and the extension of nucleic acids to incorporate a selected modified nucleotide, as well as the use of primers with modified nucleotides, thus involves the particular characteristics of the restriction enzyme to be used.

Generally, the selection of adaptors and modified nucleotides is made in conjunction with the reagent for substantially preventing or permitting replication or amplification. As in the methods employing an extension step, noted above, a selected primer is used with the incorporation of modified nucleotides in order to produce complementary strands of adaptor:nucleic acid complexes that are either substantially cleaved or substantially protected from cleavage by the reagent selected. Thus, in particular embodiments where a restriction enzyme is selected, as in the selection of the Eam 1104I restriction enzyme, the modified nucleotides may function to substantially permit restriction enzyme cleavage of all but double-stranded adaptor:tester nucleic acid complexes. Alternatively, the modified nucleotides may function to substantially prevent restriction enzyme cleavage as described herein. Whether the modified nucleotides function to substantially permit or protect restriction enzyme cleavage depends on the adaptors and the particular restriction enzyme selected for use.

In a particularly preferred recognition site and restriction enzyme combination for this invention, Eam 1104I is selected and used. The selection and use of Eam 1104I is specifically exemplified below. The Eam 1104I recognition site (CTCTTC) is asymmetric in that one strand of the recognition site lacks a nucleotide base that is present on the complementary strand. For Eam 1104I, cytosine is present in only one strand. Modification of at least one of the cytosine bases inhibits the activity of the Eam 1104I enzyme from cleaving at the recognition site. Therefore, a modified cytosine could be the selected modified nucleotide to use in a switched adaptor embodiment employing Eam 1104I. However, many other asymmetric recognition sites and the corresponding restriction enzymes may be selected for use in other embodiments of the invention.

Also contemplated is the use of adaptors comprising sequences that are recognized by a rare-cutting enzyme. In Example 1 below, Eam 1104I is used as the reagent to substantially prevent replication or amplification of all but double-stranded adaptor:tester nucleic acid complexes. Tester nucleic acid may contain internal Eam sites that may or may not be modified, depending on the particular embodiment of the invention employed. Thus, the internal Eam sites in tester nucleic acids may not be protected from Eam cleavage. The selection and use of a rare-cutting restriction enzyme and site, such as Not I or Asc I, decreases the frequency with which internal sites may be cleaved in desired nucleic acids or adaptor:tester nucleic acid complexes. Due to the non-random arrangement of base pairs in a particular genome, certain restriction enzyme recognition sites may be substantially under-represented in a selected nucleic acid sample. Means for predicting the frequency of cleavage in the nucleic acids of a sample derived from bacterial, yeast, mammalian or other genomes and suitable rare-cutting recognition sites are well known to one of skill in the art. Accordingly, the selection, design, and use of these rare-cutting enzymes is another aspect of the invention.

2. Adaptors Having Regions of Nonhomology

A plurality of adaptors may also be selected for use in certain preferred embodiments of the invention. In addition to comprising a site recognized by a selected reagent capable of substantially preventing replication of double-stranded adaptor:driver nucleic acid complexes, these adaptors may comprise one or more regions of non-homologous nucleotides so that when adaptor:tester and adaptor:driver nucleic acid complexes are combined to anneal and form double-stranded nucleic acids, at least a portion of one of the selected adaptors will not hybridize to another selected adaptor. (See, for example, FIG. 5.) The appropriate adaptors, primers, and reagent, preferably restriction enzymes and single-stranded nucleases, that preferentially cleave at double-stranded or single-stranded sites can be selected and used so that certain adaptor sequences are preferentially cleaved, thus preventing replication or amplification of undesired nucleic acids. The conditions under which the double-stranded nucleic acids are treated with a restriction enzyme may also be manipulated so that certain selected adaptors are in double-stranded or single-stranded forms. Thus, in one embodiment, temperature changes may substantially allow cleavage of certain double-stranded nucleic acids while others are not cleaved. Alternatively, temperature changes may substantially allow single-stranded nucleases to cleave certain single-stranded nucleic acids while double-stranded nucleic acids are not cleaved.

For example, a preferred method for preferentially replicating or amplifying one or more desired nucleic acids comprises ligating a first set of selected adaptors to the ends of tester nucleic acids, thereby producing adaptor:tester nucleic acid complexes, and ligating a second set of selected adaptors to the ends of driver nucleic acids, thereby producing adaptor:driver nucleic acid complexes. The second set of selected adaptors comprises a site recognized by a selected reagent capable of substantially preventing replication of double-stranded adaptor:driver nucleic acid complexes, and contains a region which is non-homologous to the sequence of nucleotides in the first set of selected adaptors. After combining the adaptor:tester nucleic acid complexes with the adaptor:driver nucleic acid complexes to produce double-stranded hybrid nucleic acids as above, a selected reagent is added that is capable of substantially cleaving double-stranded adaptor:driver nucleic acid complexes at the site recognized by the selected cleavage reagent. A single stranded nuclease capable of substantially cleaving single stranded nucleic acid complexes can then be added. The resulting double-stranded adaptor:tester nucleic acid complexes can then be preferentially replicated or amplified.

In another example, a preferred method for preferentially replicating or amplifying one or more desired nucleic acids comprises ligating first and second selected adaptors to the ends of tester nucleic acids, thereby producing adaptor:tester nucleic acid complexes, and ligating third and fourth selected adaptors to the ends of driver nucleic acids, thereby producing adaptor:driver nucleic acid complexes. Either or both of the third or fourth selected adaptors comprises a cleavage site, and the first and second selected adaptors contain a non-homologous region to the sequence of nucleotides in the third and fourth selected adaptors. After combining the adaptor:tester nucleic acid complexes with the adaptor:driver nucleic acid complexes to produce double-stranded hybrid nucleic acids, a selected reagent is added that is capable of substantially cleaving double-stranded adaptor:driver nucleic acid complexes at the cleavage site of the adaptor. A single stranded nuclease capable of substantially cleaving single stranded nucleic acid complexes can then be added. The resulting double-stranded adaptor:tester nucleic acid complexes can then be preferentially replicated or amplified.

In a related aspect of the invention, the elimination reaction involves an exonuclease or endonuclease activity, where the adaptor is switchable with respect to exonuclease or endonuclease susceptibility. In this aspect, the "switch" is operated by the presence or absence of an enzyme recognition sequence located within the adaptor and by a lack of homology between the sequences in the tester and driver populations. The nonhomologous regions of nucleic acid in the tester:driver hybrids affords susceptibility, or alternatively protection, from certain endonucleases or exonucleases. For example, one population, the driver, has adaptors with an enzyme recognition sequence and flanking nucleotide sequences. The other population, the tester, has adaptors lacking the same enzyme recognition sequence and has flanking nucleotide sequences which are nonhomologous to the nucleotide sequences of the driver adaptor. The presence or absence of the enzyme recognition sequence and the nonhomologous flanking nucleotide sequence results in a difference in susceptibility to exonuclease or endonuclease activity. The method is designed so there is substantially no exonuclease and/or endonuclease susceptibility with tester-:tester hybrids, but both tester:driver and driver:driver hybrids are substantially digested or susceptible to digestion. In preferred embodiments, the exonuclease and/or endonuclease activities can be one of many nucleases such as S1nuclease or mung bean nuclease. Sets of one or more tester adaptors and driver adaptors may be used, and the different adaptors within the sets may be ligated to different ends of the tester and/or driver nucleic acids.

The use of a second tester adaptor and corresponding primer, which does not have homology to a first tester adaptor and primer is also contemplated. The use of a second tester adaptor, which is ligated to tester nucleic acid simultaneously with the first adaptor, further increases the efficiency of the amplification reactions by reducing the formation of hairpin loops. Similarly, the use of a second driver adaptor and corresponding primer having an Eam recognition site but not having homology in the flanking sequences to the driver adaptor and primer is also contemplated, which also reduces the formation of hairpin loops.

In other embodiments, the invention involves ligating a first adaptor or adaptors to tester nucleic acid, thereby forming adaptor:tester nucleic acid complexes, and a second adaptor or adaptors to driver nucleic acid, thereby forming adaptor:driver nucleic acid complexes. The tester and driver adaptors are comprised of: 1) a non-homologous region which permits selective replication or amplification of either tester or driver nucleic acids using selected primers therefor; and 2) a substantially homologous region comprising a site recognized by a reagent capable of preventing replication or amplification of double-stranded nucleic acids. Thus, the adaptors utilized in these embodiments function to prevent replication or amplification of double-stranded hybrid nucleic acids but permit replication or amplification of single-stranded nucleic acids by specific primers selected to replicate or amplify tester or driver nucleic acids. After adaptor:tester nucleic acid complexes and adaptor:driver nucleic acid complexes are combined so as to produce double-stranded hybrid nucleic acids, a reagent capable of preventing replication or amplification of double-stranded nucleic acids is added. Accordingly, double-stranded hybrid nucleic acids are not replicated or amplified and, by optionally adding selected primers, the preferential replication or amplification of single-stranded tester or single-stranded driver nucleic acids is accomplished.

Preferably, the adaptor or adaptors comprise a restriction enzyme recognition site and the reagent capable of preventing replication of double-stranded adaptor:nucleic acid complexes is a restriction enzyme capable of cleaving at double-stranded sites and substantially incapable of cleavage at single-stranded sites. Additionally, selected primers or sets of primers specific for the adaptor or adaptors, ligated to tester or driver nucleic acids can be used to further preferentially replicate or amplify either single-stranded tester or drvier nucleic acids.

It will be appreciated that these embodiments are particularly advantageous for the preferential replication or amplification of rare single-stranded tester nucleic acids which, under appropriate hybridization conditions for combining adaptor:tester nucleic acid complexes and adaptor:driver nucleic acid complexes, may not find their complementary strands. (The inability of rare nucleic acids to locate their complementary strands for replication would generally be attributable to the low concentration of such nucleic acids and the length of time required for such rare nucleic acids to hybridize to their complementary strands.) Additionally, these embodiments are advantageous over alternative methods employing single-stranded nucleases in which rare single-stranded tester nucleic acids may be destroyed. Accordingly, as no single-stranded nucleases are utilized in these embodiments, rare tester or driver single-stranded nucleic acids need not find their complement for preferential replication or amplification.

A further advantage of these embodiments is that the tester nucleic acids become normalized with respect to their relative concentration. Abundant tester nucleic acids predominantly form double-stranded adaptor:tester hybrid nucleic acid complexes and, thus, are prevented from replication after the reagent is added. Rare adaptor:tester nucleic acid complexes, however, will not find their complements and can be preferentially replicated or amplified. These embodiments, therefore, drive the concentration of all nucleic acid species toward a common, or substantially normalized, concentration.

B. Adaptors Selected to Substantially Prevent Replication or Amplification and the Use Thereof.

In another aspect of the invention, modified nucleotides are employed in the adaptors or primers or incorporated into copies of nucleic acids by, for example, an extension step, with or without attached adaptor sequences. The presence of modified nucleotides functions to direct the replication or amplification of only desired nucleic acids by, for example, interfering with or substantially preventing the replication or amplification of undesired nucleic acids. These embodiments can also be used in combination with one or more of the elimination reactions noted above.

1. Adaptors With Modified Nucleotides to Substantially Prevent Replication or Amplification of Adaptor:Driver Nucleic Acid Complexes and the Use Thereof.

In certain embodiments of the invention, modified nucleotides are incorporated into the driver samples which impart a replication or amplification interfering character to the double-stranded complexes containing driver:driver and tester:driver hybrids. Thus, neither of these two types of hybrids will be replicated or amplified under certain conditions, or at least, replication or amplification will be substantially prevented from these two types of hybrids. An example of the modified nucleotides suitable for use in the invention includes, but are in no way limited to, psoralen-oligonucleotide conjugates (26). In addition, poly-T or TA-rich regions can be incorporated into nucleic acids in order to impart an increased ability to form thymine dimers in the presence of psoralens (27). Cross-linking hybrids by UVA irradiation after mixing the tester and driver initial amplicon will effectively prevent amplification from tester:driver and driver:driver hybrids.

In another aspect of the invention, modified nucleotides or nucleotide analogs, such as 5-methyl-dCTP, or ribonucleotide analogs can also be incorporated into the driver DNA to impart an amplification interfering character by increasing the melting temperature of the DNA such that it is not as efficiently amplified under certain amplification conditions. Thus, for example, after attaching adaptors, modified nucleotides can be incorporated into the driver samples. After mixing and annealing with the tester sample, tester:tester hybrids are denatured at a lower temperature than tester:driver and driver:driver hybrids. Appropriate temperatures and conditions can be determined by one skilled in the art that denature tester:tester and do not denature driver:driver and tester:driver in order to direct the replication or amplification reaction to tester:tester hybrids. No elimination reaction or reagent is required.

2. Adaptors Comprising Ligands, Haptens, Proteins or Polypeptides to Substantially Prevent Replication or Amplification and the Use Thereof.

In other embodiments of the invention, modified nucleotides comprising a ligand are used in the adaptor and may be incorporated into driver nucleic acids. After allowing the ligand's binding partner to bind ligand, replication or amplification can be prevented since the polymerase involved with the replication or amplification reaction will not be able to utilize the adaptor, primer, and/or template efficiently. For example, biotinylated nucleotides in driver nucleic acids can preferentially prevent replication or amplification of driver:tester and driver:driver hybrids after streptavidin is added. The elimination reaction is, in this case, the binding of streptavidin to the biotinylated driver nucleic acids. Other ligand-binding partner combinations can be devised by those skilled in the art. However, in this aspect of the invention, the ligand-binding partner interaction should withstand the particular conditions selected for replication or amplification in order to substantially prevent or interfere with the reaction.

Alternatively, the adaptor may comprise a protein or polypeptide (or biotin or other hapten), which is recognized by an enzyme capable of cleaving a polynucleotide substrate. In this case, the primer will be a hybrid molecule comprised of a protein (or biotin or other hapten) linked to a polynucleotide. The cleavage enzyme recognizes the site on the protein portion of the primer and then cleaves the polynucleotide portion of the primer thereby removing the priming sites. The cleavage may be performed by a catalytic protein domain of the cleavage enzyme, or may be performed by an organic cleaving moiety linked to the cleavage enzyme. In embodiments of the invention in which the hybrid molecules are comprised of biotin or other haptens, the cleavage enzyme will recognize the biotin or hapten portion of the hybrid molecule. Examples of cleavage enzymes may include hybrid enzymes such as those described in U.S. Pat. No. 5,436,150, issued Jul. 25, 1995, wherein the cleavage domain of the Fok I enzyme is linked to the recognition domain of another protein. Additionally, the recognition site of the cleavage enzyme may be linked to a non-protein cleaving agent, for example, an organic DNA cleaving moiety, such as those described by Oakley, et al. (30). Further, the cleavage enzyme may be an "artificial restriction enzyme" similar to those described in U.S. Pat. No. 4,942,227, issued Jul. 17, 1990.

3. Adaptors Comprising Ribonucleotides to Substantially Prevent the Replication or Amplification and the Use Thereof.

Also contemplated are adaptors comprising ribonucleotides, rather than deoxyribonucleotides. It is well known in the art that ribonucleotides are more easily hydrolyzed under certain conditions, such as high pH, compared to deoxyribonucleotides. Such hydrolysis would result in breaking the nucleotide strand to leave a single-stranded region. A single-stranded also be used where the adaptor has been hydrolyzed in order to remove the remaining and single-stranded adaptor sequence comprising the primer binding site. Accordingly, ribonucleotides incorporated into the primers used in this invention function to direct the elimination of certain hybrids by hydrolysis.

C. Definitions and General Considerations.

In accordance with the invention, the "undesired" nucleic acids are those DNA, RNA, cDNA, mRNA molecules, or the like, which are either common to two or more sources of nucleic acid or are not part of the set of desired nucleic acids. The "desired" or "target" nucleic acids are those to be enriched in a particular sample. The set of "desired" nucleic acids can be, for example, the nucleic acids only expressed in a particular cell type or at a particular cell cycle or growth phase. It can also be a nucleic acid with one discrete sequence. Generally, the tester sample contains the desired nucleic acids. A "population," "subset," or "set" of nucleic acids refers to a collection of one or more nucleic acids. The population, subset or set can be nucleic acids with one discrete sequence or nucleic acids with numerous differing sequences, depending on the circumstances. For example, a "subset" of a particular population may contain one or more nucleic acids having one or more specific sequences of nucleotides.

For practice of this invention, one skilled in the art can use and is familiar with numerous appropriate conditions for "combining" nucleic acids, such as the subtractive hybridization conditions discussed in the listed references and known in the art. The "combining" of nucleic acids and the conditions for combining function to denature and allow complementary or partially complementary sequences to anneal into double-stranded form. The appropriate conditions for denaturing, hybridizing, washing, and other treatments (time, temperature, denaturing strength of buffer, etc.) can also be readily determined by techniques known in the art, for example, by analyzing the $C_o t$ effect (see 23, and the techniques discussed therein). Numerous publications discuss appropriate conditions to be used or to be adapted for use in the combining of nucleic acids as described in this invention and well known techniques for determining optimum conditions can also be used or adapted for use (see 37).

As used in this invention, "replicating" means adding the appropriate reagents (i.e. primers with appropriate sequences, enzymes, polymerases, nucleotides, buffers, etc.) to a sample in order to produce at least one complementary copy of a nucleic acid. One skilled in the art is familiar with numerous replication reactions, such as primer extension reactions, DNA polymerase reactions, reverse transcriptase reactions, and the like that can be used. The nature of the replication reaction selected depends on various factors such as the original source of nucleic acids and the desired final products. There is, therefore, no limitation to the type of replication reaction that can be employed during the "replicating" step in the methods of this invention. The conditions used for "replicating" will vary with the type of reaction selected, as discussed in the references of the art.

As used in this invention, "amplifying" means adding the appropriate reagents (i.e. primers with appropriate sequences, enzymes, polymerases, nucleotides, buffers, etc.) to a sample in order to reproduce, generally in a sequential fashion, numerous copies of one or more nucleic acids present. One skilled in the art is familiar with various nucleic acid amplification reactions, such as the polymerase chain reaction resulting in amplified DNA (17, 18), and the RNA polymerase method (16) resulting in amplified RNA, that be used in "amplifying." Various modifications of the basic amplification reactions, as discussed in the references (17, 18, 19, and 20) and known in the art, can also be employed with specific embodiments of this invention. The nature of the amplification reaction selected depends on various factors such as the original source of nucleic acids and the desired final products. There is, therefore, no limitation to the type of amplification reaction that can be employed during the "amplifying" step in the methods of this invention. The conditions used for "amplifying" will vary with the type of reaction selected, as discussed in the references of the art.

Subtracted nucleic acids or subtracted samples refers to a population of nucleic acids that is a part of an original, generally larger, population. As discussed in the art, undesired nucleic acids are removed by some type of subtraction step, generally involving hybridization. The resulting nucleic acids after substraction is the subtracted sample.

The labeling of nucleic acids generated by the methods of the invention for use as probes can be performed by numerous methods known in the art. (37) Any type of label may be used.

When an elimination reaction comprising a cleavage reagent is employed, the selection of the appropriate adaptors is made in conjunction with the elimination reaction or selected reagent. A selected reagent substantially prevents all but certain nucleic acid complexes from replicating or amplifying, or alternatively, substantially permits replication or amplification of certain nucleic acid complexes. In some embodiments, a selected modified nucleotide and selected primer are also employed together with the selected adaptor and selected reagent. Thus, for example, in an embodiment where the restriction enzyme Eam 1104I substantially prevents replication or amplification of all but desired nucleic acids, an adaptor having the enzyme recognition site for Eam 1104I is selected in combination with the use of modified nucleotides and primers with modified nucleotides, as discussed above. Numerous other examples of selected adaptors used with corresponding reagents in embodiments of this invention are described and many more can be employed by one skilled in the art with the teachings herein.

Sources of nucleic acid suitable for use with the methods and adaptors of this invention specifically include: eukaryotic cells and organisms; prokaryotic cells and organisms; fungi; archaebacteria; plant cells and organisms; cells treated with viruses or phages or other infectious agents; cells containing heterologous nucleic acid; cells at any particular cell cycle or growth phase or synchronized or arrested cells; and cells created by fusion or related cell engineering techniques. Furthermore, one skilled in the art could readily adapt the methods and adaptors of this invention to any identified or synthesized nucleic acid sample. Thus, one skilled in the art does not require an exhaustive list of potential nucleic acid sources. Furthermore, "DNA" as described in this invention can be cDNA, genomic DNA, chemically or enzymatically synthesized DNA, or other DNA molecules or any DNA prepared from one or more of the procedures noted in the references. "RNA" can be mRNA, mitochondrial RNA, chemically or enzymatically synthesized RNA, or other RNA or any RNA prepared from one or more of the procedures noted in the references.

III. Specific Detailed Embodiments and Examples

Certain embodiments of the invention involve the use and design of oligonucleotide adaptors that can be operably ligated or attached to nucleic acids for use in a replication or amplification protocol. The adaptors of the present invention function to preferentially direct a replication or amplification reaction to desired subsets of nucleic acids present in a sample. Accordingly, within any sample of nucleic acids, such as the nucleic acids from one or more tissues, the invention permits the generation of a specific population of nucleic acids corresponding to a desired subset of the nucleic acids in the original sample. For example, if the desired nucleic acids are the subset of nucleic acids expressed only in a tissue-specific manner, the methods and adaptors of the invention can be used to preferentially replicate or amplify the desired nucleic acids within a sample, thereby generating a population of tissue-specific nucleic acids. The invention, therefore, provides a powerful technique for enriching desired subsets of nucleic acids from a sample to be used, for example, in producing subtraction libraries.

In more detail and as noted in the description of certain embodiments above, the selected adaptors may comprise a restriction enzyme recognition site and be used in conjunction with a restriction enzyme as the reagent to substantially prevent replication or amplification of all but double-stranded adaptor:tester nucleic acids. Generally, once the adaptors are ligated to the nucleic acids of a sample, the adaptors function to protect double-stranded adaptor:tester nucleic acid complexes from cleavage by a restriction enzyme. Other, undesired nucleic acids can, however, be cleaved by the restriction enzyme, effectively removing them from the replicable or amplifiable population. The protected nucleic acid complexes can then be preferentially replicated or amplified by, for example, the polymerase chain reaction or other nucleic acid replication or amplification processes.

In another embodiment of the invention, the adaptors function to prevent or interfere with the replication or amplification of undesired nucleic acids. For example, a binding partner reagent binds to undesired nucleic acids containing the appropriate ligand, wherein the binding partner interferes with the subsequent replication or amplification of the undesired nucleic acids. In another example, modified nucleotides bound to a cross-linking agent are incorporated into adaptors attached to the undesired nucleic acids. After the cross-linking reaction, the ability to replicate or amplify the undesired nucleic acids or hybrids containing at least on of the undesired nucleic acids is substantially reduced. Thus, the methods and adaptors of this invention can be used with any modified nucleotides bound to or comprised of a composition or molecule that can effectively function to substantially interfere with replication or amplification reactions.

Also contemplated is the use of driver nucleic acid without the ligation of an adaptor. Without an adaptor, the driver:driver hybrids would not have priming sites and would thus be eliminated from the population in a subsequent replication or amplification reaction. Annealed tester-:driver hybrids would contain a single-stranded region comprising the priming sites. The single-stranded regions of the tester:driver hybrids, including the priming sites contained in the tester adaptor, would be eliminated by digestion with single-stranded nuclease and thus be eliminated in subsequent amplification. Thus, for example, only tester:tester hybrids would retain priming sites following single-stranded nuclease digestion and thus be amplified in the population. Again, nonhybridized molecules can be eliminated by digestion with single-stranded nuclease prior to a amplification step following the nuclease treatment.

In certain aspects of the invention, an extension reaction can be used. The extension reaction functions to incorporate modified nucleotides into a complementary copy of the adaptor and/or the adaptor:nucleic acid complex or to generate a greater number of certain nucleic acids or complexes prior to combining one or more samples of nucleic acids. The selection and use of a modified nucleotide is generally accomplished in conjunction with the selection of adaptor and reagent capable of substantially preventing all but double-stranded adaptor:tester nucleic acid complexes. In addition, an optional single-stranded nuclease step can be added to many of the methods in order to eliminate single-stranded adaptor:nucleic acid complexes, thereby preventing replication or amplification from the single-stranded nucleic acids. Also, the nucleic acids from one or more selected populations to be used in the methods and with the adaptors of the invention can be prepared by an optional restriction enzyme cleavage step, prior to ligating selected adaptors. A sonication or shearing step may also optionally be used. Generally, the nucleic acids can be initially prepared by one or more optional purification steps, including extractions and electrophoresis processes. Preparing nucleic acids functions to allow a selected one or more adaptors to be ligated to the ends of the nucleic acids in the sample. In addition, preparing nucleic acids may simply function to separate one population of nucleic acids from another one or more populations.

A. Switched Adaptor Methods

In accordance with this invention, there are various approaches one skilled in the art can utilize to switch a selected adaptor's susceptibility to a restriction enzyme. For example, the incorporation of modified nucleotides, such as methylated nucleotides, can result in an adaptor being either susceptible or resistant to cleavage by a restriction enzyme. The susceptibility to cleavage can be used to substantially eliminate replication or amplification of undesired nucleic acids while the resistance to cleavage can be used to protect desired nucleic acids from cleavage. Two selected restriction enzymes for the embodiments of a switched adaptor, one conferring susceptibility and the other resistance to restriction enzyme cleavage, are detailed below. However, many other restriction enzymes can be selected and used by one skilled in the art.

The restriction enzyme Dpn I, which cleaves DNA that is methylated in its GATC recognition site, can be selected for use with a switchable adaptor rendering undesired nucleic acids susceptible to cleavage. An adaptor with the GATC sequence would be ligated to both the driver and tester populations. By incorporating a selected modified nucleotide, methyl-dATP, into driver and unmodified dATP into tester in an extension reaction, methylated driver nucleic acids and unmethylated tester nucleic acids are produced. After combining to anneal driver and tester nucleic acids, the adaptor sequence can be cleaved by Dpn I in methylated driver:driver hybrids but not in unmethylated tester:tester hybrids. Driver:tester hybrids may also be cleaved by Dpn I at hemimethylated recognition sites. Once the adaptor sequence is cleaved from the hybrids, a primer designed to bind in the adaptor sequence will not bind and the cleaved nucleic acids will not be exponentially amplified.

An example of a selected adaptor rendering desired nucleic acids resistant to cleavage by a restriction enzyme utilizes the restriction enzyme recognition site for Eam 1104I, which will not cleave DNA when its CTCTTC recognition site is methylated. An adaptor with the CTCTTC sequence is ligated to both the driver and tester populations. To assure efficient cleavage of nucleic acid hybrids, adaptors can optionally contain two inverted copies of the Eam 1104I asymmetric recognition site. Incorporating a selected modified nucleotide, such as methyl-dCTP, into tester nucleic acids in an extension reaction results in methylated tester nucleic acids. Unmodified dCTP is incorporated into driver nucleic acids in an extension reaction resulting in unmethylated driver nucleic acids. After combining tester and driver to anneal homologous nucleic acids, the adaptor sequence can be cleaved from driver:driver hybrids by Eam 1104I but not from methylated tester:tester hybrids. Driver:tester hybrids are also cleaved by Eam 1104I at unmethylated recognition sequences. Following cleavage of the undesired nucleic acids by Eam 1104I, an amplification primer will not bind and the nucleic acids will not be replicated or exponentially amplified.

The use of the recognition site sequence of Eam 1104I in an adaptor is a particularly preferred embodiment of the switched adaptor substraction method because the site contains three cytosine residues in one strand which are lacking in the complementary strand. The incorporation of a single methylated C into the appropriate strand of the Eam 1104I site will protect a nucleic acid from cleavage. Accordingly, a high degree of protection of desired nucleic acids is achieved, which increases the efficiency of replicating or amplifying double-stranded adaptor:tester nucleic acid complexes, the desired nucleic acids.

Eam is a very efficient enzyme and, thus, a reliable method of cleavage. However, in this preferred embodiment of the invention any enzyme can be used for which the recognition sequence contains in one strand, but not in the other strand, a modifiable nucleotide that causes a change in the ability or propensity of an enzyme to cleave. For example, Mbo II, with the recognition sequence 5'-GAAGA-3', could be used by incorporating 6-methyl-dATP in one strand to prevent cleavage. The opposite strand does not possess an A residue. Similarly, Ear I, Fok I, Hph I, and Mnl I can be employed. As noted above, other enzyme recognition sites can be used, irrespective of the particular base pairs of the sequence, in other embodiments of the switchable adaptor subtraction method. Accordingly, the description of Eam as a preferred embodiment does not limit the scope of this invention.

B. Design of Adaptor Sequences: Selection of Restriction Enzyme Sites for Switchable Adaptors.

Preferred adaptor sequences for an embodiment employing Eam 1104I are listed below as adaptors A and B, with corresponding primers. Adaptors A and B can be employed as double-stranded molecules, where the complement of the lower (shorter) sequences anneals to part of the upper (longer) sequence. Adaptors A and B can also be employed as single-stranded molecules consisting of the upper sequences only.

strand to become covalently attached to the end of the DNA fragment having a 5' phosphate, whereas the complementary lower strand does not ligate due to its designed lack of a 5' phosphate.

Figure 1B:
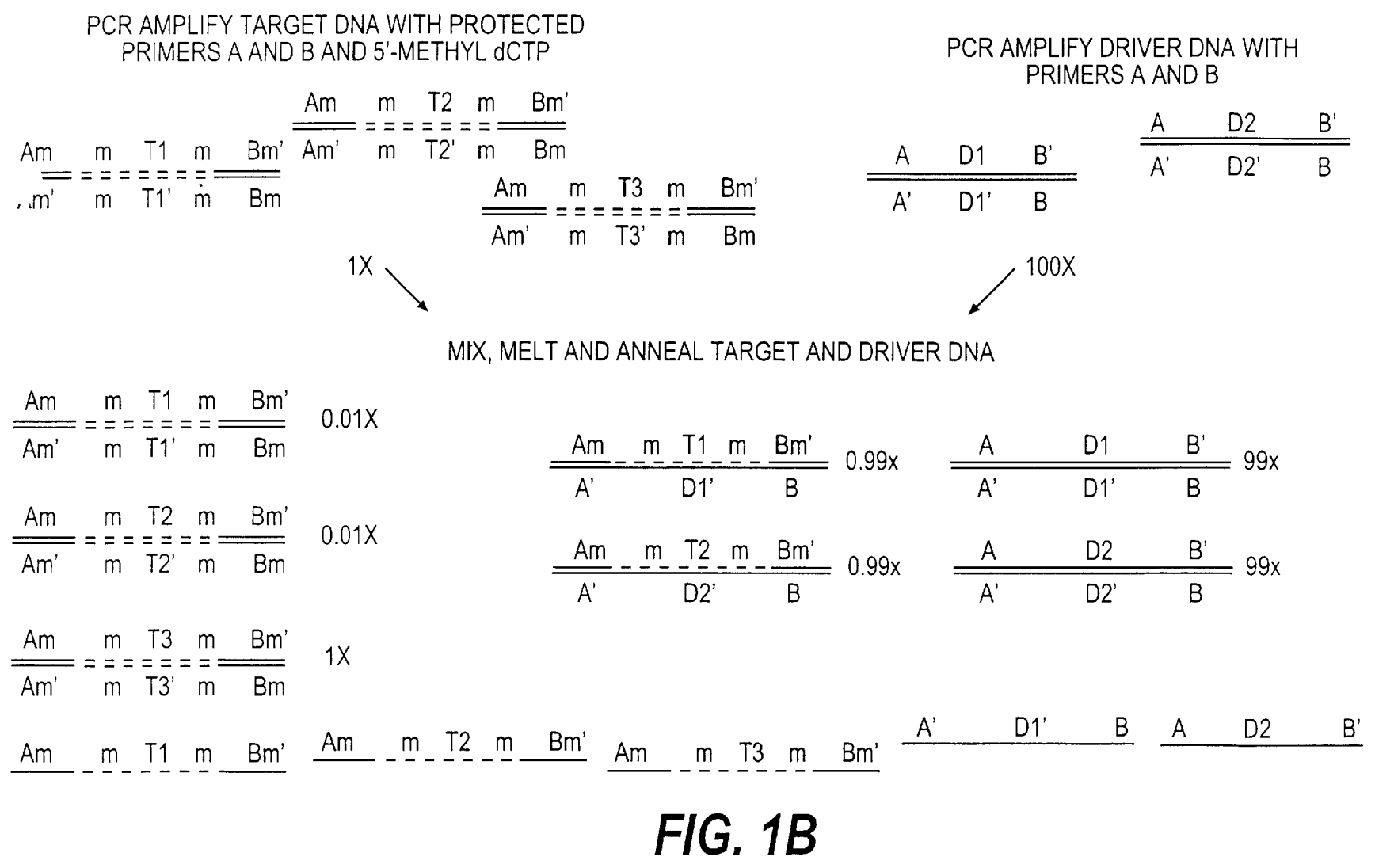
Figure 1C:
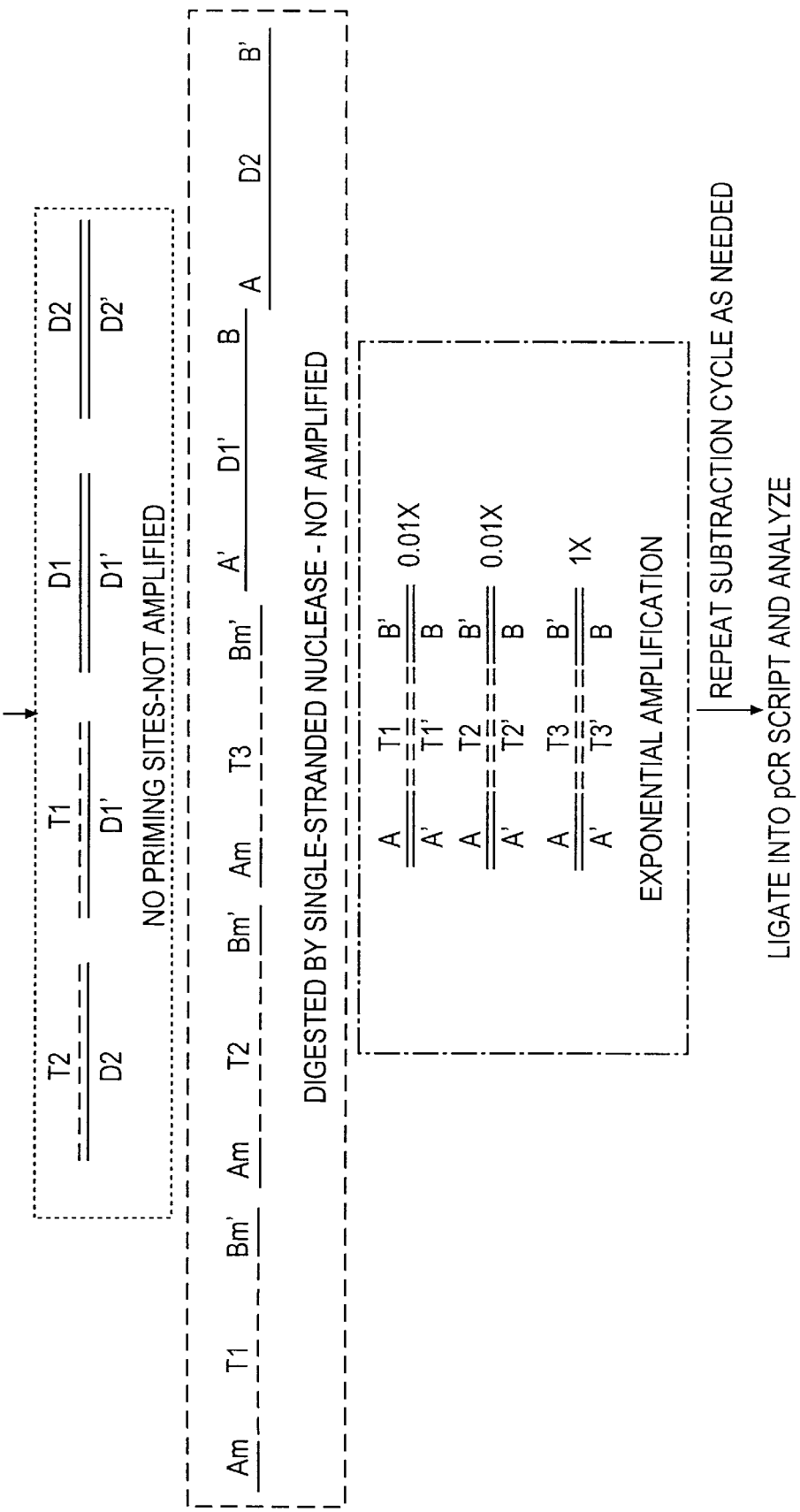

An extension reaction may be performed on the ligated adaptor:nucleic acid complex. A polymerase activity is allowed to extend the 3' ends of the nucleic acids. This displaces the lower adaptor strand and synthesizes the entire region complementary to the upper strand in its place (see FIGS. 1 and 2 employing adaptor strands labeled A/A' and B/B'). The selected primer, as shown above for adaptors A and B, can then anneal to the newly synthesized DNA and prime synthesis.

In one type of extension reaction, PCR is used on tester nucleic acids with one or more methylated primers and in the presence of sufficient methyl-dCTP so that some or all of the cytosine residues in the PCR-produced fragment are methylated (8). Partial incorporation of methyl-dCTP during PCR protects the resulting DNA from cleavage by Eam 1104I provided that at least one methylation sensitive site in the recognition site becomes modified by a methyl group (8). Since each Eam 1104I recognition site contains three C's in

```
Primers
                           (m)
           5'-ACTACTTATCTATGTTCT-3'              (SEQ ID NO: 1)
                          (m m)
           5'-ACTACTTATCTATGTTCTCT-3'            (SEQ ID NO: 2)
                         (m m  m)
              5'-ACTTATCTATGTTCTCTTCG-3'         (SEQ ID NO: 3)

(m m  m)
Adaptor A  5'-TAACTACTTATCTATGTTCTCTTCGAAGAGGCAC-3'  (SEQ ID NO: 4)
                          3'-AGCTTCTCCGTG-5'         (SEQ ID NO: 5)

Primers
                           (m)
           5'-GTAGTGTAGGTCTACTAGCT-3'             (SEQ ID NO: 6)
                          (m m)
           5'-AGTGTAGGTCTACTAGCTCT-3'             (SEQ ID NO: 7)
                         (m m  m)
              5'-GTAGGTCTACTAGCTCTTCG             (SEQ ID NO: 8)

(m m  m)
Adaptor B  5'-GTAGTGTAGGTCTACTAGCTCTTCGAAGAGGACT-3'  (SEQ ID NO: 9)
                          3'-AGCTTCTCCTGA-5'         (SEQ ID NO: 10)
```

Adaptors A and B contain two inverted copies of the Eam 1104I recognition site CTCTTC. The primers comprise all or a part of one or both of the Eam 1104I sites. One or more of the cytosine residues in the CTCTTC recognition site is optionally methylated. An (m) over a residue, for example the cytosine residues in the examples herein, represents an optionally modified, or preferably methylated, nucleotide. As shown in adaptors A and B, the upper strand of the adaptor is longer than the lower strand of the adaptor.

one of its strands, and no C's in the complementary strand, the adaptor sequence of the tester nucleic acid becomes protected from cleavage by Eam 1104I through hemimethylation of each recognition site (8). For example, the sequences below, representing tester nucleic acids (TESTER) amplified in the presence of methylated primers and methyl-dCTP, are not susceptible to cleavage by Eam 1104I.

```
           Adaptor A                                              Adaptor B
          m   m   m            m m         mm m  m        m         mm  m  m  m
5'-TAACTACTTA TCTATGTTCT CTTCGAAGAG GCAC-TESTER-AGTCCTCTTC GAAGAGCTAG TAGACCTACA CTAC-3'
3'-ATTGATGAAT AGATACAAGA GAAGCTTCTC CGTG-TESTER-TCAGGAGAAG CTTCTCGATC ATCTGGATGT GATG-5'
           m         m   mm m                      m                 m    m  m
```

However, the lower strand may also be up to the same length or longer than the upper strand of the adaptor.

As described herein, the adaptor can be "blunt ended." However, if desired, the adaptor can also have a sticky end (at the right end of the sequence shown) for ligation to DNA having a compatible overhang. Ligation of a sticky end adaptor to a DNA fragment having a 5' terminal phosphate, as used with T4 DNA or RNA ligase (25), causes the upper The example uses two nonidentical adaptors. The adaptors given are labeled above the appropriate sequences. The use of two identical adaptors is also described herein. One or more of the cytosine residues in the Eam 1104I recognition sequence (CTCTTC) is optionally methylated. An "m" over or above a residue, for example the C residues in the examples herein, represents a methylated nucleotide. Eam 1104I sequences in the adaptor sequences are protected from cleavage by the presence of one or more methyl dCTP residues. Internal sites in the tester DNA are also protected from Eam 1104I cleavage by incorporating methyl dCTP during amplification.

In contrast, the sequences below represent driver nucleic acids (DRIVER) amplified in the presence of normal primers and dCTP, which are susceptible to cleavage by Eam 1104I.

```
Adaptor A                                            Adaptor B
5'-TAACTACTTA TCTATGTTCT CTTCGAAGAGG CAC-DRIVER-AGTCCTCTTC GAAGAGCTAG TAGACCTAC ACTAC-3'
3'-ATTGATGAAT AGATACAAGA GAAGCTTCTCC GTG-DRIVER-TCAGGAGAAG CTTCTCGATC ATCTGGATG TGATG-5'
```

The example uses two nonidentical adaptors. The adaptors given are labeled above the appropriate sequences. The use of two identical adaptors to prepare driver nucleic acids is also described herein. In the driver nucleic acids, the cytosine residues in the underlined Eam 1104I recognition sequence (CTCTTC) are not methylated. Eam 1104I sequences in the adaptor which are not protected from cleavage by Eam 1104I are underlined. Additionally, internal sequences are not protected from cleavage by Eam 1104I.

The amplified tester and driver nucleic acids are then combined (i.e., denatured and hybridized) to form the following tester:tester, tester:driver and driver:driver hybrids.

containing the primer binding region will be cleaved from the main molecule (TESTER or DRIVER nucleic acid). Thus, the lack of methyl protection in one strand renders a nucleic acid susceptible to Eam 1104I. Driver molecules hybridized to tester molecules (driver:tester hybrids) are cleaved by Eam 1104I and effectively drop out of the replicable or amplifiable population. Driver:driver hybrids are also cleaved by Eam 1104I and also drop out of the replicable or amplifiable population. Nonhybridized nucleic acids (either tester or driver) can also be eliminated from the population by an optional single-strand nuclease treatment, An example of another adaptor, adaptor C and associated primer, follows: such as S1 or mung bean nuclease treatment. In contrast, tester:tester hybrids containing methylated Eam 1104I sites are protected from cleavage and are replicated or amplified exponentially.

```
Adaptor A                                            Adaptor B
           m   m   m          m m                  mm m   m          m          mm   m   m   m
5'-TAACTACTTA TCTATGTTCT CTTCGAAGAG GCAC-TESTER-AGTCCTCTTC GAAGAGCTAG TAGACCTACA CTAC-3'
3'-ATTGATGAAT AGATACAAGA GAAGCTTCTC CGTG-TESTER-TCAGGAGAAG CTTCTCGATC ATCTGGATGT GATG-5'
     m           m   mmm m              m              m   m   m Adaptor A                                            Adaptor B
           m   m   m          m m                  mm m   m          m          mm   m   m   m
5'-TAACTACTTA TCTATGTTCT CTTCGAAGAG GCAC-TESTER-AGTCCTCTTC GAAGAGCTAGTAG ACCTAC ACTAC-3'
3'-ATTGATGAAT AGATACAAGA GAAGCTTCTC CGTG-DRIVER-TCAGGAGAAG CTTCTCGATCATC TGGATG TGATG-5'

Adaptor A                    Adaptor B
5'-TAACTACTTA TCTATGTTCT CTTCGAAGAG GCAC-DRIVER-AGTCCTCTTC GAAGAGCTAG TAGACCTAC ACTAC-3'
3'-ATTGATGAAT AGATACAAGA GAAGCTTCTC CGTG-DRIVER-TCAGGAGAAG CTTCTCGATC ATCTGGATG TGATG-5'
```

The underlined sequences in the driver strand are unprotected Eam 1104I sites. An "m" over or under a residue, for example the C residues in the tester nucleic acid herein, represents a potentially modified or methylated nucleotide. Thus, one or more of the C residues may be methylated.

Contacting these tester:driver and driver:driver hybrids with Eam 1104I will cleave the primer binding sites from the tester:driver and driver:driver nucleic acids. After cleavage with Eam 1104I, these driver and tester molecules will not be substrates for replication or amplification with the selected primer since both strands of the adaptor sequence An example of another adaptor, adaptor C and associated primer, follows:

```
                                               (m m  m)
Primer  (SEQ ID NO: 11) 5'-AGGTCTACTA GCTCTTCNNN-3'
Adaptor (SEQ ID NO: 12) 5'-AGGTCTACTA GCTCTTCNNNGAAGAG-3'
        (SEQ ID NO: 13)                    3'-AAGNNNCTTCTC-5'
```

Here, the adaptor also contains two inverted copies of the Eam 1104I recognition site CTCTTC. The NNN sequence is any sequence of choice and may represent a degenerate sequence.

As described above for adaptors A and B, amplification of adaptor C:tester nucleic acid complexes is carried out with a methylated primer and in the presence of methyl-dCTP so that all or some of the cytosine residues in the tester nucleic acids are methylated (8). Again, partial incorporation of methyl-dCTP into the Eam 1104I recognition sequence during amplification protects the DNA from cleavage by Eam 1104I.

For example, the sequences below are not susceptible to Eam cleavage.

```
Adaptor C    m m m                          m m m
5'-AGGTCTACTA GCTCTTCNNN GAAGAG-DNA-TESTER-CTCTTCNNNG AAGAGCTAGT AGACCT-3'
3'-TCCAGATGAT CGAGAAGNNN CTTCTC-DNA-TESTER-GAGAAGNNNC TTCTCGATCA TCTGGA-5'
             m m m                         m         m m m
```

However, the following hybrids will be susceptible to Eam cleavage at the underlined sites.

```
Adaptor C    m m m                          m m m
5'-AGGTCTACTA GCTCTTCNNN GAAGAG-DNA-TESTER-CTCTTCNNNG AAGAGCTAGT AGACCT-3'
3'-TCCAGATGAT CGAGAAGNNN CTTCTC-DNA-DRIVER-GAGAAGNNNC TTCTCGATCA TCTGGA-5'

Adaptor C
5'-AGGTCTACTA GCTCTTCNNN GAAGAG-DNA-DRIVER-CTCTTCNNNG AAGAGCGAGT AGACCT-3'
3'-TCCAGATGAG CGAGAAGNNN CTTCTC-DNA-TESTER-GAGAAGNNNC TTCTCGATCA TCTGGA-5'
             m m m                         m         m m m
```

Eam cleaves driver strands in the NNN sequence, leaving three-base 5' overhangs. If one of the bases in the NNN sequence is a C and it becomes methylated, it will not inhibit cleavage by Eam as only methylation in the recognition sequence inhibits enzyme activity (8).

C. Adaptor Pairs Comprising Nonhomologous Sequences

In certain adaptor designs, the adaptor sequences of the tester and driver strands are not complementary and do not hybridize to form double-stranded nucleic acids under certain temperatures and conditions. When the adaptor sequences are not double-stranded, the adaptor:nucleic acid complexes are not susceptible to certain cleavage reactions. For example, a restriction enzyme such as Eam does not cleave single-stranded DNA as efficiently as double-stranded DNA. Adaptors can be selected and ligated so that tester:driver hybrids, under appropriate conditions, are not efficiently cleaved in the presence of Eam. The non-annealed adaptor sequences of the annealed tester and driver strands can be removed by single-stranded exonuclease or endonuclease activity. S1 nuclease has both of these activities and can effectively remove the non-annealed adaptor sequences. Removal of these primer binding sequences from tester-:driver hybrids effectively eliminates them from the replicable or amplifiable population. Further, as the tester:tester hybrids do not contain an enzyme recognition site and anneal to form double-stranded DNA, these hybrids are not cleaved in the presence of Eam nor digested by S1 nuclease. Also, as the driver:driver hybrids contain an Eam recognition site, they are cleaved by Eam, the primer binding sites are removed, and the driver:driver hybrids effectively drop out of the replicable or amplifiable population. Nonhybridized molecules (either tester or driver) can also be eliminated from the population by single-stranded nuclease treatment, such as S1 nuclease, prior to further extension, replication or amplification.

Tester molecules can be further selected for in subsequent amplifications by the use of tester-specific primers, which do not anneal to driver molecules and thus do not amplify driver molecules.

An example of a driver adaptor that can be designed for the nonhomologous sequence embodiments of the adaptors of this invention, adaptor D with a single Eam site, and the corresponding PCR primer is as follows:

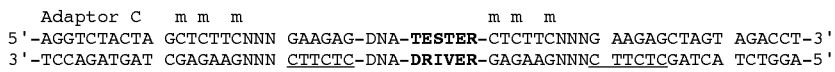

The 5' terminal sequence ('NNNNNN . . . ') in both the adaptor and primer can be varied in both length and nucleotide sequence. The sequence may be predetermined when used in a particular embodiment to accommodate a required sequence for a particular use. An example of the range in size for the 5' terminal sequence is from about 1 to about 18 nucleotides, however, the sequence may also be greater than 18 nucleotides. The 'NNN' sequence, after the CTCTTC recognition site, is any sequence of choice and does not necessarily represent a degenerate sequence. However, as detailed below, when two adaptors are ligated to a DNA fragment, the nucleotide sequence not in the Eam 1104I recognition site or the reverse complement sequence (i.e., the 'NNN . . . ' region) can be unique. Certain embodiments of the adaptors described herein have 18 bp of unique sequence. For example, the 5' to 3' direction, the adaptors comprise the Eam 1104I recognition site, the reverse complement of the Eam 1104I recognition site, and 4 bp of unique sequence.

A preferred driver adapter E with a single Eam site and primer follow:

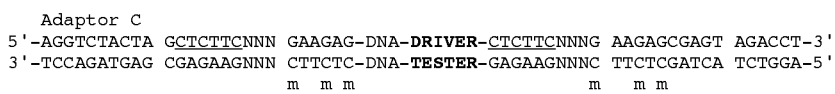

This adaptor contains a single copy of the recognition sequence 5'-CTCTTC-3' for the enzyme Eam. Again, the "NNN" sequence is any sequence of choice, and does not necessarily represent a degenerate sequence.

An example of a tester adaptor F corresponding to use with adaptor E above, and the associated PCR primer, is as follows:

```
Primer  (SEQ ID NO: 20) 5'-NNNNNNNNNN NNNNNNNNNN NNNNN-3'
Adaptor (SEQ ID NO: 21) 5'-NNNNNNNNNN NNNNNNNNNN NNNNNNNN-3'
        (SEQ ID NO: 22)                     3'-NNNN NNNNNNNN-5'
```

The sequence ('NNNNNN . . . ') in both the adaptor and primer can be varied in both length and nucleotide content. The sequence may be predetermined when used in a particular embodiment. An example of the range in size for the sequence is from about 1 to about 18 nucleotides, however, the sequence may also be greater than 18 nucleotides. The 'NNNNNN . . . ' sequence is any sequence of choice and does not necessarily represent a degenerate sequence, however, the sequence does not contain an Eam site or an inverted Eam site.

A species of the tester adaptor F above can be the preferred tester adaptor G and associated primer, as follows:

comprise nucleotides which can serve as priming sites, the nucleotide sequence recognized by the restriction enzyme Eam 1104I, and the reverse complement of the nucleotide sequence recognized by Eam 1104I. When DNA comprising an Eam 1104I recognition site is incubated in the presence of Eam 1104I, the DNA is cleaved one base pair 3' of the Eam 1104I site and has a 3 base pair overhang.

The priming site may comprise one or more of the nucleotides encoding the Eam 1104I recognition site or its reverse complement. The priming site is positioned to allow amplification of only those single-stranded DNA fragments that have not been cleaved with Eam 1104I. One or more priming sites may be used to amplify a DNA fragment.

```
Adaptor G
Primer  (SEQ ID NO: 23) 5'-CTTAGCTAAC GTCATTAGCC TAGCT-3'
Adaptor (SEQ ID NO: 24) 5'-CTTAGCTAAC GTCATTAGCC TAGCTCTGA-3'
Adaptor (SEQ ID NO: 25)                     3'-TCGG ATCGAGACT-5'
```

The adaptors F and G do not contain an Eam recognition site (CTCTTC) or the inverse complement of the site (GAGAAG). Tester adaptor G and driver adaptor E do not contain sufficiently homologous sequences to anneal under the conditions described herein.

After ligation of driver adaptor E to driver nucleic acid, to form adaptor E:driver nucleic acid complexes, and the ligation of tester adaptor G to tester nucleic acids, to form adaptor G:tester nucleic acid complexes, one or both of the sets of complexes can be extended or PCR amplified as described above. The tester DNA may or may not be extended or amplified with methylated primers and 5-methyl-dCTP. If the tester DNA is not extended or amplified with 5-methyl-dCTP, any internal Eam sites will not methylated and Eam will cleavage within the sequence.

After combining tester- and driver-containing complexes by denaturing and annealing, the following tester and driver hybrids are formed:

One end of the adaptors is ligated to the DNA fragment. The adaptors described herein are 'blunt ended' and thus are ligatable to 'blunt ended' DNA fragments. Examples of restriction enzymes that can be used to digest DNA to generate DNA fragments having blunt ends are Alu I and Rsa I. Additional restriction enzymes known to generate blunt ends are well known to one of skill in the art. The adaptors may also have overhanging ends for ligation to DNA fragments having compatible overhanging ends. If desired, the overhanging ends can be removed or filled in by digestion or polymerization with a suitable exonuclease, endonuclease, or polymerase to generate blunt ends. Additionally, one or more of the adaptors or DNA fragments may be cleaved with one or more restriction enzymes which generate overhanging ends. Also contemplated are two adaptors having noncompatible overhanging ends for directional ligation of the adaptors to a DNA fragment.

When adaptors are ligated to DNA fragments having blunt ends and it is desired to have a different adaptor ligated to

```
Adaptor E (SEQ ID NO: 18)
5'-TAACTACTTA TCTATGTTCT CTTCGCAC-DRIVER-GTGCGAAGAG AACATAGATA AGTAGTTA-3'
3'-ATTGATGAAT AGATACAAGA GAAGCGTG-DRIVER-CACGCTTCTC TTGTATCTAT TCATCAAT-5'
Adaptor E complement (SEQ ID NO: 26)

Adaptor G (SEQ ID NO: 24)       m           m    m      m    m     m
5'-CTTAGCTAAC GTCATTAGCC TAGCTCTG-TESTER-TCAGAGCTAG GCTAATGACG TTAGCTAAG-3'
3'-GAATCGATTG CAGTAATCCC ATCGAGAC-TESTER-AGTCTCGATC CGATTACTGC AATCGATTC-3'
      m   m    mmm   m   m        m
Adaptor G complement (SEQ ID NO: 27)

Adaptor E (SEQ ID NO: 18)
5'-TAACTACTTA TCTATGTTCT CTTCGCAC-DRIVER-GTGCGAAGAG AACATAGATA AGTAGTTA-3'
3'-GAATCGATTG CAGTAATCCC ATCGAGAC-TESTER-AGTCTCGATC CGATTACTGC AATCGATTFC-3'
      m   m    mmm   m   m        m
Adaptor G complement (SEQ ID NO: 27)
```

The underlined sequences from the driver strand are unprotected Eam sites. Thus, subsequent treatment of these tester-:driver hybrids with Eam restriction enzyme will cleave the primer binding sites from the molecules.

EXAMPLE 1

Subtraction Using Plasmid DNA Adaptors and PCR Primers

Adaptors and PCR primers were designed for the differential cleavage of driver and tester DNA. The adaptors each end of the DNA fragment, it is preferable to use equal molar amounts of each adaptor when ligating to the DNA fragment. Additionally, simultaneous rather than sequential ligation of each adaptor is preferred.

In this example, the adaptors are generated by annealing two nucleotides in regions of sequence complementarity. The two strands of the adaptors can be referred to as the "upper" and "lower" strands. The nucleotide sequence of both strands should, optionally, not be self-complementary to reduce the ability of the oligonucleotides to self-anneal or to form hairpin loops. The adaptor can also be a single-stranded nucleotide sequence and be ligated to either a double or single-stranded DNA fragment.

Preparation of Driver and Tester Plasmid DNA

For a model system of switched adaptor subtraction, driver and tester DNA having both common and unique DNA sequences were selected. Those DNA sequences in common were removed from the mixture comprising common and unique driver and tester DNA sequences by the method of this invention, and those unique DNA sequences were amplified.

Driver and tester DNA were prepared from pBluescript® II SK(−) phagemid vector (pSK-) and pNCAM, respectively. The pNCAM is a pSK- phagemid with a cDNA insert encoding rat NCAM from nucleotide positions 1300 to 3170 (nucleotide positions are based upon the nucleotide sequence given in GenBank Accession Number X06564) ligated at the EcoR I and Xho I sites in the vector. The pSK- phagemid vector is available from Stratagene (La Jolla, Calif.).

Digestion of Driver and Tester DNA

The driver and tester DNA were restriction digested with Alu I to generate DNA fragments ranging from 42 to 710 base pairs (bp) in the driver sample and 6 to 853 bp in the tester sample. Approximately forty micrograms (μg) of pNCAM DNA were digested in 1×optimal buffer #3 (1×optimal buffer #3 is 50 millimolar [mM] NaCl, 25 mM Tris-HCl [pH 7.7], 10 mM $MgCl_2$, 10 mM β-mercaptoethanol and 100 μg/milliliter [ml] bovine serum albumin [BSA]) (Stratagene; La Jolla, Calif.) with 15 units of Alu I (Stratagene; La Jolla, Calif.) at 37° C. for approximately 16 hours. The Alu I was removed by adding an equal volume of phenol and chloroform, vortexing, and centrifuging at 14,000×g for 10 minutes. The supernatant containing the digested DNA was transferred to a separate container. The DNA was then precipitated by adding a 0.1 volume of 3 M NaOAc, pH 5.2 and 3 volumes of 100% (v/v) ethanol, centrifuging at 14,000×g for 10 minutes, decanting the supernatant, adding 0.5 ml 80% (v/v) ethanol, centrifuging at 14,000×g for 10 minutes, decanting the supernatant, drying the DNA and resuspending the DNA in 40 microliters (μl) TE (TE is 5 mM tris-HCl, pH 8.0 and 0.1 mM ethylenediaminetetraacetic acid [EDTA]) to a DNA concentration of approximately 1 μg/μl.

The molecular weights of the DNA fragments were visualized by ethidium bromide staining following electrophoresis of the fragments in a VisiGel™ separation matrix (Stratagene; La Jolla, Calif.) and compared to a molecular weight markers of known base pair sizes of the φX174 genomic DNA digested with the restriction enzyme Hae III (Stratagene; La Jolla, Calif.). The molecular weights of the pSK- and pNCAM DNA fragments following Alu I digestion were as expected (Table 1). The molecular weights of the pSK- and pNCAM DNA fragments following Alu I and Eam I digestion are also given in Table 1. DNA fragments less than 250 bp are not well resolved using the VisiGel™ separation matrix and therefore are not considered in interpreting these results. The molecular weights of these fragments increased upon ligation of the adaptors, however, they are referred to herein by the size in base pairs as given in Table 1. In Table 1, the * refers to a DNA fragment given in the same line (under Alu I DNA Fragments) that has been digested with Eam 1104I to generate DNA fragments having the indicated number of base pairs.

TABLE 1

| Alu I DNA Fragments | | Alu I and Eam 11041 DNA Fragments | |
|---|---|---|---|
| pBluescript II SK(−) | pNCAM | pBluescript II SK(−) | pNCAM |
|  | 853 |  | 853 |
| 710 | 710 | 443/267* | 443/267* |
| 521 | 521 | 521 | 521 |
|  | 430 |  | 430 |
| 257 | 257 | 257 | 257 |
| 257 | 257 | 257 | 257 |
| 226 | 226 | 226 | 226 |
|  | 219 |  | 111/108* |
|  | 208 |  | 208 |
|  | 141 |  | 141 |
| 126 |  | 126 |  |
| 125 | 125 | 113/12* | 113/12* |
| 118 | 118 | 60/58* | 60/58* |
|  | 103 |  | 103 |
| 100 | 100 | 100 | 100 |
| 95 | 95 | 95 | 95 |
| 90 | 90 | 90 | 90 |
| 66 |  | 66 |  |
| 64 | 64 | 64 | 64 |
| 63 | 63 | 63 | 63 |
| 55 |  | 55 |  |
| 46 | 46 | 46 | 46 |
|  | 45 |  | 45 |
| 42 |  | 42 |  |
|  | 33 |  | 33 |
|  | 30 |  | 30 |
|  | 23 |  | 6/17* |
|  | 22 |  | 22 |
|  | 16 |  | 16 |
|  | 6 |  | 6 |

In order for subtraction to occur, the pNCAM digested with Alu I (tester DNA) must comprise DNA fragments that are not in the pSK- digested with Alu I (driver DNA) DNA fragments. The pNCAM digested with Alu I comprised DNA fragments of 853, 430, 219, 208, 141, 103, 33, 30, 23, 22, 16 and 8 bp that are not present in the pSK- digested with Alu I (Table 1). The molecular weight of these DNA fragments is based upon the nucleotide sequence given in GenBank Accession Number X06564. While the nucleotide sequence of pNCAM was not confirmed by us, the molecular weights of the pNCAM DNA fragments correspond to the expected molecular weights within the limits of the resolution of the gel matrix. Due to the methods used to prepare pNCAM, the pSK- also contains DNA fragments of 126, 66, 55, and 42 bp that are not present in pNCAM. While the presence of DNA fragments in a driver DNA (pSK-) that are not present in the target DNA (PNCAM) is generally undesirable, the molecular weight of these DNA fragments is low and are therefore not likely to be resolved and be detectable in the VisiGel separation matrix.

The pSK- DNA fragments of 710 and 125 bp each have a single internal Eam 1104I restriction site. When these DNA fragments are incubated in the presence of Eam 1104I, the DNA are cleaved and generate DNA fragments of 443 and 267 and 113 and 12 bp, respectively (Table 1). Methyl dCTP, which protects against cleavage of internal Eam 1104I sites in pNCAM (tester DNA), is not incorporated into the pSK- DNA (driver DNA) and therefore does not protect against cleavage at these sites. Cleavage at these sites effectively separates the two PCR priming sites required for exponential amplification of these DNA fragments in subsequent PCR, therefore, the cleaved DNA amplify linearly and their concentration relative to that of exponentially amplified DNA is reduced during subsequent PCR. Cleavage at these internal sites is easily detected by gel analysis as described herein.

The pNCAM DNA fragments of 710, 219, 125, 118 and 23 bp each contain a single internal Eam 1104I restriction site which, when cleaved, generates DNA fragments of 443 and 267 bp; 111 and 108; 113 and 12; 60 and 58; and 6 and 17 bp, respectively (Table 1). Methyl dCTP is incorporated into the DNA fragments during PCR and protects these sites from cleavage when incubated in the presence of Eam 1104I (8). This protection retains the PCR priming sites at each end of the DNA fragment and its exponential amplification during subsequent PCR. The effectiveness of methyl dCTP incorporation in protecting the internal Eam 1104I sites from cleavage is easily detected by gel analysis as described herein.

Additionally, the 430 bp DNA fragment of pNCAM contains an internal EcoR I site which is used to specifically identify this DNA fragment following SAS. To identify this DNA fragment, the DNA was incubated in the presence of EcoR I and the cleavage or lack of cleavage of the DNA fragment detected by gel analysis, as described herein. Similarly, the 853 bp DNA fragment of pNCAM contains an internal Kpn I site which is used to identify this DNA fragment.

Ligation of Adaptors to Driver and Tester DNA to Produce Adaptor.Driver and Adpator:Tester Nucleic Acid Complexes Adaptors were then ligated to the tester and driver DNA fragments. The nucleotide sequences, oligonucleotide no., and corresponding SEQ ID NOs of the adaptors are given in Tables 2 and 3. The B adaptor consisted of oligonucleotide numbers 408 and 409. The A adaptor consisted of oligonucleotide numbers 411 and 412. To anneal the oligonucleotides, 20 µg of oligonucleotide 408 and 7 µg of oligonucleotide 409 were combined in dH$_2$O, heated at 72° C. for 5 minutes, 55° C. for 5 minutes, and slowly cooled to 16° C. Twenty µg of oligonucleotide 411 and 7 µg of oligonucleotide 412 were also annealed under the same conditions.

TABLE 2

| Adaptor A (5' to 3') | Oligo-nucleotide No. | SEQ ID NO: |
|---|---|---|
| TAACTACTTATCTATGTTCTCTTCGAAGAGGCAC | 411 | 4 |
| GTGCCTCTTCGA | 412 | 5 |
| Adaptor A PCR Primers (5' to 3') | | |
| TAACTACTTATCTATGTTC*T | 413 | 28 |
| TAACTACTTATCTATGTTCT | 420 | 1 |
| ACTACTTATCTATGTTCTC*T | 414 | 29 |
| ACTACTTATCTATGTTCTCT | 421 | 2 |
| ACTTATCTATGTTCTCTTC*G | 407 | 30 |
| ACTTATCTATGTTCTCTTCG | 422 | 3 |
| ACTTATCTATGTTC*TC*TTC*G | 415 | 31 |

C* indicates a methyl dCTP at that nucleotide position.

TABLE 3

| Adaptor A (5' to 3') | Oligo-nucleotide No. | SEQ ID NO: |
|---|---|---|
| GTAGTGTAGGTCTACTAGCTCTTCGAAGAGGACT | 408 | 9 |
| AGTCCTCTTCGA | 409 | 10 |
| Adaptor B PCR Primers (5' to 3') | | |
| GTAGTGTAGGTCTACTAGC*T | 410 | 32 |
| GTAGTGTAGGTCTACTAGCT | 417 | 6 |

TABLE 3-continued

| Adaptor A (5' to 3') | Oligo-nucleotide No. | SEQ ID NO: |
|---|---|---|
| GTAGTGTAGGTCTACTAGCTC*T | 403 | 33 |
| AGTGTAGGTCTACTAGCTCT | 418 | 7 |
| GTAGGTCTACTAGCTCTTC*G | 404 | 34 |
| GTAGGTCTACTAGCTCTTCG | 419 | 8 |
| GTAGGTCTACTAGC*TC*TTC*G | 416 | 35 |

C* indicates a methyl dCTP at that nucleotide position

The sequences corresponding to these oligonucleotides may be referred to herein by their appropriate oligonucleotide number, SEQ ID NO, or by a primer number (i.e., primer 410) that is the same as the given oligonucleotide number. The CTCTTC Eam restriction site can be identified in the adaptors A and B. The primers comprise part or all of the Eam site.

The driver and tester DNA fragments were ligated simultaneously to an equal molar amount of adaptors A and B. Approximately 2 µg of tester DNA fragments were ligated to approximately 4.8 µg of adaptors A and B in 1×ligase buffer (1×ligase buffer is 50 mM tris-HCl [pH 7.5], 7 mM MgCl$_2$, 1 mM dithiothreitol [DTT] and 1 mM rATP) with 2 units of T4 DNA Ligase (Stratagene; La Jolla, Calif.) at 16° C. for 16 hours. The ligated adaptor:DNA fragments were separated from unligated adaptor and DNA fragments by purification with Centricon 100 (Amicon; Beverly, Mass.) per the manufacturer's recommended conditions. The volume of the DNA was approximately 50 µl (final DNA concentration 0.04 µg/µl). The ligated adaptor:DNA fragments were then amplified by PCR to prepare amplicons to be used in SAS.

Optimizing Incorporation of Methyl-dCTP into DNA Fragments

The concentration of methyl dCTP and PCR conditions required for optimal incorporation of the methyl dCTP resulting in protection of internal Eam 1104I sites from enzymatic cleavage was determined as follows. The tester DNA was restriction digested with Rsa I to generate DNA fragments ranging from 7 to 1769 base pairs. Approximately forty micrograms (µg) of the tester DNA was digested in 1×optimal buffer #1 (1×optimal buffer #1 is 25 mM tris-HCl [pH 7.7], 10 mM MgCl$_2$, 1 mM DTT and 30 µg/ml BSA) with 45 units of Rsa I (Stratagene; La Jolla, Calif.) at 37° C. for approximately 16 hours. The Rsa I was removed in the same manner as previously described for removal of Alu I following restriction digestion of tester and driver DNA. The DNA was resuspended in 40 µl TE to a DNA concentration of approximately 1 µg/µl. The molecular weights of the DNA fragments were visualized by ethidium bromide staining following electrophoresis of the fragments in a Visi-Gel™ separation matrix and compared to a molecular weight marker comprising φX174 genomic DNA digested with the restriction enzyme Hae III. The molecular weights of the pNCAM DNA fragments following Rsa I digestion were as expected (1769, 1170, 544, 398, 307, 191, 164, 93, 66, 48, 47 and 7 bp). The molecular weights of the pNCAM DNA fragments following Rsa I and Eam 1104I digestion are 1489, 952, 544, 363, 307, 280, 218, 191, 164, 93, 66, 48, 35, 31, 16 and 7 bp.

Adaptors were then ligated to the tester DNA fragments. The nucleotide sequence and SEQ ID NO of the adaptors and PCR primers are given in Table 4. The C adaptor consisted of oligonucleotide numbers 042 and 043. To anneal the oligonucleotides, 7.4 µg of oligonucleotide 042 and 3.0 μg of oligonucleotide 043 were combined, heated at 72° C. for 5 minutes, 55° C. for 5 minutes and slowly cooled to 16° C.

TABLE 4

| Adaptor C (5' to 3') | Oligo No. | SEQ ID NO: |
|---|---|---|
| AGGTCTACTAGCTCTTCTGAGAAGAG | 042 | 19 |
| CTCTTCTCAGAA | 043 | 20 |
| Adaptor C PCR Primers (5' to 3') | | |
| AGGTCTACTAGCTCTTCTGA | 041 | 21 |
| AGGTCTACTAGC*TC*TTC*TGA | 044 | 22 |

The tester DNA fragments were ligated to adaptor C as follows. Approximately 2 μg of tester DNA fragments were ligated to approximately 7 μg of adaptor C as previously described for the ligation of adaptors A and B. The ligated adaptor:DNA fragments were separated from unligated adaptor and DNA fragments by purification with Centricon 100 per the manufacturer's recommended conditions. The volume of the eluted DNA was approximately 50 μl (final DNA concentration 0.04 μg/μl). The ligated adaptor:DNA fragments were then amplified by PCR to determine the amount of methyl dCTP and number of cycles of PCR required for optimal incorporation of the methyl dCTP resulting in protection of internal Eam 1104I sites from enzymatic cleavage.

The optimal concentration of methyl-dCTP in the PCR was determined as follows. Solutions containing methyl-dCTP ranging from 0 to 100 mM and 10 mM each of dTTP, dATP and dGTP were prepared. To prepare a solution having a final concentration of 100 mM methyl dCTP, 86 μl of TE was added to 5 mg methyl dCTP (Pharmacia; Piscataway, N.J.). Solutions having final concentrations of 25 and 50 mM methyl-dCTP were prepared by making appropriate dilutions of the 100 mM methyl dCTP solution with TE. Solutions having a final concentration of 10 mM of dTTP, dATP and dGTP were prepared by making appropriate dilutions of the 100 mM dTTP, dATP and dGTP (Pharmacia, Piscataway, N.J.) with TE.

Amplicons comprising tester DNA fragments having methyl dCTP in the primer and either normal or methyl dCTP incorporated during the PCR were prepared as follows. PCR primer 044 contains a methyl dCTP at each of the three dCTP positions within the Eam 1104I site (Table 4). Each sample was prepared in duplicate. Five different samples having approximately 0.5 μg tester DNA having C adaptors, 200 nanograms (ng) of PCR primer 044, 2.5 units cloned Pfu DNA polymerase (Stratagene; La Jolla, Calif.), 1×cloned Pfu DNA polymerase reaction buffer (1×=100 millimolar [mM] KCl, 100 mM [NH4]SO$_4$, 200 mM Tris [pH 8.8], 20 mM MgSO4, 1% [volume/volume; v/v] Triton® X-100, 1 milligram [mg]/ml nuclease-free BSA) and 200 μM each of dGTP, dATP, dTTP and dCTP were combined in a total PCR volume of 60 μl. The PCR were overlaid with silicone oil (Sigma, St. Louis, Mo.). PCR in a RoboCycler®40 temperature cycler (Stratagene; La Jolla, Calif.) was as follows: one cycle of 72° C. for 7 minutes; one cycle of 94° C. for 5 minutes, 54° C. for 5 minutes and 72° C. for 2 minutes; and twenty cycles of 94° C. for 1 minute, 54° C. for 1 minute, and 72° C. for 2 minutes. The samples were maintained at 72° C. while an aliquot was removed and additional PCR reagents were added.

While the samples were at 72° C., 10 μl of each sample was removed for later analysis. Each PCR was divided into two equal volumes. One volume received an equal volume of 1×cloned Pfu DNA polymerase reaction buffer, 1.25 units of cloned Pfu DNA polymerase, 100 ng primer 044, and one of the following combinations of nucleotides to one of the final nucleotide concentrations given in Table 5. After the additional PCR reagents were added, 10 additional cycles of 94° C. for 1 minute, 54° C. for 1 minute, and 72° C. for 2 minutes and a single cycle of 72° C. for 10 minutes were performed.

TABLE 5

| Sample | methyl dCTP final concentration (μM) | dCTP final concentrations (μM) | dTTP, dATP, dGTP final concentrations (μM) |
|---|---|---|---|
| 1 | 0 | 100 | 200 |
| 2 | 125 | 100 | 200 |
| 3 | 250 | 100 | 200 |
| 4 | 500 | 100 | 200 |
| 5 | 1000 | 100 | 200 |

Ten μl of each PCR product was removed, 8 units of Eam 1104I were added and the sample incubated at 37° C. for 16 hours. The presence of each PCR product and the restriction digestion products was determined by VisiGel™ separation matrix electrophoresis. Each sample produced PCR products which were detectable by gel electrophoresis of the expected molecular weights between 853 and 307 bp. The results demonstrated that the lack of methyl dCTP incorporation into the tester DNA in sample 1 during PCR allowed efficient cleavage of the PCR product by Eam 1104I. Tester DNA prepared with 125 and 250 μM methyl dCTP in samples 2 and 3, respectively, was partially protected from cleavage by Eam 1104I. Tester DNA prepared with 500 and 1000 μM methyl dCTP in samples 4 and 5, respectively, was also partially protected from cleavage by Eam 1104I but less of the PCR product was generated than that generated with 125 and 250 μM methyl dCTP. The results obtained from duplicate samples were comparable.

These results indicate that incorporation of methyl-dCTP protects against cleavage of Eam 1104I and that at least partial protection from cleavage can be achieved by using final methyl-dCTP concentrations of 125 to 500 μM, during PCR. These PCR conditions and nucleotide concentrations also result in a sufficient amount of PCR product required for SAS. The applicability of these results was then determined by using DNA ligated to adaptors A and B.

PCR Extension Reaction for Methyl-dCTP Incorporation into Adaptor:Driver and Adaptor:Tester DNA Complexes The above-described experiment was repeated using tester and driver DNA ligated to adaptors A and B to produce adaptor:nucleic acid complexes (i.e., adaptor A:tester nucleic acid complexes, adaptor B:driver nucleic acid complexes, etc). In addition, the number of cycles following the addition of the methyl-dCTP was varied to determine the effect of additional cycles on the amount of PCR product obtained and the incorporation of the methyl-dCTP. Also, the effect of the position of the methyl-dCTP in the PCR primer on the efficiency of Eam 1104I cleavage of the PCR product was determined. The ability of Eam 1104I to cleave the Eam 1104I sites in the adaptor sequences which were incorporated into the PCR products during PCR was determined by incubating the PCR products with Eam 1104I under cleavage conditions and reamplifying the incubated products to determine if the priming sites had been cleaved from the PCR product.

Amplicons representing tester and driver DNA digested with Alu I were prepared by ligation of adaptors A and B and used as templates in PCR with primers having methyl-dCTP or unmodified dCTP and with methyl-dCTP or unmodified dCTP. The amplicons, were then cleaved with Eam 1104I and analyzed by gel electrophoresis to determine the ability of the incorporated methyl dCTP to protect against cleavage. Tester and driver DNA were ligated to adaptors A and B as described above in Ligation of Adaptors to Driver and Tester DNA.

Amplicons comprising driver DNA fragments having normal dCTP in the primers and normal dCTP incorporated during the PCR were prepared with three different PCR primers. None of the PCR primers used to amplify the driver DNA contained a methyl dCTP. Amplicons comprising tester DNA fragments having either unmodified or methyl-dCTP in the primer used and either normal or methyl dCTP incorporated during the PCR were prepared using three different PCR primers with normal dCTP and four PCR primers with methyl dCTP. The nucleotide sequence and corresponding SEQ ID NO are given in Tables 2 and 3. The position of the methyl-dCTP within the PCR primers containing methyl-dCTP are indicated in Tables 2 and 3 as "C*". PCR primers 413 and 410 contain a methyl-dCTP at the first dCTP position within the Eam 1104I site. PCR primers 414 and 403 contain a methyl-dCTP at the second dCTP position within the Eam 1104I site. PCR primers 407 and 404 contain a methyl-dCTP at the third dCTP position within the Eam 1104I site. PCR primers 415 and 416 contain a methyl-dCTP at each of the three dCTP positions within the Eam 1104I site.

Three different samples comprising driver DNA were prepared. Each sample contained one of the PCR primer pairs without methyl dCTP described above. Seven different samples comprising tester DNA were prepared. Each sample contained one of the PCR primer pairs with unmodified or methyl-dCTP described above. The tester DNA samples were prepared in duplicate. One of the duplicate samples was prepared with normal dCTP and the other was prepared with both normal and methyl dCTP. For the PCR, driver and tester samples having approximately 0.5 $\mu$g driver or tester DNA, respectively, having A and B adaptors, 100 ng of each PCR primer, 2.5 units cloned Pfu DNA polymerase (Stratagene; La Jolla, Calif.), 1×cloned Pfu DNA polymerase reaction buffer and 200 $\mu$M each of dGTP, dATP, dTTP and dCTP were combined in a total PCR volume of 50 $\mu$l. The PCR were overlaid with silicone oil (Sigma, St. Louis, Mo.). The PCR was as follows: one cycle of 72° C. for 7 minutes; one cycle of 94° C. for 5 minutes, 54° C. for 5 minutes and 72°C. for 2 minutes; and twenty cycles of 94° C. for 1 minute, 54° C. for 1 minute, and 72° C. for 2 minutes. The samples were maintained at 6° C. while an aliquot was removed and additional PCR reagents were added.

While the samples were at 6° C., an equal volume of 1×cloned Pfu DNA polymerase reaction buffer, 1.25 units of cloned Pfu DNA polymerase, a mixture of 200 micromolar dTTP, dGTP, dATP and dCTP was added to the driver DNA samples and one set of the tester DNA samples. The other set of tester DNA samples received an equal volume of volume of 1×cloned Pfu DNA polymerase reaction buffer, 1.25 units of cloned Pfu DNA polymerase, a mixture of 200 $\mu$M dTTP, dGTP and dATP and 500 $\mu$M methyl dCTP. Following the addition of the PCR reagents, 10 additional cycles of 94° C. for 1 minute, 54° C. for 1 minute and 72° C. for 2 minutes were performed. Ten $\mu$l of each PCR product was removed for later analysis. Ten additional cycles of 94° C. for 1 minute, 54° C. for 1 minute and 72° C. for 2 minutes and a single cycle of 72° C. for 10 minutes were then performed. Ten $\mu$l of each PCR product was removed for later analysis. Cleavage of Adptor:Driver and Adptor:Tester DNA Complexes with Eam 1104I The driver and tester DNA fragments were then digested with Eam 1104I. Eight units of Eam 1104I were added to the remaining PCR products and incubated at 37° C. for 3 hours. Five $\mu$l of the PCR products incubated with and without Eam 1104I were then reamplified by PCR using the original PCR primers used to generate the PCR product. The PCR conditions were the same as those described above for the preparation of amplicons representing driver and tester DNA having A and B adaptors with a total 20 cycles of PCR performed.

The PCR and restriction digestion products under each condition were analyzed by VisiGel™ separation matrix electrophoresis. The PCR samples include the following: 5 $\mu$l of the ten $\mu$l sample removed following the first PCR and 5 $\mu$l of the same products incubated with Eam 1104I; 10 $\mu$l of the PCR product after an additional 10 cycles of PCR which had not been incubated with Eam 1104I and 10 $\mu$l of the same sample following incubation with Eam 1104I and 10 $\mu$l of the PCR product after an additional 20 cycles of PCR which had not been incubated with Eam 1104I and 10 $\mu$l of the same sample following incubation with Eam 1104I.

The amount and number of different molecular weight PCR products generated with the driver DNA with the three different PCR primer pairs was comparable. The molecular weights of the PCR products ranged from 710 to 100 bp.

The amount of PCR product generated with the tester DNA after 20, 30 and 40 cycles of PCR demonstrate that more PCR product is generated at 40 cycles of PCR than under the other conditions tested. In addition, less of the PCR product was generated at methyl-dCTP concentrations of 1000 $\mu$M than at the other concentrations tested.

PCR products prepared from tester DNA amplified in the presence of normal dCTP and in the absence of methyl dCTP were cleaved at internal Eam 1104I sites. PCR products prepared from tester DNA amplified with both normal and methyl dCTP were only partially cleaved at internal Eam 1104I sites. The results demonstrate that the lack of methyl dCTP incorporation into the driver DNA during PCR allows efficient cleavage of the PCR products by Eam 1104I and that incorporation of methyl dCTP into the tester DNA protected against cleavage by Eam 1104I.

PCR products prepared from tester DNA with methyl-dCTP in the PCR primer in the presence of normal and methyl dCTP were reamplified more efficiently than those PCR products prepared from tester DNA without methyl dCTP in the PCR primer and in the presence of normal dCTP and the absence of methyl dCTP. In the absence of protection from cleavage at the Eam 1104I site in the PCR primer, the PCR priming site would be removed and reamplification of the tester DNA would be inefficient. When protected from cleavage at the Eam 1104I site in the PCR primer, the PCR priming site is retained and reamplification of the tester DNA is efficient. The same results were obtained with all of the methyl-dCTP-containing primers and cleavage of the Eam site is therefore independent of the position and number of the methyl-dCTP within the Eam 1104I cleavage site. Therefore, the presence of one or more methyl-dCTP in the PCR primer used to generate the PCR product was sufficient to protect against cleavage of the PCR product at the Eam 1104I site in the PCR primer.

Additionally, PCR products having internal Eam 1104I sites that were prepared in the presence of normal and methyl dCTP were only partially cleaved at the internal Eam 1104I sites. These results indicate that incorporation of methyl dCTP does protect against cleavage of Eam 1104I when the PCR product is prepared with normal and methyl dCTP. The results described above also indicate that only one methyl dCTP need be present in the Eam 1104I site to protect against cleavage with Eam 1104I. These PCR conditions and nucleotide concentrations also result in a sufficient amount of PCR product required for SAS. The tester and driver amplicons having methyl and normal dCTP, respectively, were then used in SAS.

Subtraction of Tester and Driver DNA

For subtraction of driver and tester DNA, the DNA were combined, annealed, digested with Eam 1104I, digested with S1 nuclease, reamplified and digested with EcoR I to identify the subtracted DNA species. Each of these steps is described below.

1. Annealing of Adaptor:Tester and Adaptor:Driver DNA Complexes to Produce Hybrids of Adaptor:DNA Complexes pNCAM (tester DNA) and pBluescript SK(—) (driver DNA) fragments having A and B adaptors were annealed as follows. The tester and driver DNA amplified using primers 413 and 410 and 420 and 417, respectively, were combined at molar ratios of 1:20 and 1:2000, ethanol precipitated as described above, resuspended in 3 μl dH$_2$O, denatured at 95° C. for 5 minutes, incubated at 68° C. while 3 μl of 1 M NaCl was added, and incubated at 68° C. for 16 hours. A molar ratio of 1:20 corresponds to approximately 0.5 micrograms of tester DNA to 10 micrograms driver DNA and a molar ration of 1:2000 corresponds to approximately 0.005 micrograms of tester DNA to 10 milligrams of driver DNA. The annealed tester and driver DNA were then digested with Eam 1104I to cleave at unprotected Eam 1104 sites.

2. Eam 1104I Digestion of Hybrid Adaptor:DNA Complexes Comprising the Tester and Driver DNA Fragments To digest the annealed tester and driver DNA, 6 μl 10 ×universal buffer (1×universal buffer is 0.1 M potassium acetate; 25 mM tris-acetate, pH 7.6; 10 mM magnesium acetate; 0.5 mM β-mercaptoethanol and 10 μg/ml BSA) and 53 μl dH$_2$O was added to the annealed tester and driver DNA. Eight units Eam 1104I was added and the sample incubated at 37° C. for 6 hours. During incubation of the annealed tester and driver DNA in the presence of Eam 1104I, the unprotected DNA was cleaved and protected DNA was not cleaved at the Eam 1104I sites. Cleavage of one or both Eam 1104I sites in the nucleotide sequence introduced by adaptors A and B at each end of the DNA fragments effectively separated the PCR priming sites contained therein resulting in the linear amplification of these fragments in subsequent PCR.

3. Single Stranded Nuclease Digestion

Following digestion with Eam 1104I, the samples contain a mixture of nucleic acid species. The samples comprise annealed and thus double-stranded nucleic acids including tester:tester DNA fragments, driver:driver DNA fragments and tester:driver DNA fragments. While these fragments have been incubated in the presence of Eam 1104I, the PCR priming sites have been removed from the driver:driver and tester:driver DNA fragments and thus will not be exponentially amplified in the subsequent PCR. The samples also comprise single-stranded nucleic acids including unincorporated PCR primers and unannealed tester and driver DNA fragments. Cleavage of single-stranded M13 phage vector DNA (Pharmacia; Piscataway, N.J.) having Eam 1104I sites was not detectable, therefore, single-stranded nucleic acids present in the samples are not cleaved as efficiently as double-stranded nucleic acids in the samples. Amplification of these single-stranded nucleic acids was eliminated in the subsequent PCR by removal of the PCR priming sites on the single-stranded nucleic acids by digestion with S1 nuclease. In addition, the samples may comprise hairpin loops formed when a DNA fragment has the same adaptor incorporated into each end of the DNA fragment. These adaptor sequences are homologous and can anneal to each other forming stable hairpin loops. The hairpin loops have a double-stranded portion which was formed by the annealing of the homologous sequences and a single-stranded portion which is the sequence in between the homologous sequences. S1 nuclease cleaves the single-stranded portion of this sequence and thereby eliminates exponential amplification of these single-stranded nucleic acids in the subsequent PCR by separation of the PCR priming sites contained in the homologous sequence.

To remove single-stranded DNA and DNA forming hairpin loops, the DNA were incubated in the presence of a single stranded nuclease. The S1 nuclease degrades single-stranded nucleic acids to yield 5'-phosphoryl mono- or oligonucleotides. In addition, S1 nuclease cleaves single-stranded DNA formed in hairpin loops (38). Double-stranded nucleic acids are not cleaved by S1 nuclease unless very large amounts of the enzyme are used (39). Nuclease that remove either single-stranded or double-stranded nucleic acids can be used to remove one or more of the following: unincorporated single-stranded PCR primers: single-stranded overhangs from Eam 1104I-cleaved DNA fragments to further remove the PCR priming sites; hairpin loops formed during PCR when the same PCR primer binding site is present on both ends of the DNA fragment; and any other undesired single-stranded DNA present in the sample. The suitability of a particular nuclease can be determined by practicing the methods described herein.

The DNA was digested with S1 nuclease as follows. Twenty μl DNA was combined with 10 μl 10×S1 nuclease buffer (1×S1 nuclease buffer is 30 mM NaOAc, pH 4.6; 50 mM NaCl; 1 mM ZnCl$_2$ and 5% (v/v) glycerol) and 1 unit of S1 nuclease, and the samples incubated at 30° C. for 10 minutes. To inactivate the S1 nuclease, 2 μl 1 M tris-HCl, pH 8.8 was added to each sample and the samples incubated at 93° C. for 5 minutes. To effectively change the buffer components prior to reamplification, the S1 nuclease treated samples were ethanol precipitated as described above with 1×STE (0.1 M NaCl; 20 mM Tris HCl, pH 7.5, 10 mM EDTA) and ethanol. The precipitated samples were resuspended in 20 μl dH$_2$O and reamplified to identify subtracted DNA fragments following subtraction.

4. Reamplification of DNA Fragments Following Subtraction

To identify those DNA fragments which were not subtracted from each sample, the samples were reamplified using A and B adaptor specific primers. To reamplify the samples, 5 μl of each digested DNA sample was used as the DNA template in PCR as described above. The PCR was as follows: one cycle of 93° C. for 5 minutes, 54° C. for 5 minutes and 72° C. for 2 minutes; and 30 cycles of 93° C. for 1 minute, 54° C. for 1 minutes, and 72° C. for 2 minutes; followed by a single cycle of 72° C. for 10 minutes. PCR products were then incubated with EcoR I. Fifteen μl of the PCR products were incubated with 20 units of EcoR I at 37° C. for 1 hour. The presence of each PCR product and cleavage products was determined by VisiGel™ separation matrix electrophoresis.

The results of reamplification of the digested driver and tester DNA fragments to identify those DNA fragments which were not subtracted from the DNA population are as follows. Amplification of samples at a tester:driver ratio of 1:20, which were digested with Eam 1104I and 1 unit of S1 nuclease resulted in the detection of driver and tester DNA fragments. The DNA fragments of 853, 710, and 430 base pairs were detected. The 710 bp DNA fragment is common to the tester and driver nucleic acids. The 853 and 430 bp DNA fragments are unique to the tester nucleic acid.

5. EcoR I Digestion to Confirm Subtraction

The identity of one of the tester DNA fragments was confirmed by cleavage of the DNA when incubated in the presence of EcoR I, as the sequence contained an internal EcoR I site.

These results demonstrate that substantially all of the DNA fragments common in a tester and driver population have been subtracted from that population and that unique DNA fragments present only in a tester DNA population have been amplified following the teachings described herein.

Thus, as is evident from the results above, the general switched adaptor subtraction method (SAS) has several advantages over representational difference analysis (RDA). First, there is no need for two rounds of adaptor ligations as in RDA. Only one set of adaptors is needed for both the primary PCR amplification and the subsequent selective PCR amplification. RDA also requires a restriction digestion to remove the first set of primers, but does not protect the internal tester DNA sequences from cleavage with the restriction enzyme used in this digestion step. Thus, tester DNA containing an internal sequence of the restriction enzyme site used in the primers will be lost during RDA.

Furthermore, RDA allows tester:driver molecules to be amplified linearly, causing unwanted competition with the target molecules for primers, enzyme, and dNTPs. The PCR amplification of target nucleic acids is thus less efficient. SAS, on the other hand, eliminates tester:driver and driver::driver hybrids from competition during PCR by removing their primer binding sites. In the methods of this invention, only hybrids comprising adaptor:tester nucleic acid complexes, the set of desired molecules, can be properly primed for replication or amplification.

Preparation of Modified Adaptors and Primers: General Considerations

The modified adaptors and/or primers used in the invention can be produced by numerous methods known in the art. Some modified nucleotides can be purchased through commercial suppliers, such as Stratagene, Pharmacia, or Sigma-Aldrich, and many are well known in the art. Beyond the methylated and biotinylated modifications specifically mentioned, one skilled in the art can readily determine the ability of any modified nucleotide to function in the adaptors and primers of this invention. In addition, the modified nucleotides can be produced and incorporated into an adaptor sequence by known chemical techniques (22) and known enzyme polymerization techniques. For example, dC-me phosphoramidite 5-methyl-2'-deoxycytidine (Glen Research; Sterling, Va.) can be incorporated into any primer or adaptor in a conventional nucleotide synthesizer, Applied Biosystems 381A DNA Synthesizer (Applied Biosystems) to produce oligonucleotides having a 5-methyl-dCTP. Methylated cytosine, 5-methyl cytosine, 5-methyl-dCTP, and methyl dCTP referred to herein all represent a 5-methyl-2'-deoxycytidine modification.

One of skill in the art will recognize that the upper strand of the adaptors can also be used as a PCR primer to prepare tester and driver DNA for use in SAS. In preparing tester DNA using the upper strand of the adaptor as a primer, the adaptor will contain 5'-methyl-dCTP in the Eam recognition sequence as described herein for the primer.

The principles involved in designing an appropriate adaptor for use in this invention are also well known in the art. The region of the adaptor that anneals to the amplification primer can preferably be about 10 to about 30 nucleotides in length. However, one skilled in the art can readily determine the ability of any selected adaptor size to accommodate a replication or amplification reaction. Thus, any size adaptor can be designed by one skilled in the art depending on the desired characteristics.

EXAMPLE 2

Normalization of Samples Using Switched Adaptor Subtraction

Figure 2A:
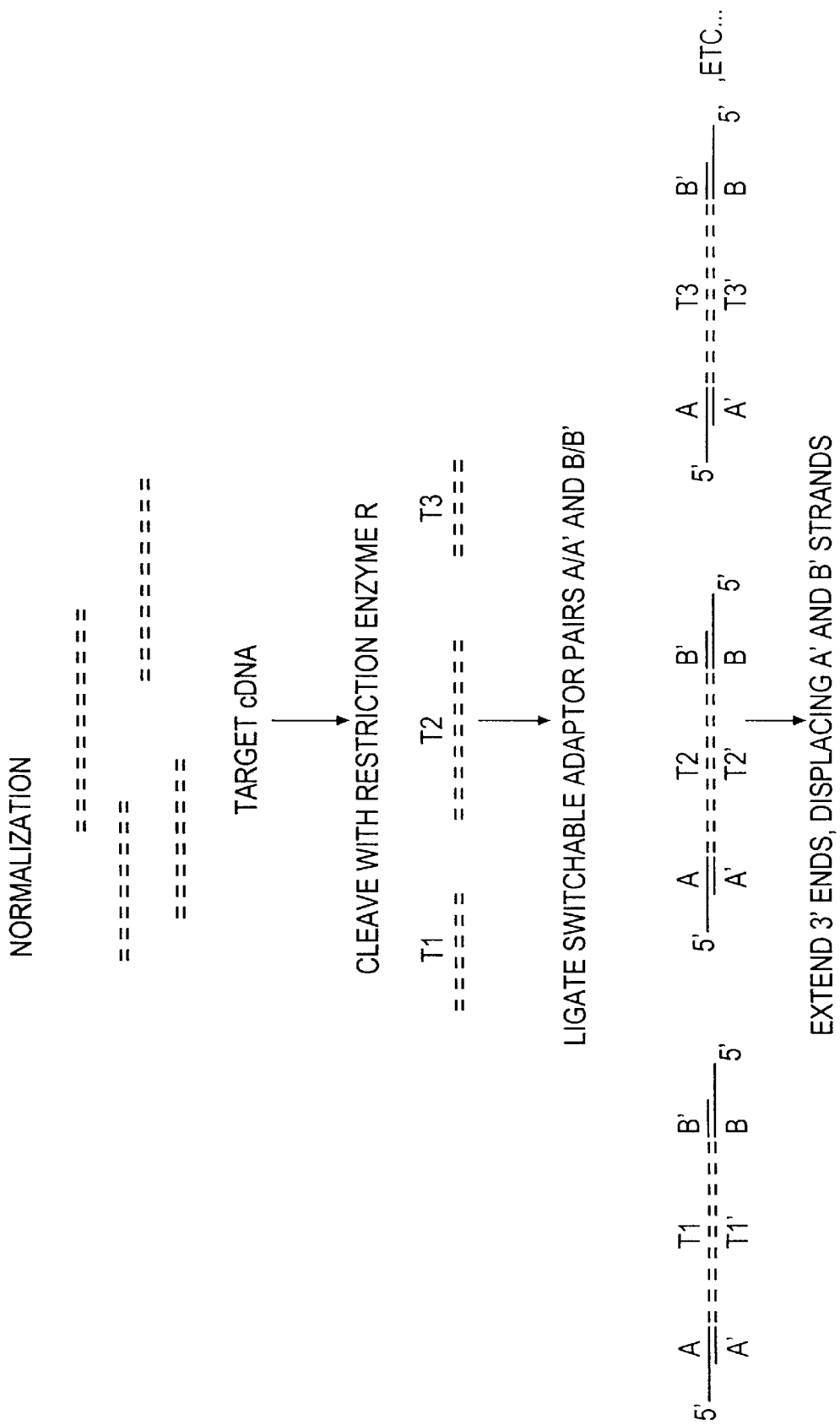
FIGS. 2A–2C: Normalization method using a cDNA sample.
Figure 2B:
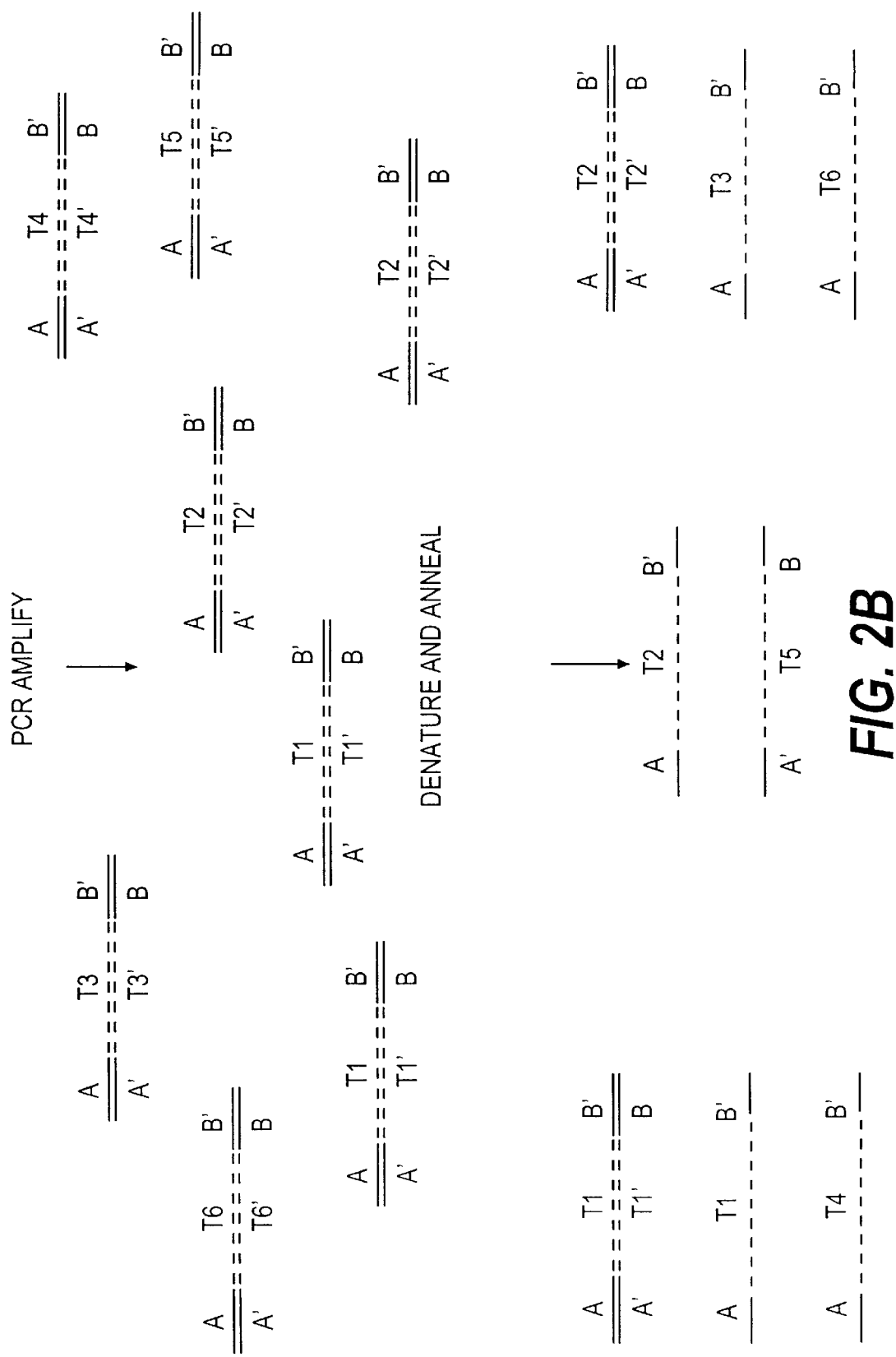
Figure 2C:
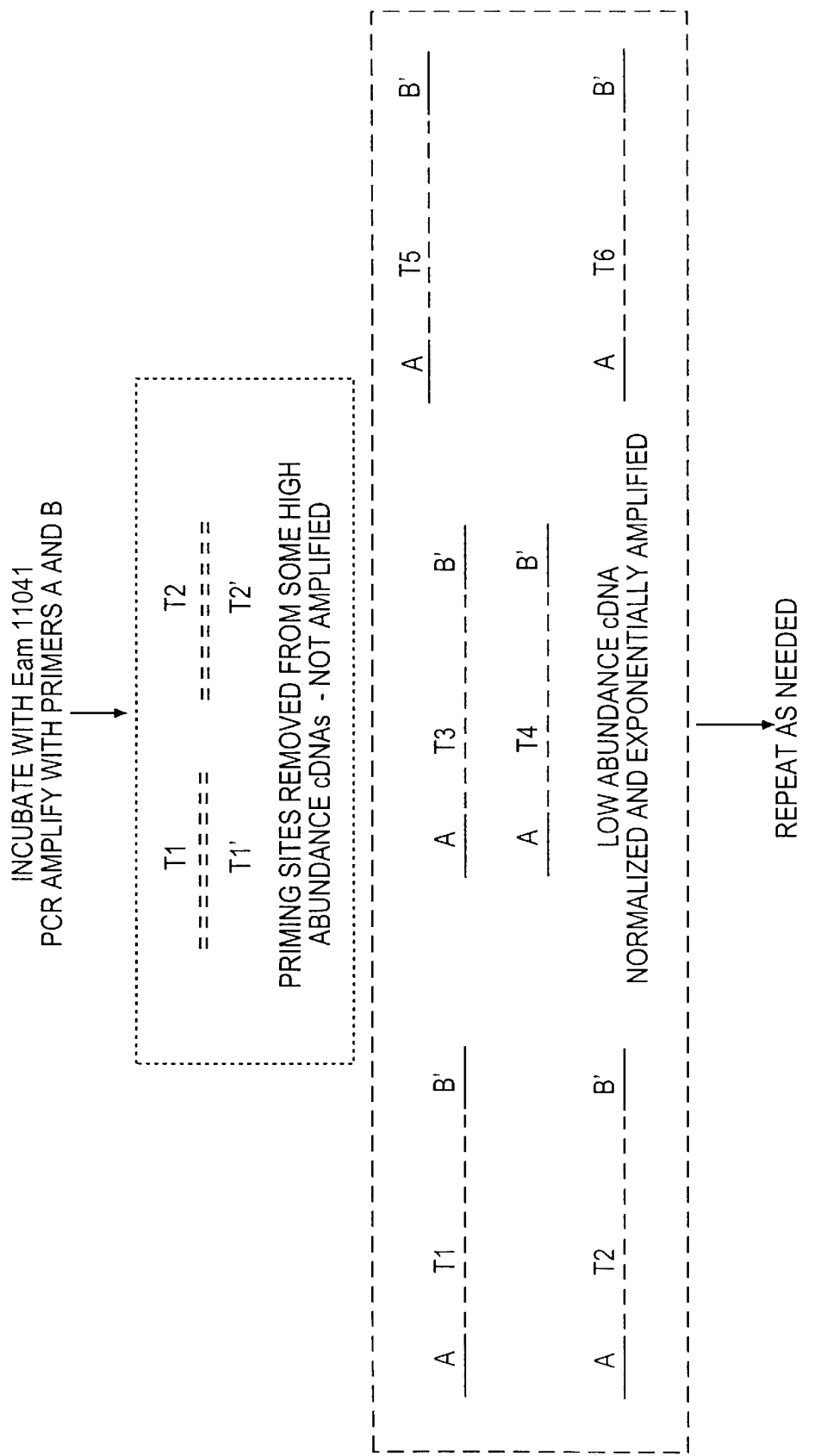
Figure 3A:
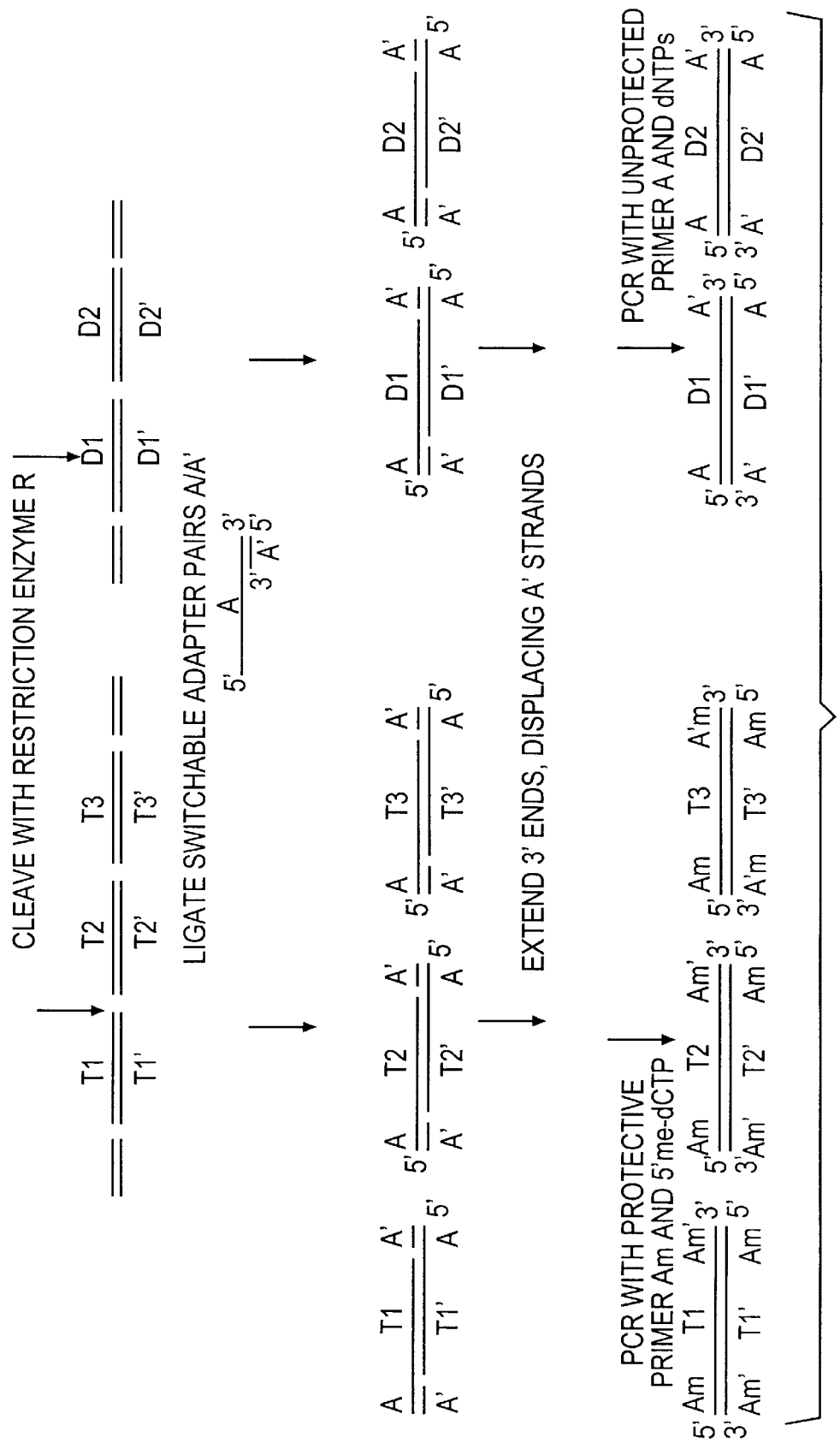
FIG. 3: A general outline of the switched adaptor subtraction method. Populations of tester (T) and driver (D) nucleic acids are shown to contain two sequences in common (T1 is the same sequence as D1, and T2 is the same sequence as D2) plus a unique sequence, T3 (target or desired nucleic acid), found only in the tester population. The designation (Am) means adaptor strand A with 5-methyl-2'-deoxycytidine modified nucleotides at C bases in the Eam 1104 I recognition sequence. A'm is the strand complementary to strand A, also having a modification at C bases in the Eam1104 I recognition sequence.
Figure 3B:
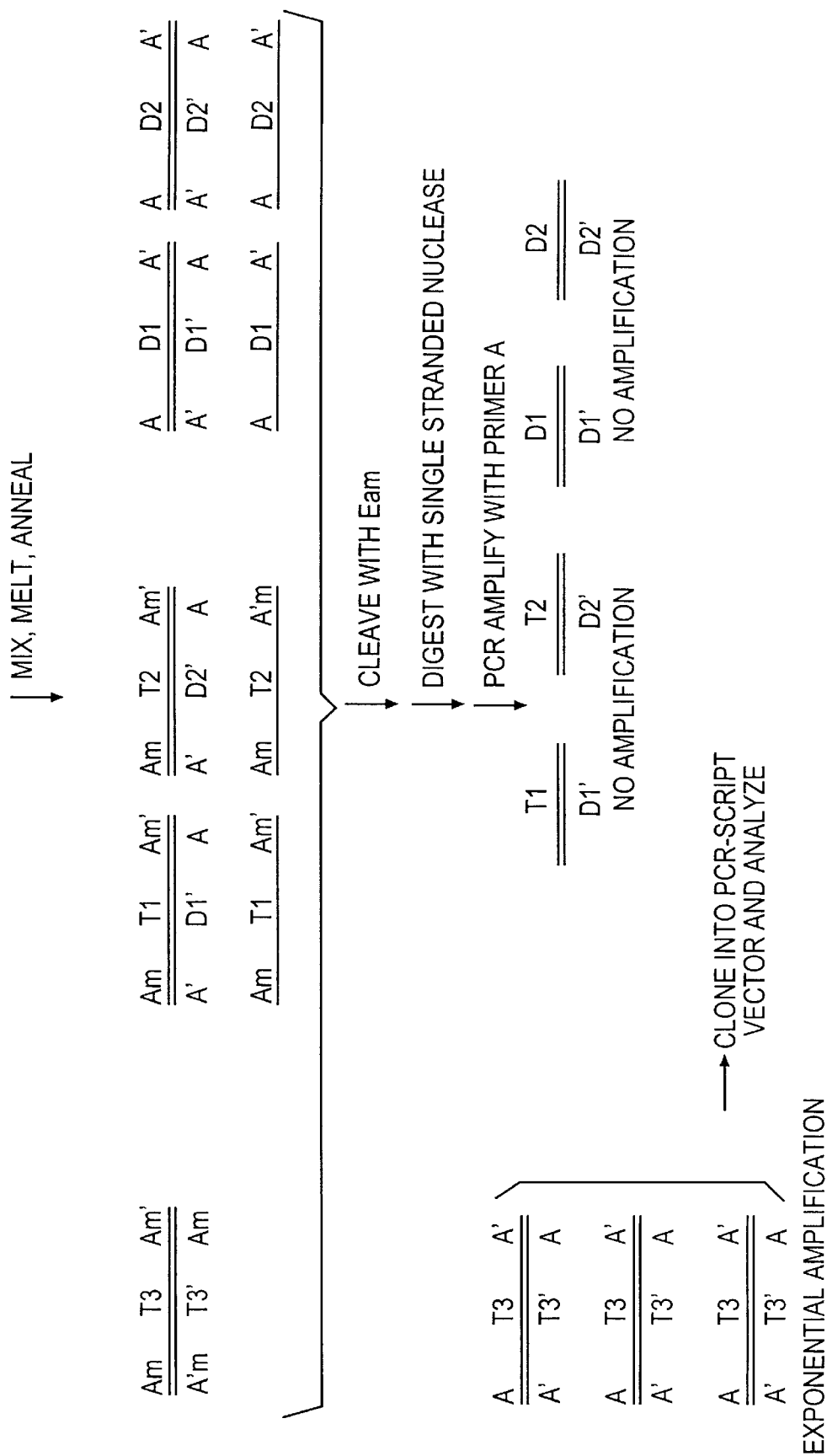

Perhaps one of the most powerful advantages of SAS over other methods is the ability to perform DNA normalization prior to subtraction, without using physical separation methods (see FIG. 2). In a preferred embodiment of the normalization method, the nucleic acid sample is prepared and ligated to the adaptors having a cleavage site, as before. One or more modified nucleotides may be incorporated into a sample. The nucleic acids are denatured and then annealed for a period of time that is generally insufficient for the least abundant species in the population to re-anneal and sufficient for the most abundant species to re-anneal. The percentage of hybridization can be varied by adjusting the hybridization time, for example. One skilled in the art is familiar with detection and monitoring techniques in order to readily determine the appropriate times and conditions for combining particular nucleic acid sequences used in order to form hybrids (23, see also references 15–21).

During hybridization, DNA species of high abundance re-annealed and thus form double-stranded DNA. After hybridization, the DNA is then treated with a cleaving enzyme, for example, Eam (8), to remove the adaptors from any double-stranded DNA and thus interfere with the amplification of highly abundant DNA. During hybridization, DNA species of lower abundance re-annealed less often and thus remain as single-stranded DNA. Since Eam cleaves single-stranded DNA at a lower efficiency than double-stranded DNA, the cleavage reaction will not remove the adaptors sequences from any single-stranded DNA and thus not interfere with the amplification of lower abundant DNA. Repeated application of this process produces the desired result, which is normalization of the population.

Most normalization procedures involve repeated hybridizations. In theory, the abundance can only be enriched N-fold in each hybridization cycle, wherein N is the molar excess of driver placed in the hybridization reaction. If the normalized product from the first cycle is re-normalized, there should be an $N^2$ fold theoretical enrichment. Thus, two or three cycles are preferably performed. Some have discussed a need for from five to twenty subtractions in previous methods (15).

With the SAS method, the PCR product from the first normalization cycle may be placed through the normalization procedure again. The final normalized population is then ready for the SAS method, above, since the adaptors used for normalization can be the same as those used for SAS. The ease and simplicity of performing normalization prior to SAS makes the methods of the invention very powerful and advantageous relative to RDA and other related methods.

An alternative normalization method involves preparing the DNA and ligating the same adaptors. The DNA is then divided into two samples. One or more modified nucleotides are incorporated into one sample (tester) and normal nucleotides are incorporated into the other (driver). The tester population is then mixed with a large excess of the driver (7). The DNA is denatured and then annealed for a period of time that is generally insufficient for the lowest abundance species in the tester population to re-anneal to other tester molecules (tester:tester hybrids) but will preferably allow about 50% of the lowest abundant species in the driver population to re-anneal (either with another driver molecule or with a tester molecule). The percentage of hybridization can be varied by adjusting the hybridization time, for example. One skilled in the art is familiar with detection and monitoring techniques in order to readily determine the appropriate times and conditions for combining particular nucleic acid sequences used in order to form hybrids (23, see also references 15–21).

After hybridization, the DNA is then treated with the cleaving enzyme, for example Eam (8). Since the modified nucleotides incorporated into the tester sample will protect the adaptor from Eam cleavage, the cleavage reaction will remove the adaptors from any double-stranded molecule for which at least one adaptor strand is derived from the driver population. Tester:tester hybrids will survive, but since the annealing is performed in a large excess of driver (for example, 100:1), approximately 99% of any tester molecule that is in high enough concentration to anneal will end up as a tester:driver hybrid. Tester molecules that are rare enough not to anneal to either tester or driver will also survive since the Eam will not cleave methylated single stranded DNA. Most tester molecules will end up as tester:driver hybrids and be removed from the amplifiable population. A small fraction of high abundance tester will survive and most of the lowest abundance tester will survive. This produces the desired result, which is normalization of the population.

As above, the resulting desired population, from a first normalization cycle, can be divided into two populations and placed through the normalization procedure again. Since the methylation of the DNA is in effect reversible, by PCR amplification with normal dNTP's, tester and driver populations, can be regenerated from the end product of a normalization cycle. The final normalized population is ready for the SAS subtractive hybridization protocol since the adaptors used for normalization can be the same as those used for the subtraction protocol. One need not worry about using non-normalized driver populations for subtraction, since the driver is used in large molar excess. Also, non-hybridized single-stranded driver molecules are not a problem in the subtractive protocol since a single-stranded nuclease can optionally be used to remove these prior to the PCR step. There is no such single stranded nuclease step in the prior normalization protocols. The ease and simplicity of pre-subtraction normalization makes SAS very powerful and advantageous relative to RDA and other prior methods.

The specific embodiments described herein should not be construed as limiting the scope of this invention. Instead, they are representative of the methods, adaptors, kits, and assays that one skilled in the art can make and use in conjunction with the disclosed invention. In addition, the cleavage techniques that may be used in the methods of this invention can include chemical cleavage agents instead of restriction enzymes, see for example (30). Representative chemical cleavage techniques are known in the art. The enzymes used to cut particular sequences in the nucleic acids may also be chimeric proteins, such as an appropriate DNA binding domain operably linked to a cleavage domain (29). One skilled in the art could modify any sequence-specific cleavage technique with the methods and primers of this invention. Finally, the disclosure in this application enables one skilled in the art to make and use the claims that follow.

References

The following references are specifically incorporated into the contents of this disclosure by reference. In addition, one skilled in the art can use the teachings of these references in order to more easily make and use certain embodiments of the disclosed invention.

1. Lamar, E. E. and Palmer, E. Cell 37:171 (1984)
2. Kunkel, L. M., Monaco, A. P., Middlesworth, W, Ochs, H. D., and Latt, S. A. Proc. Natl. Acad. Sci. USA 82:4778 (1985).
3. Nussbaum, R. L., Lesko; J. G., Lewis, R. A., Ledbetter, S. A., and Ledbetter, D. H. Proc. Natl. Acad. Sci. USA 84:6521 (1987).
4. Lisitsyn, N., Lisitsyn, N., and Wigler, M. Science 259: 946 (1993).
5. Hubank, M. and Schatz, D. G. Nucl. Acids Res. 22: 5640 (1994).
6. Hou, P., Want, Z. H., Wang, X. Q., and Wu, M. Nucl. Acids Res. 24: 2196 (1996).
7. Suzuki, Y., Sato, N., Tohyama, M., Wanaka, A., and Takagi, T. Nucl. Acids Res. 24: 797 (1996).
8. Padgett, K. and Sorge, J. Gene 168:31–35 (1996).
9. Lukyanov, K. A., Matz, M. V., Bogdanova, E. A., Gurskaya, N. G., and Lukyanov, S. A. (1996) Nucl. Acids Res. 24: 2194.
10. Wieland, I., Bolge, G., Asouline, G. & Wigler, M. (1990) Proc. Natl. Acad. Sci. U.S.A. 87: 2720–2724.
11. Liang, P. & Pardee, A. B. (1992) Science 257: 967–971.
12. Lisitsyn, N., Lisitsyn, N. & Wigler, M. (1993) Science 259: 946–951.
13. Bishop, D. T., Williamson, J. A. & Skolnick, M. H. (1983) Am. J. Hum. Genet. 35: 795–815.
14. Alberts, B. et al. (1983) Molecular Biology of the Cell, Garland Publishing, Inc., New York.
15. Ausubel, F. M., et al. (1989) Current Protocols in Molecular Biology, Greene Publishing Associates and Wiley-Interscience, New York (and especially Supplement 34 (1996) "PCR-Based Subtractive cDNA Cloning").
16. Kievits, T., et al. (1991) J. Virological Meth. 35: 273–286.
17. Erlich, H. A., ed., *PCR Technology*, W. H. Freeman and Company (1992).
18. Innis, M. A. Gelfand, D. H., Sninski, J. J., and White, T. J. eds., *PCR Protocols*, Academic Press (1990). Innis, M. A., Gelfand, D. H. and Sninski, J. J. eds., *PCR Strategies*, Academic Press (1995). U.S. Pat. Nos. 4,683,195; 4,683, 202; 4,800,159; 4,965,188; 4,889,818; 5,075,216; 5,079, 352; 5,104,792; 5,023,171; 5,091,310; and 5,066,584.
19. Shah et al., (1995) Journal of Medical Micro., 33(6): 1435–41.
20. Stillman et al., (1994) PCR Methods and Applications, 3(6): 320–31.
21. Schochetman, G. and Sninsky, J. J., Direct Detection of HIV Infection Using Nucleic Amplification Techniques, In: *AIDS Testing: A Comprehensive Guide*, Schochetman and George, eds., Springer-Verlag (1994).
22. Eckstein, ed. *Oligonucleotides and Analogues: A Practical Approach*, IRL Press (1992).
23. Mathieu-Daudé, F., Welsh, J., Vogt, T., and McClelland, M. (1996) DNA Rehybridization During PCR: the '$C_0t$ effect' and its Consequences, Nucl. Acids Res. 24: 2080–2086.
24. McClelland, M., Nelson, M., and Raschke, E. (1994) Effect of Site-Specific Modification on Restriction Endonucleases and DNA Modification Methyltransferases, Nucl. Acids Res. 22: 3640–3659.
25. Maniatis et al. (1983) Molecular Cloning: A Laboratory Manual, Cold Spring Harbor Laboratory Press, Cold Spring Harbor, N.Y.; and Sambrook, J., et al. (1989)

Molecular Cloning: A Laboratory Manual, 2nd Ed., Cold Spring Harbor Laboratory Press, Cold Spring Harbor, N.Y.
26. Costes, B. et al. Psoralen-modified oligonucleotide primers improve detection of mutations by denaturing gradient gel electrophoresis and provide an alternative to GC-clamping, Hum. Mol. Genet. 2(4) 393–397 (1993).
27. Guillo, L. A. et al, Selective thymine dimerization during UVA irradiation in the presence of a saturated pyridopsoralen, Photochem. Photobiol. 61(4) 331–335 (1995).
28. Straus, D. and Ausubel, F. M., Proc. Natl. Acad. Sci. USA 87: 1889 (1990).
29. U.S. Pat. Nos. 4,665,184, 4,942,227, and 5,436,150.
30. Oakley et al. (1994) Bioconjug. Chem. 5: 242–247.
31. Improved Primer-Mediated Polynucleotide Synthesis and Manipulation Techniques, Sorge & Padgett, U.S. Ser. No. 713,404, filed Sep. 13, 1996.
32. Hampson et al., (1992) Nucleic Acids Res. 20(11): 2899.
33. Riley et al. (1990) Nucleic Acids Res. 18(10): 2887.
34. U.S. Pat. No. 5,565,340.
35. Wong, K. K. and McClelland, M. (1991) PCR with 5-methyl-dCTP replacing dCTP. Nucleic Acids Res. 19: 1081.
36. Landgraf, A. et al. (1991) Quantitative analysis of polymerase chain reaction (PCR) products using primers labeled with biotin and a fluorescent dye. Anal. Biochem. 193: 231.
37. Ausubel, F. M., et al. (1989) Current Protocols in Molecular Biology, Greene Publishing Associates and Wiley-Interscience, New York; Sambrook, J., et al. (1989) Molecular Cloning. A Laboratory Manual, 2nd Ed., Cold Spring Harbor Laboratory Press, Cold Spring Harbor, N.Y.
38. Maniatis, T. et al. (1976) Cell 8: 163.
39. Vogt, V. M., (1973) Eur. J. Biochem. 33: 192.

What is claimed is:

1. A method for preferentially replicating one or more desired nucleic acids comprising:

preparing tester nucleic acids and driver nucleic acids from selected populations of nucleic acids;

producing adaptor:driver nucleic acid complexes with said driver nucleic acids, wherein each adaptor:tester nucleic acid complex comprises a tester nucleic acid and a first selected adaptor, wherein the first selected adaptor comprises a priming site;

producing adaptor:driver nucleic acid complexes with said driver nucleic acids, wherein each adaptor:driver nucleic acid complex comprises a driver nucleic acid and a second selected adaptor, and said first and second adaptors being the same or different;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:tester nucleic acid complexes;

adding a reagent capable of interacting with said first or second selected adaptor substantially prevent replication of all but double-stranded adaptor:tester nucleic acid complexes; and replicating said double-stranded adaptor:tester nucleic acid complexes.

2. The method of claim 1 wherein said selected adaptors comprise a nucleotide sequence having a cleavage recognition site capable of being recognized by said reagent.

3. The method of claim 2 wherein said cleavage recognition site is a restriction enzyme recognition site.

4. The method of claim 3 wherein said reagent is a restriction enzyme.

5. The method of claim 4 further comprising extending either said adaptor:tester nucleic acid complexes or said adaptor:driver nucleic acid complexes with a selected primer.

6. The method of claim 5 wherein said adaptor:tester nucleic acid complexes are extended with a selected modified nucleotide.

7. The method of claim 6 wherein said selected primer comprises said selected modified nucleotide.

8. The method of claim 6 or 7 wherein said selected modified nucleotide substantially protects double-stranded adaptor:tester nucleic acid complexes from cleavage by said restriction enzyme.

9. The method of claim 5 wherein said adaptor:driver nucleic acid complexes are extended with a selected modified nucleotide.

10. The method of claim 9 wherein said selected primer comprises said selected modified nucleotide.

11. The method of claim 9 or 10 wherein said selected modified nucleotide substantially permits cleavage of all but double-stranded adaptor:tester nucleic acid complexes by said restriction enzyme.

12. The method of claim 6 or 7 wherein said restriction enzyme recognition site possesses a first strand and a second complementary strand, wherein said first strand lacks a specific nucleotide base present in said second complementary strand and the presence of said selected modified nucleotide protects against cleavage by said restriction enzyme.

13. The method of claim 7 wherein said restriction enzyme recognition site possesses a first strand and a second complementary strand and is recognized by a restriction enzyme capable of cleavage when said selected modified nucleotide is present in one of said first or second strands of said restriction enzyme recognition site but substantially incapable of cleavage when said selected modified nucleotide is present in both of said first and second strands.

14. The method of claim 6 wherein said adaptor comprises a restriction enzyme recognition site possessing a first strand and a second complementary strand and is recognized by a restriction enzyme substantially incapable of cleavage when a selected modified nucleotide is present in either of said first or second strands.

15. The method of claim 9 or 10 wherein said restriction enzyme recognition site possesses a first strand and a second complementary strand and is recognized by a restriction enzyme capable of cleavage when said selected modified nucleotide is present in either one or both of said strands but substantially incapable of cleavage when said selected modified nucleotide is not present in either of said first or second strands.

16. A method for preferentially replicating one or more desired nucleic acids comprising:

preparing tester nucleic acids and driver nucleic acids from selected populations of nucleic acids;

producing adaptor:tester nucleic acid complexes with said tester nucleic acids, wherein each adaptor:tester acid complex comprises a tester nucleic acid and a first selected adaptor, wherein the first selected adaptor comprises a priming site;

producing adaptor:driver nucleic acid comprises with said driver nucleic acids, wherein each adaptor:driver nucleic acid complex comprises a driver nucleic acid and a second selected adaptor, and said first and second adaptors being the same or different;

extending either said adaptor:tester nucleic acids or said adaptor:driver nucleic acids with a selected primer and a selected modified nucleotide;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes;

adding a reagent capable of interacting with nucleic acid complexes to substantially prevent replication of all but double-stranded adaptor:tester nucleic acid complexes; and replicating said double-stranded adaptor:tester nucleic acid complexes.

17. A method for preferentially amplifying one or more desired nucleic acids comprising:

preparing tester nucleic acids and driver nucleic acids from selected populations of nucleic acids;

producing adaptor:tester nucleic acid complexes with said tester nucleic acids, with each adaptor:tester nucleic acid complex comprises a tester nucleic acid and a first selected adaptor, wherein the first selected adaptor comprises a priming site;

producing adaptor:driver nucleic acid complexes with said driver nucleic acids, wherein each adaptor:driver nucleic acid complex comprises a driver nucleic acid and a second selected adaptor, and said first and second adaptors being the same or different;

extending either said adaptor:tester nucleic acid complexes or said adaptor:driver nucleic acid complexes with a selected primer and a selected modified nucleotide;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes;

adding a reagent capable of interacting with nucleic acid complexes to substantially prevent amplification of all but double-stranded adaptor:tester nucleic acid complexes; and ampliying said double-stranded adaptor:tester nucleic acid complexes.

18. A method for preferentially amplifying one or more desired nucleic acids comprising:

preparing tester nucleic acids and driver nucleic acids from selected populations of nucleic acids;

producing adaptor:tester nucleic acid complexes with said tester nucleic acids, wherein each adaptor:tester nucleic acid complex comprises a tester nucleic acid and a first selected adaptor, wherein the first selected adaptor comprises a first priming site;

producing adaptor:driver nucleic acid complexes with said driver nucleic acids, wherein each adaptor:driver nucleic acid complex comprises a driver nucleic acid and a second selected adaptor, wherein the second selected adaptor comprises a second priming site, and said first and second adaptors being the same or different;

amplifying said adaptor:tester nucleic acid complexes with a first set of nucleotides and a first selected primer;

amplifying said adaptor:driver nucleic acid complexes with a second set of nucleotides and a second selected primer, wherein either said first selected primer or said second selected primer comprises at least one modified nucleotide;

combining said adaptor:tester nucleic acid complexes and said adaptor:driver nucleic acid complexes, thereby producing hybrid double-stranded nucleic acids comprising double-stranded adaptor:tester nucleic acid complexes, double-stranded adaptor:driver nucleic acid complexes, and double-stranded adaptor:tester/adaptor:driver nucleic acid complexes;

adding a reagent capable of interacting with nucleic acid complexes to substantially prevent amplification of all but double-stranded adaptor:tester nucleic acid complexes; and amplifying said double-stranded adaptor:tester nucleic acid complexes.

19. A method for preferentially replicating one or more sired nucleic acids comprising:

preparing tester nucleic acids and driver nucleic acids from selected populations of nucleic acids;

producing adaptor:tester nucleic acid complexes with said tester nucleic acids, wherein each adaptor:tester nucleic acid complex comprises a tester nucleic acid and a first selected adaptor, wherein the first selected adaptor comprises a priming site;

producing adaptor:driver nucleic acid complexes with said driver nucleic acids, wherein each adaptor:driver nucleic acid complex comprises a driver nucleic acid and a second selected adaptor, wherein said second selected adaptor comprises a site recognized by a selected reagent capable of substantially preventing replication of double-stranded adaptor:driver nucleic acid complexes, and wherein said first selected adaptor is non-homologous to said second selected adaptor;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes;

adding a selected reagent capable of interacting with nucleic acid complexes to substantially prevent replication of said double-stranded adaptor:tester nucleic acid complexes;

adding a nuclease capable of substantially cleaving single stranded nucleic acid complexes; and replicating double-stranded adaptor:tester nucleic acid complexes.

20. A method for detecting the presence or absence of a desired nucleic acid comprising the method of claim 16, 17, 18 or 19, and further comprising contacting a probe capable of hybridizing to said desired nucleic acid and identifying hybridized probe to detect the presence of replicated or amplified double-stranded nucleic acids.

21. A method for normalizing a sample of nucleic acids by preferentially amplifying nucleic acids present in the sample in lower abundance than nucleic acids present in the sample in higher abundance, comprising:
   (a) producing complexes each comprising a selected adaptor or adaptors and a nucleic acid in the sample, wherein the selected adaptor or adaptors comprise a priming site;
   (b) denaturing the complexes of (a) followed by combining under conditions where a relatively higher proportion of nucleic acids present in higher abundance are in double-stranded form and a relatively lower proportion of nucleic acids present in lower abundance are in single-stranded form;
   (c) adding a reagent capable of interacting with nucleic acid complexes to substantially prevent amplification of all but single-stranded nucleic acids; and
   (d) amplifying said single-stranded nucleic acid complexes.

22. A method for designing an adaptor useful for the preferential replication or amplification of desired nucleic acids comprising selecting a restriction enzyme recognition site that is substantially cleaved or substantially incapable of cleavage by a restriction enzyme depending on the presence or absence of a selected modified nucleotide in said restriction enzyme recognition site and producing a first nucleic acid comprising said restriction enzyme recognition site and a second nucleic acid complementary to at least a portion of said first nucleic acid.

23. An adaptor useful for the preferential replication or amplication of desired nucleic acids in a nucleic acid replication or amplification process comprising a restriction recognition site, wherein the sequence of nucleotides of single-stranded or double-stranded copies of said adaptor comprises a region capable of permitting replication or amplificaion or capable of substantially preventing replication or amplification depending on the presence or absence of a selected modified nucleotide or the incorporation of a selected modified nucleotide into copies of said adaptor, and a priming site.

24. The adaptor of claim 23 wherein said restriction enzyme recognition site possesses a first strand and a second complementary strand, wherein said first strand lacks a specific nucleotide base present in said second complementary strand and the presence of a selected modified nucleotide protects against cleavage by a restriction enzyme.

25. The adaptor of claim 23 wherein said restriction enzyme recognition site possesses a first strand and a second complementary strand and is recognized by a restriction enzyme capable of cleavage when a selected modified nucleotide is present in one of said first or second strands but substantially incapable of cleavage when said selected modified nucleotide is present in both of said first and second strands.

26. The adaptor of claim 23 wherein said restriction enzyme recognition site possesses a first strand and a second complementary strand and is recognized by a restriction enzyme substantially incapable of cleavage when a selected modified nucleotide is present in either of said first or second strands.

27. The adaptor of claim 23 wherein said restriction enzyme recognition site possesses a first strand and a second complementary strand and is recognized by a restriction enzyme capable of cleavage when a selected modified nucleotide is present in either one or both of said strands but substantially incapable of cleavage when said selected modified nucleotide is not present in either of said first or second strands.

28. A plurality of adaptors useful for the preferential replication or amplification of desired nucleic acids in a nucleic acid replication or amplification process wherein at least one of said adaptors comprises a nucleotide sequence capable of being cleaved by a restriction enzyme, wherein at least one of said adaptors comprises a region which is non-homologous to another of said adaptors, and wherein at least of aid adaptors comprises a priming site.

29. A plurality of adaptors of claim 28 wherein one of said adaptors is capable of being ligated to the ends of tester nucleic acids from a selected population and one of said adaptors is capable of being ligated to the ends of driver nucleic acids from a selected population, so that said adaptor capable of being ligated to tester nucleic acids is non-homologous to said adaptor capable of being ligated to driver nucleic acids.

30. A plurality of adaptors of claim 29 wherein a first and second of said adaptors are capable of being ligated to the ends of said tester nucleic acids, a third and fourth of said adaptors are capable of being ligated to the ends of said driver nucleic acids, and wherein either or both of said third and fourth adaptors comprises a cleavage site and wherein said first and second adaptors are non-homologous to said third and fourth adaptors.

31. A kit for preferentially replicating or amplifying one or more desired nucleic acids comprising one or more selected adaptors, one or more selected primers, a reagent capable of interacting with said one or more selected adaptors so as to substantially prevent replication or amplification of all but double-stranded desired nucleic acid complexes, and reagents for replicating or amplifying said double-stranded desired nucleic acid complexes.

32. A kit for preferentially replicating or amplifying one or more desired nucleic acids comprising one or more selected adaptors of claim 23, 24, 25, 26, 27, 28, 29 or 30, one or more selected primers, a cleavage reagent, and reagents for replicating or amplifying double-stranded desired nucleic acid complexes.

33. A method for preferentially replicating one or more desired nucleic acids comprising:
   preparing tester nucleic acids and driver nucleic acids from selected populations of nucleic acids;
   producing adaptor:tester nucleic acid complexes with said tester nucleic acids, wherein each adaptor:tester nucleic acid complex comprises one of (i) a tester nucleic acid with a first selected adaptor on each end, (ii) a tester nucleic acid with a second selected adaptor on each end, and (iii) a tester nucleic acid with a first selected adaptor on one end and a second selected adaptor on the other end, wherein the first selected adaptor comprises a first priming site and the second selected adaptor comprises a second priming site;
   producing adaptor:driver nucleic acid complexes with said driver nucleic acids, wherein each adaptor:driver nucleic acid complex comprises one of (i) a driver nucleic acid with a third selected adaptor on each end, (ii) a driver nucleic acid with a fourth selected adaptor on each end, and (iii) a driver nucleic acid with a third selected adaptor on one end and a fourth selected adaptor on the other end; wherein said third adaptor comprises a first cleavage recognition site and said fourth selected adaptor comprises a second cleavage recongnition site, and wherein said first and second selected adaptors are non-homologous to said third and fourth selected adaptors;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes;

adding a selected reagent that recongnizes said first and second cleavage recognition sites and cleaves double-stranded adaptor:driver nucleic acid complexes;

adding a nuclease capable of substantially cleaving single stranded nucleic acid complexes; and replicating double-stranded adaptor:tester nucleic acid complexes.

34. A method for preferentially replicating one or more desired nucleic acids comprising:

preparing tester nucleic acids and driver nucleic acids from selected populations of nucleic acids;

producing adaptor:tester nucleic acid complexes with said tester nucleic acids, wherein each adaptor:tester nucleic acid complex comprises a tester nucleic acid and a first selected adaptor, wherein said first selected adaptor comprises a region which permits selective replication of tester nucleic acids and the first selected adaptor comprises a priming site;

producing adaptor:driver nucleic acid complexes with said driver nucleic acids, wherein each adaptor:driver nucleic acid complex comprises a driver nucleic acid and a second selected adaptor, wherein said second selected adaptor lacks the region which permits selective replication of tester nucleic acids, and wherein said first and second selected adaptors further comprise a substantially homologous region comprising a site recognized by a reagent capable of substantially preventing replication of double-stranded nucleic acids;

combining said adaptor:tester nucleic acid complexes and said adaptor:driver nucleic acid complexes so as to produce double-stranded hybrid nucleic acids;

adding a reagent capable of interacting with nucleic acid complexes to substantially prevent replication of said double-stranded hybrid nucleic acids; and replicating desired tester single-stranded nucleic acids.

35. A method for preferentially replicating one or more desired nucleic acids comprising:

preparing tester nucleic acids and driver nucleic acids from selected populations of nucleic acids;

producing adaptor:tester nucleic acid complexes with said tester nucleic acids, wherein each adaptor:tester nucleic acid complex comprises a tester nucleic acid and a first selected adaptor, wherein the first selected adaptor comprises a priming site;

producing adaptor:driver nucleic acid complexes with said driver nucleic acids, wherein each adaptor:driver nucleic acid complex comprises a driver nucleic acid and a second selected adaptor, and said first and second selected adaptors being the same or different;

combining said adaptor:tester nucleic acid complexes and said adaptor:driver nucleic acid complexes so as to produce double-stranded hybrid nucleic acids comprising double-stranded adaptor:tester nucleic acid complexes, double-stranded adaptor:driver nucleic acid complexes, and double-stranded adaptor:tester/adaptor:driver nucleic acid complexes;

adding a restriction enzyme capable of interacting with nucleic acid complexes to substantially prevent replication of all but double-stranded adaptor:tester nucleic acid complexes; and replicating said double-stranded adaptor tester nucleic acid complexes.

36. A kit for preferentially replicating or amplifying one or more desired nucleic acids comprising one or more selected adaptors, one or more selected primers, a restriction enzyme capable of substantially preventing replication or amplification of all but double-stranded desired nucleic acid complexes, and reagents for replicating or amplifying said double-stranded desired nucleic acid complexes.

37. A kit for preferentially replicating or amplifying one or more desired nucleic acids comprising one or more selected adaptors, one or more selected primers, one or more modified nucleotides capable of incorporation into a nucleic acid strand complementary to an adaptor:tester nucleic acid complex or an adaptor:driver nucleic acid complex, a reagent capable of substantially preventing replication or amplification of all but double-stranded desired nucleic acid complexes, and reagents for replicating or amplifying said double-stranded desired nucleic acid complexes.

38. A kit for preferentially replicating or amplifying one or more desired nucleic acids comprising one or more selected adaptors of claim 23, 24, 25, 26, 27, 28, 29 or 30, one or more selected primers, a cleavage reagent, and reagents for replicating or amplifying single-stranded desired nucleic acid complexes.

39. A method of claim 1, 16, 17, 18, 19, 34, or 35, wherein said producing of the adaptor:tester nucleic acid complexes comprises ligating a portion of said first selected adaptor to said tester nucleic acids and extending the ligated portion of said first selected adaptor to produce said adaptor:tester nucleic acid complexes.

40. A method of claim 1, 16, 17, 18, 19, 34, or 35, wherein said producing of the adaptor:driver nucleic acid complexes comprises ligating a portion of the second selected adaptor to said driver nucleic acids and extending the ligated portion of the second selected adaptor to produce said adaptor:driver nucleic acid complexes.

41. A method of claim 21 wherein said producing of the complexes comprises ligating a portion of said adaptors to said nucleic acids and extending the ligated portion of said adaptors to produce said complexes.

42. A method of claim 33 wherein said producing of the adaptor:tester nucleic acid complexes comprises ligating a portion of said first and second selected adaptors to said tester nucleic acids and extending the ligated portions of said first and second selected adaptors to produce said adaptor:tester nucleic acid complexes.

43. A method of claim 33 wherein said producing of the adaptor:driver nucleic acid complexes comprises ligating a portion of said third and fourth selected adaptors to said driver nucleic acids and extending the ligated portions of said third and fourth selected adaptors to produce said adaptor driver nucleic acid complexes.

* * * * *